(12) United States Patent
Webber et al.

(10) Patent No.: US 7,842,838 B2
(45) Date of Patent: Nov. 30, 2010

(54) PYRRO[1,2-B]PYRIDAZINONE INTERMEDIATES

(75) Inventors: Stephen E. Webber, San Diego, CA (US); Frank Ruebsam, San Diego, CA (US); Martin Tran, San Diego, CA (US); Peter Dragovich, San Diego, CA (US); Liansheng Li, San Diego, CA (US); Douglas Eric Murphy, San Diego, CA (US); David Kucera, Del Mar, CA (US); Zhongxiang Sun, San Diego, CA (US); Chinh Viet Tran, San Diego, CA (US)

(73) Assignee: Anadys Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 12/545,547

(22) Filed: Aug. 21, 2009

(65) Prior Publication Data

US 2009/0312570 A1    Dec. 17, 2009

Related U.S. Application Data

(62) Division of application No. 12/266,190, filed on Nov. 6, 2008, now Pat. No. 7,582,754, which is a division of application No. 11/766,697, filed on Jun. 21, 2007, now Pat. No. 7,462,611.

(60) Provisional application No. 60/815,578, filed on Jun. 22, 2006.

(51) Int. Cl.
    C07C 303/00    (2006.01)
(52) U.S. Cl. ............................ 564/86; 564/81
(58) Field of Classification Search .................. 564/81, 564/86
    See application file for complete search history.

(56) References Cited

U.S. PATENT DOCUMENTS 7,462,611 B2   12/2008   Ruebsam et al.
7,582,754 B2    9/2009   Webber et al.
2004/0087577 A1  5/2004  Pratt et al.
2005/0153877 A1  7/2005  Miao et al.
2006/0040927 A1  2/2006  Blake et al.
2006/0189602 A1  8/2006  Zhou et al.
2006/0211695 A1  9/2006  Borzilleri et al.
2006/0252785 A1 11/2006  Blake et al.

FOREIGN PATENT DOCUMENTS

WO    WO-01/85172 A1    11/2001
WO    WO-02/098424 A1   12/2002
WO    WO-03/059356 A2    7/2003
WO    WO-2006115221     11/2006

OTHER PUBLICATIONS

Goldfarb et al., Derivatives of 2,5-diaminobenzenesulfonamide, (Journal of the American Chemical Society (1943), 65, 738-739.*
Fisyuk et al., Synthesis of 5,6-Dihydropyridin-2(1H)-ones, 1,5,6,8,8a-Hexahydroisoquinolin-3(2H)-ones and 4a,5,6,7,8,8a-Hexahydroquinolin-2(1H)-ones by Intramolecular Wittig Reaction. Molecules, Feb. 28, 2002, vol. 7, pp. 124-128.
Tedesco et al., 3-(1,2,4)-benzothiadiazin-3-yl)-4-hydroxy-2(1H)-quinolinones, Potent Inhibitors of Hepatitis C Virus RNA-Dependent RNA Polymerase, J. Med. Chem. 49:971-983 (2006).
International Search Report PCT Application No. PCT/US2007/071826, Oct. 15, 2007.
Written Opinion of PCT Application No. PCT/US2007/071826, Oct. 15, 2007.
Goldfarb et al., Journal of the American Chemical Society, 65, 738-739 (1943).
Extended European Search Report, Apr. 13, 2010.

* cited by examiner

*Primary Examiner*—Jafar Parsa
(74) *Attorney, Agent, or Firm*—Connolly Bove Lodge & Hutz LLP

(57) ABSTRACT

The invention is directed to pyrro[1,2-b]pyridazinone compounds and pharmaceutical compositions containing such compounds that are useful in treating infections by hepatitis C virus.

4 Claims, No Drawings

PYRRO[1,2-B]PYRIDAZINONE INTERMEDIATES

This application is a divisional of U.S. application Ser. No. 12/266,190 filed Nov. 6, 2008, which claims priority to application Ser. No. 11/766,697, filed Jun. 21, 2007, which claims the benefit of U.S. Provisional Application No. 60/815,578, filed Jun. 22, 2006.

FIELD OF THE INVENTION

The invention is directed to pyrro[1,2-b]pyridazinone compounds and pharmaceutical compositions containing such compounds that are useful in treating infections by hepatitis C virus.

BACKGROUND OF THE INVENTION

Hepatitis C is a major health problem world-wide. The World Health Organization estimates that 170 million people are chronic carriers of the hepatitis C virus (HCV), with 4 million carriers in the United States alone. In the United States, HCV infection accounts for 40% of chronic liver disease and HCV disease is the most common cause for liver transplantation. HCV infection leads to a chronic infection and about 70% of persons infected will develop chronic histological changes in the liver (chronic hepatitis) with a 10-40% risk of cirrhosis and an estimated 4% lifetime risk of hepatocellular carcinoma. The CDC estimates that each year in the United States there are 35,000 new cases of HCV infection and approximately ten thousand deaths attributed to HCV disease.

The current standard of care is a pegylated interferon/ribavirin combination at a cost of approximately $31,000/year. These drugs have difficult dosing problems and side-effects that preclude their use in almost half of diagnosed patients. Pegylated interferon treatment is associated with menacing flu-like symptoms, irritability, inability to concentrate, suicidal ideation, and leukocytopenia. Ribavirin is associated with hemolytic anemia and birth defects.

The overall response to this standard therapy is low; approximately one third of patients do not respond. Of those who do respond, a large fraction relapses within six months of completing 6-12 months of therapy. As a consequence, the long-term response rate for all patients entering treatment is only about 50%. The relatively low response rate and the significant side-effects of current therapy anti-HCV drug treatments, coupled with the negative long term effects of chronic HCV infection, result in a continuing medical need for improved therapy. Antiviral pharmaceuticals to treat RNA virus diseases like HCV are few, and as described above are often associated with multiple adverse effects.

A number of recent publications have described NS5B inhibitors useful in the treatment of hepatitis C infection. See, e.g., U.S. Patent Application Publication No. US 2006/0189602 (disclosing certain pyridazinones); U.S. Patent Application Publication No. US 2006/0252785 (disclosing selected heterocyclics); and International Publication Nos. WO 03/059356, WO 2002/098424, and WO 01/85172 (each describing a particular class of substituted thiadiazines).

While there are, in some cases, medicines available to reduce disease symptoms, there are few drugs to effectively inhibit replication of the underlying virus. The significance and prevalence of RNA virus diseases, including but not limited to chronic infection by the hepatitis C virus, and coupled with the limited availability and effectiveness of current antiviral pharmaceuticals, have created a compelling and continuing need for new pharmaceuticals to treat these diseases.

SUMMARY OF THE INVENTION

The present invention describes novel pyrro[1,2-b]pyridazinone compounds and pharmaceutically acceptable salts thereof, which are useful in treating or preventing a hepatitis C virus infection in a patient in need thereof comprising administering to the patient a therapeutically or prophylactically effective amount of a pyrro[1,2-b]pyridazinone compound.

In a general aspect, the invention relates to compounds of Formula I

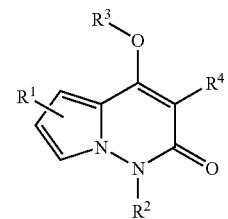

I wherein
$R^1$ is independently 1-3 moieties selected from hydrogen, halo, cyano, nitro, hydroxy, —$NR^8R^9$, $C_3$-$C_8$ cycloalkyl, $C_1$-$C_6$ alkyl, alkenyl, alkynyl, $C_1$-$C_6$ haloalkyl, $C_1$-$C_6$ hydroxyalkyl, $C_1$-$C_6$ alkoxy, —($C_1$-$C_6$ alkylene)$NR^8R^9$, —C(O)OH, —C(O)O($C_1$-$C_6$ alkyl), —C(O)NH($C_1$-$C_6$ alkyl), —C(O)($C_1$-$C_6$ alkyl), aryl, or heterocyclyl 1, 2, or 3 N, O, or S atoms, wherein $R^8$ and $R^9$ are independently H, $C_1$-$C_6$ alkyl, $C_3$-$C_8$ cycloalkyl, aryl, or heterocyclyl, or $R^8$ and $R^9$ combine with the N atom to which they are attached to form a 5- or 6-membered heterocyclyl ring,
$R^2$ is hydrogen, $C_3$-$C_8$ cycloalkyl, $C_1$-$C_7$ alkyl, alkenyl, alkynyl, $C_1$-$C_6$ haloalkyl, $C_1$-$C_6$ hydroxyalkyl, $C_1$-$C_6$ alkoxy, aryl, or heterocyclyl having 1, 2, or 3 N, O, or S atoms,
$R^3$ is hydrogen or $C_1$-$C_6$ alkyl,
$R^4$ is selected from

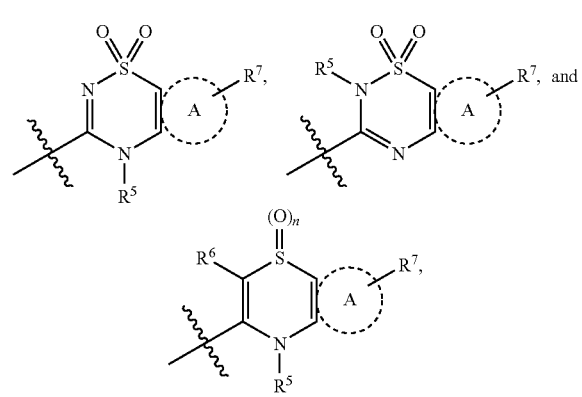

wherein n is 0, 1, or 2,
$R^5$ is hydrogen or $C_1$-$C_6$ alkyl,
$R^6$ is hydrogen, halo, or $C_1$-$C_6$ alkyl, and
Ring A is 5 or 6-membered aryl or heterocyclyl, optionally substituted by 1-3 $R^7$ moieties, wherein $R^7$ is H, alkyl, alkenyl, alkynyl, aryl, heterocyclyl, halo, cyano, nitro, OH, —O-alkyl, —O—($C_1$-$C_6$ hydroxyalkyl), —O—($C_1$-$C_6$ alkoxy), —O—($C_1$-$C_6$ alkylene)-cyano, —O—($C_1$-$C_6$ alkylene)-C(O)$R^{10}$, —OCH$R^{10}$C(O)O—$R^{11}$, —OCH$R^{10}$C(O)NHOH, —O—($C_1$-$C_6$ alkyl)-C(O)N$R^{11}R^{12}$, —O—($C_1$-$C_6$ allylene)-N$R^{10}$C(O)$R^{11}$, —O—($C_1$-$C_6$ alkylene)-N$R^{10}$C(O)O$R^{11}$, —O—($C_1$-$C_6$ alkylene)-N$R^{10}$C(O)N$R^{11}R^{12}$, —OCH$R^{10}$C(O)N$R^{11}R^{12}$, —O—($C_1$-$C_6$ alkylene)-S(O)$R^{10}$, —O—($C_1$-$C_6$ alkyl)-S(O)$_2R^{10}$, —O—($C_1$-$C_6$ alkylene)-S(O)$_2$N$R^{11}R^{12}$, —O—($C_1$-$C_6$ alkylene)-N$R^{10}$S(O)$_2$N$R^{11}R^{12}$, —O—($C_1$-$C_6$ alkylene)-N$R^{10}$S(O)$_2$N$R^{11}$, —O—($C_1$-$C_6$ alkylene)-S(O)$_2$ $R^{10}$, —O—($C_1$-$C_6$ alkylene)-N$R^{11}R^{12}$, —($C_1$-$C_6$ alkylene)-S(O)$_2R^{10}$, —($C_1$-$C_6$ alkylene)-S(O)$_2$N$R^{11}R^{12}$, —($C_1$-$C_6$ alkylene)-S(O)$R^{10}$, —($C_1$-$C_6$ alkylene)-C(O) $R^{10}$, —($C_1$-$C_6$ alkylene)-C(O)N$R^{11}R^{12}$, —($C_1$-$C_6$ alkylene)-N$R^{10}$C(O)$R^{11}$, —($C_1$-$C_6$ alkylene)-N$R^{10}$S(O)$_2$ $R^{11}R^{12}$, —($C_1$-$C_6$ alkylene)-N$R^{10}$C(O)O$R^{11}$, —($C_1$-$C_6$ alkylene)-N$R^{10}$C(O)N$R^{11}R^{12}$, —($C_1$-$C_6$ alkylene)-N$R^{10}$S (O)$_2$N$R^{11}R^{12}$, —($C_1$-$C_6$ alkylene)-C(O)O$R^{10}$, —($C_1$-$C_6$ alkylene)-N$R^{11}R^{12}$, —N$R^{11}R^{12}$, —N$R^{11}$C(O)$R^{12}$, —N$R^{10}$S(O)$_2R^{11}$, —N$R^{10}$S(O)$_2$N$R^{11}R^{12}$, —C(O)$R^{10}$, —S(O)$R^{10}$, —S(O)$_2R^{10}$, or —S(O)$_2$N$R^{11}R^{12}$, wherein $R^{10}$, $R^{11}$, and $R^{12}$ are independently H, $C_1$-$C_6$ alkyl, $C_3$-$C_8$ cycloalkyl, aryl, or heterocyclyl, or $R^{10}$ and $R^{11}$ or $R^{11}$ and $R^{12}$ combine with the atom(s) to which they are attached to form a 5- or 6-membered heterocyclyl ring, wherein the above alkyl, alkenyl, alkynyl, aryl, cycloalkyl, or heterocyclyl moieties provided in $R^1$, $R^2$, $R^7$, $R^8$, $R^9$, $R^{10}$, $R^{11}$, and $R^{12}$ are each optionally and independently substituted by 1-3 substituents selected from alkylamine,
amino,
aryl, cycloalkyl, heterocyclyl,
$C_1$-$C_6$ alkyl, $C_1$-$C_6$ haloalkyl, $C_1$-$C_6$ hydroxyalkyl, $C_1$-$C_6$ alkoxy, $C_1$-$C_6$ alkylamine, $C_1$-$C_6$ dialkylamine, $C_2$-$C_6$ alkenyl, or $C_2$-$C_6$ alkynyl, wherein each of which may be interrupted by one or more hetero atoms,
carboxyl,
cyano,
halo,
hydroxy,
nitro,
oxo,
—C(O)OH, —C(O)$_2$—($C_1$-$C_6$ alkyl), —C(O)$_2$—($C_3$-$C_8$ cycloalkyl), —C(O)$_2$-(aryl), —C(O)$_2$-(heterocyclyl), —C(O)$_2$—($C_1$-$C_6$ alkylene)aryl, —C(O)$_2$—($C_1$-$C_6$ alkylene)heterocyclyl, —C(O)$_2$—($C_1$-$C_6$ alkylene)cycloalkyl, —C(O)($C_1$-$C_6$ alkyl), —C(O)($C_3$-$C_8$ cycloalkyl), —C(O)(aryl), —C(O)(heterocyclyl), —C(O)($C_1$-$C_6$ alkylene)aryl, —C(O)($C_1$-$C_6$ alkylene) heterocyclyl, and —C(O)($C_1$-$C_6$ alkyl)cycloalkyl, wherein each of the above optional substituents can be further optionally substituted by 1-5 substituents selected from amino, cyano, halo, hydroxy, nitro, $C_1$-$C_6$ alkylamine, $C_1$-$C_6$ dialkylamine, $C_1$-$C_6$ alkyl, $C_1$-$C_6$ alkoxy, $C_1$-$C_6$ alkenyl, and $C_1$-$C_6$ hydroxyalkyl, wherein each alkyl is optionally substituted by one or more halo substituents, or a pharmaceutically acceptable salt, hydrate, solvate, tautomer or stereoisomer thereof.

In one embodiment, the invention relates to compounds of Formula I wherein $R^1$ is selected from hydrogen, halo, cyano, hydroxyl, —N$R^8R^9$, $C_3$-$C_8$ cycloalkyl, $C_1$-$C_6$ alkyl, alkenyl, alkynyl, $C_1$-$C_6$ alkoxy, —($C_1$-$C_6$ alkylene)N$R^8R^9$, —C(O) O$R^8$, —C(O)N$R^8R^9$, —C(O)$R^8$, aryl, or heterocyclyl having 1, 2, or 3 N, O, or S atoms, wherein $R^8$ and $R^9$ are independently H, $C_1$-$C_6$ alkyl, $C_3$-$C_8$ cycloalkyl, aryl, or heterocyclyl, or $R^8$ and $R^9$ combine with the N atom to which they are attached to form a 5- or 6-membered heterocyclyl ring.

In another embodiment, the invention relates to compounds of Formula I wherein $R^1$ is selected from

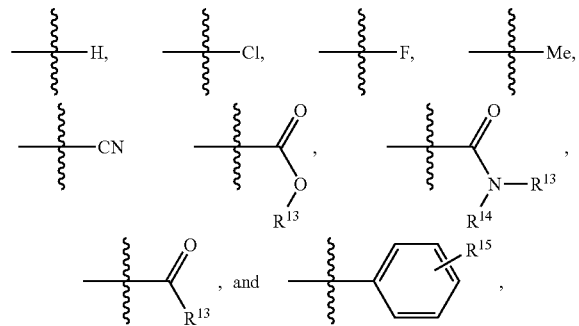

wherein $R^{13}$, $R^{14}$ and $R^{15}$ are independently selected from hydrogen, alkylamine, amino, aryl, cycloalkyl, heterocyclyl, $C_1$-$C_6$ alkyl, $C_1$-$C_6$ alkoxy, carboxyl, cyano, halo, and hydroxyl, or $R^{13}$ and $R^{14}$ combine with the N atom to which they are attached to form a 5- or 6-membered heterocyclyl ring.

In a further embodiment, $R^1$ is selected from hydrogen, fluoro, cyano, and methyl.

In one embodiment, the invention relates to compounds of Formula I wherein $R^2$ is selected from $C_3$-$C_8$ cycloalkyl, $C_1$-$C_6$ alkyl, alkenyl, alkynyl, aryl, and heterocyclyl having 1, 2, or 3 N, O, or S atoms, wherein the alkyl, alkenyl, alkynyl, aryl, cycloalkyl, or heterocyclyl moieties are each optionally and independently substituted by 1-3 substituents selected from aryl, cycloalkyl, heterocyclyl, $C_1$-$C_6$ alkyl, $C_1$-$C_6$ alkoxy, $C_1$-$C_6$ alkylamine, $C_2$-$C_6$ alkenyl, or $C_2$-$C_6$ alkynyl, wherein each of which may be interrupted by one or more hetero atoms and optionally substituted by cyano or halo.

In another embodiment, the invention relates to compounds of Formula I wherein $R^2$ is selected from

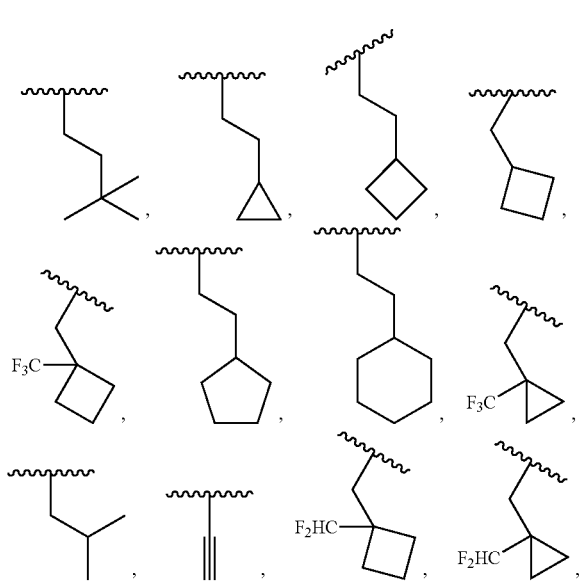

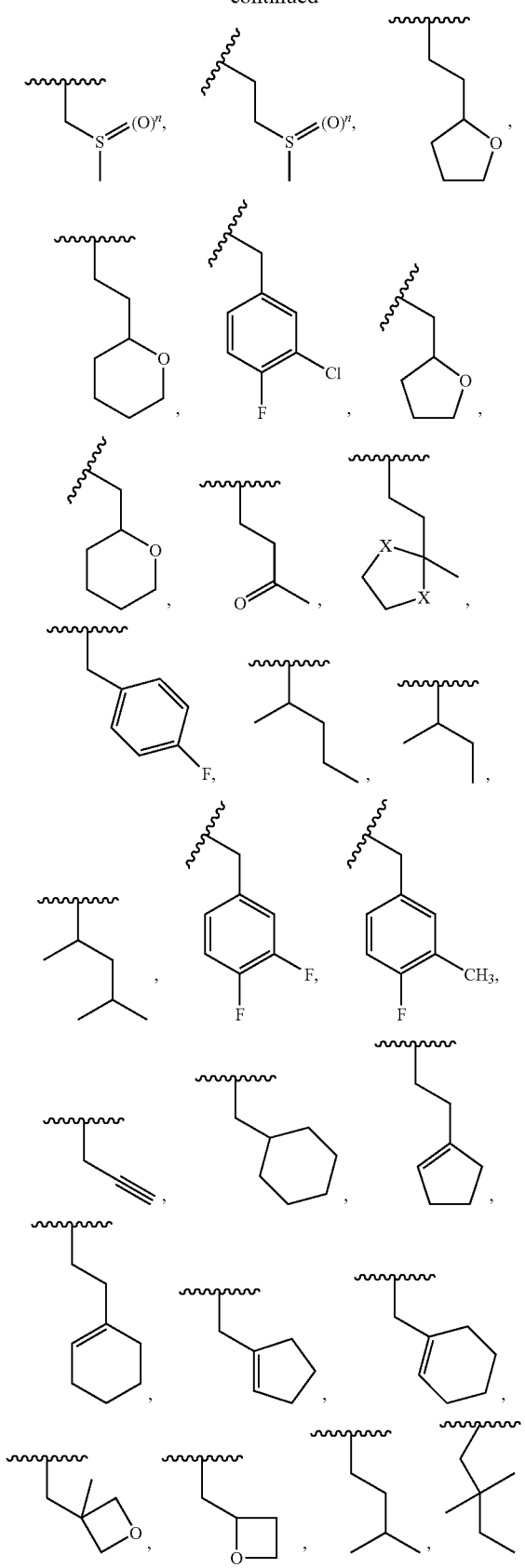
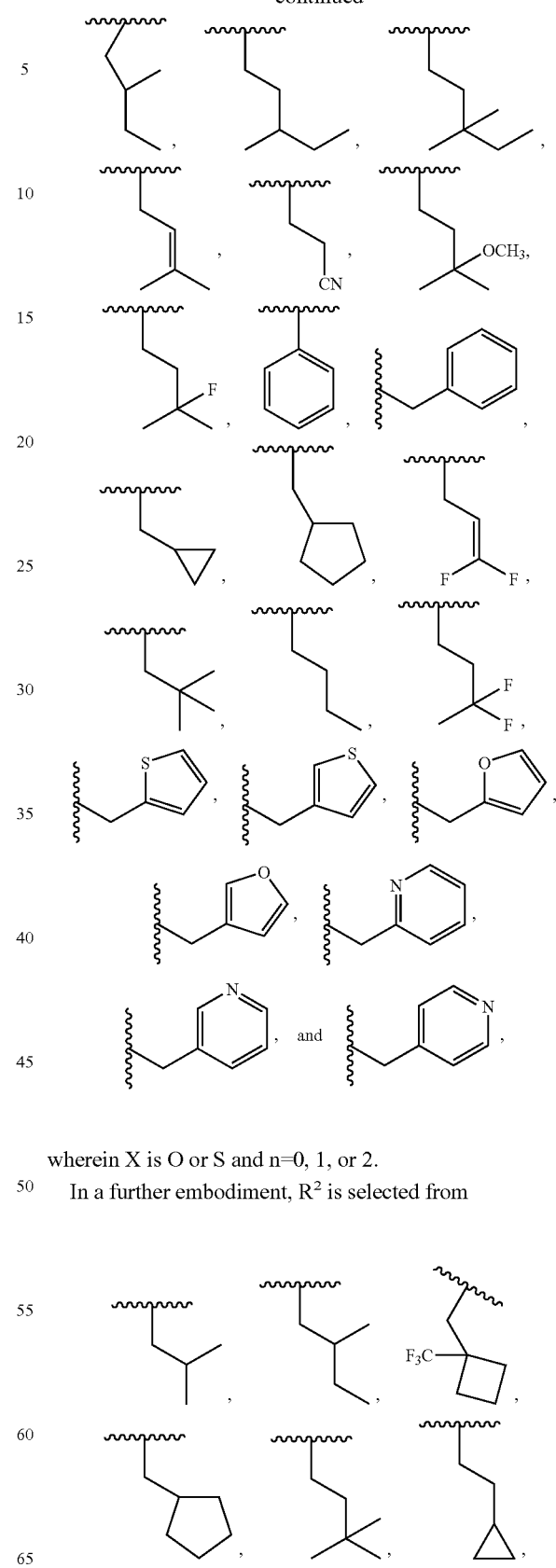
wherein X is O or S and n=0, 1, or 2.
In a further embodiment, R² is selected from -continued

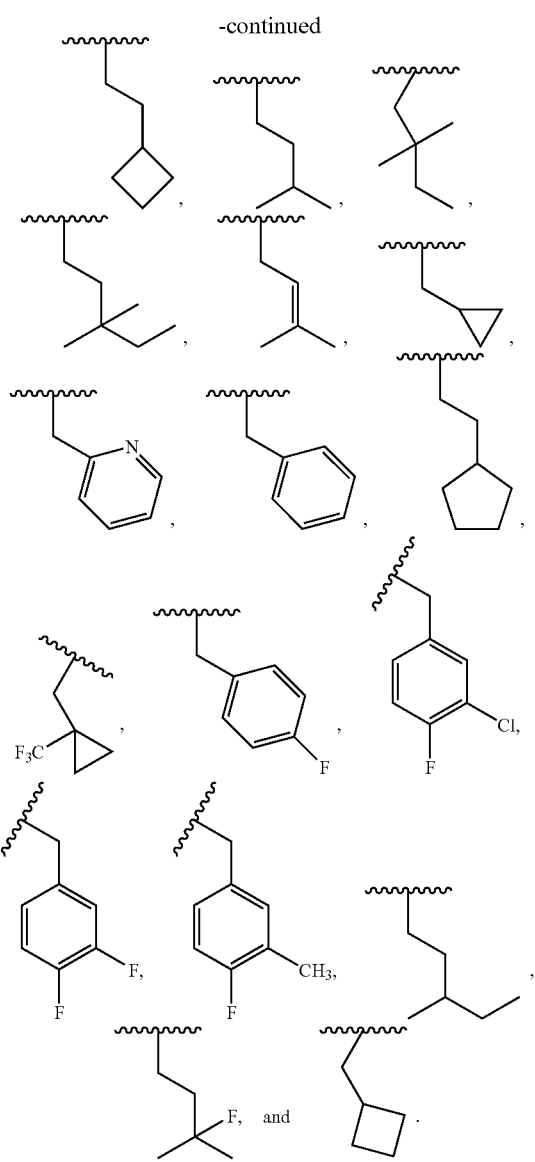

In yet another embodiment $R^2$ is selected from

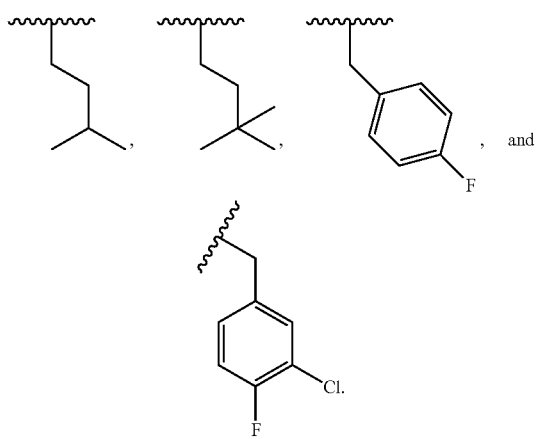

In one embodiment, the invention relates to compounds of Formula I wherein $R^3$ and $R^5$ are independently selected from hydrogen, methyl, and ethyl.

In one embodiment, the invention relates to compounds of Formula I wherein $R^6$ is selected from hydrogen, fluoro, methyl, and ethyl.

In one embodiment, the invention relates to compounds of Formula I wherein n is 2.

In one embodiment, the invention relates to compounds of Formula I wherein Ring A is selected from

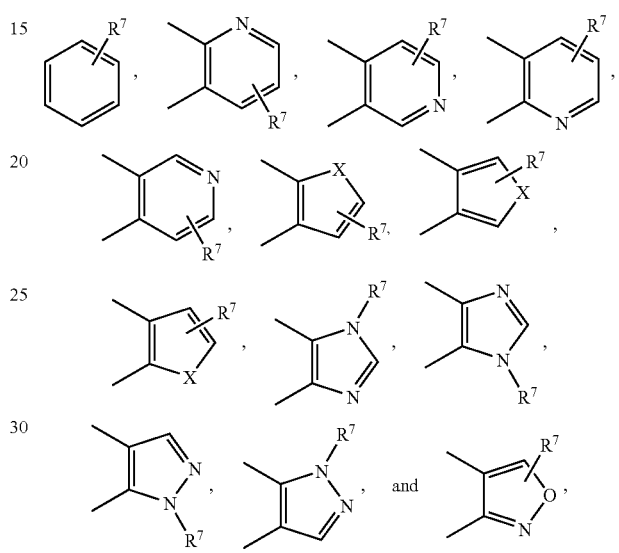

wherein X is S, O, NH, or —N($C_1$-$C_6$ alkyl).

In another embodiment, Ring A is selected from

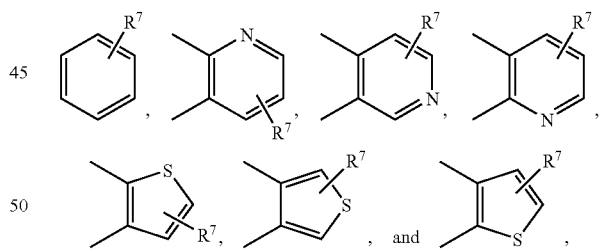

In a further embodiment, Ring A is

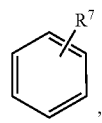

wherein $R^7$ is hydrogen, —($C_1$-$C_6$ alkylene)-S(O)$_2$NR$^{11}$R$^{12}$, —($C_1$-$C_6$ alkylene)-S(O)R$^{10}$, —($C_1$-$C_6$ alkylene)-S(O)$_2$R$^{10}$, —NR$^{10}$S(O)$_2$R$^{11}$, or —NR$^{10}$S(O)$_2$NR$^{11}$R$^{12}$.

In a further embodiment, $R^7$ is selected from

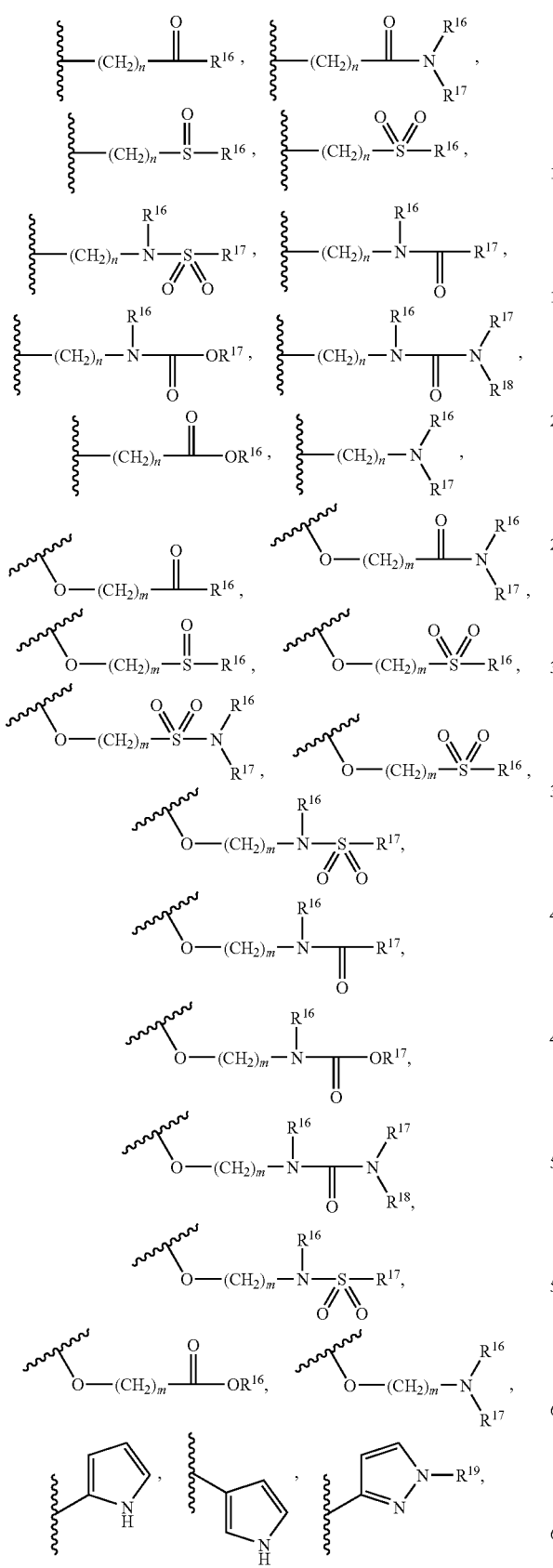
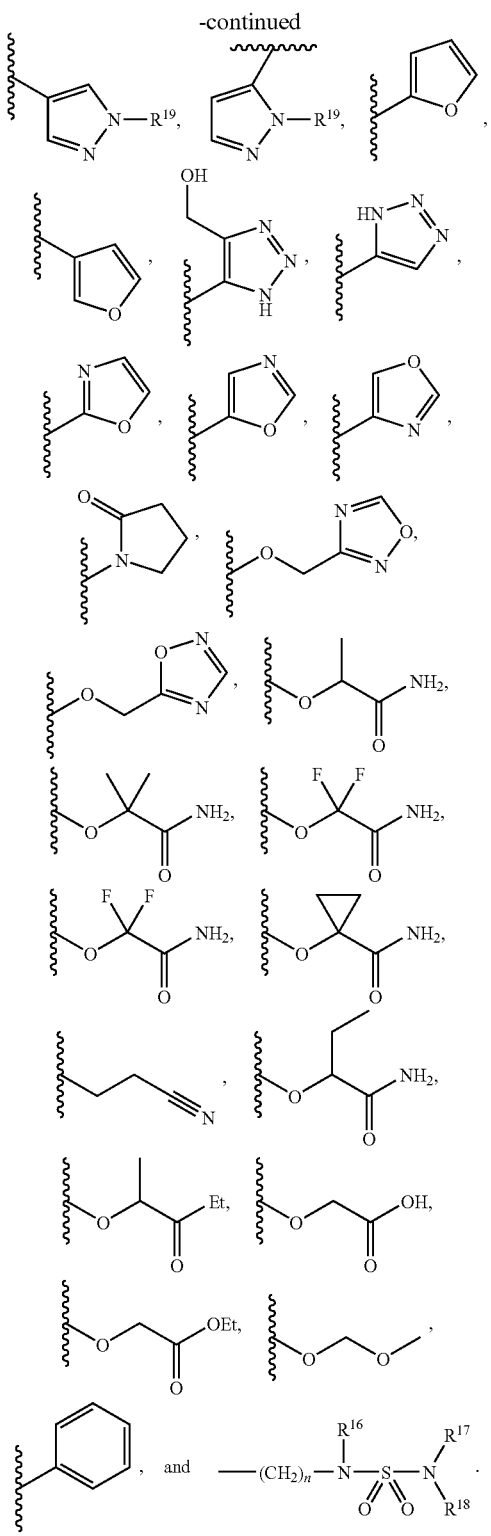

wherein n is an integer from 0 to 6, m is an integer from 1 to 6, $R^{16}$, $R^{17}$, and $R^{18}$ are independently selected from hydrogen, $C_1$-$C_6$ alkyl, $C_3$-$C_8$ cycloalkyl, aryl, and heterocyclyl, or $R^{16}$ and $R^{17}$ or $R^{17}$ and $R^{18}$ combine with the atom(s) to which they are attached to form a 5- or 6-membered heterocyclyl ring, $R^{19}$ is hydrogen, $C_1$-$C_6$ alkyl, $C_3$-$C_8$ cycloalkyl —$S(O)_2$ $R^{10}$, or —$S(O)_2NR^{11}R^{12}$, wherein $R^{10}$, $R^{11}$, and $R^{12}$ are independently selected from hydrogen, $C_1$-$C_6$ alkyl, $C_3$-$C_8$ cycloalkyl, aryl, or heterocyclyl, or $R^{11}$ and $R^{12}$ combine with the N atom to which they are attached to form a 5- or 6-membered heterocyclyl ring.
In another embodiment, the invention relates to compounds selected from
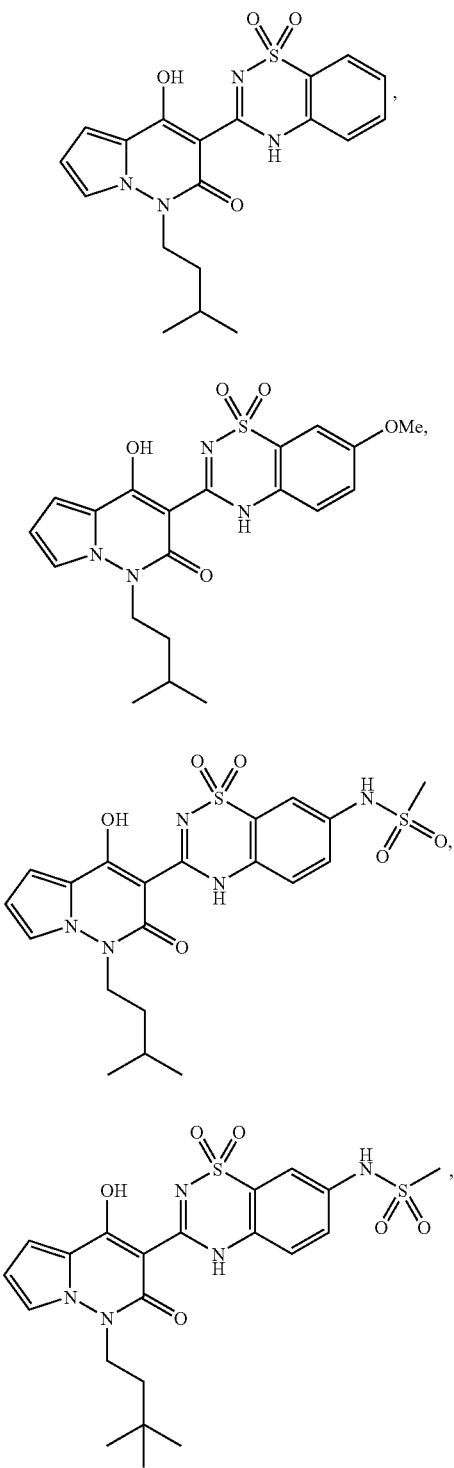
-continued
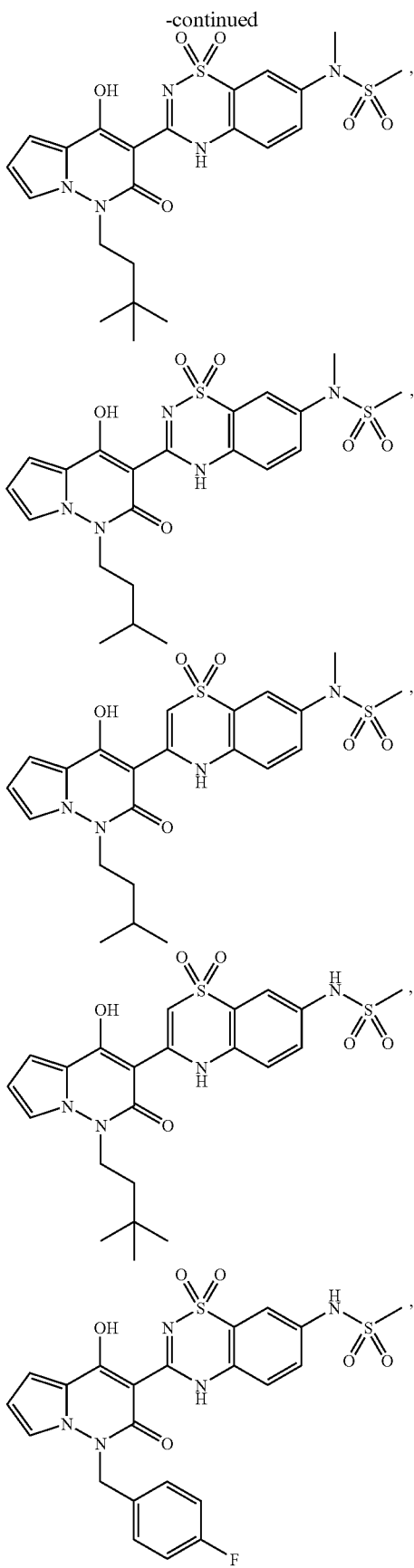

-continued

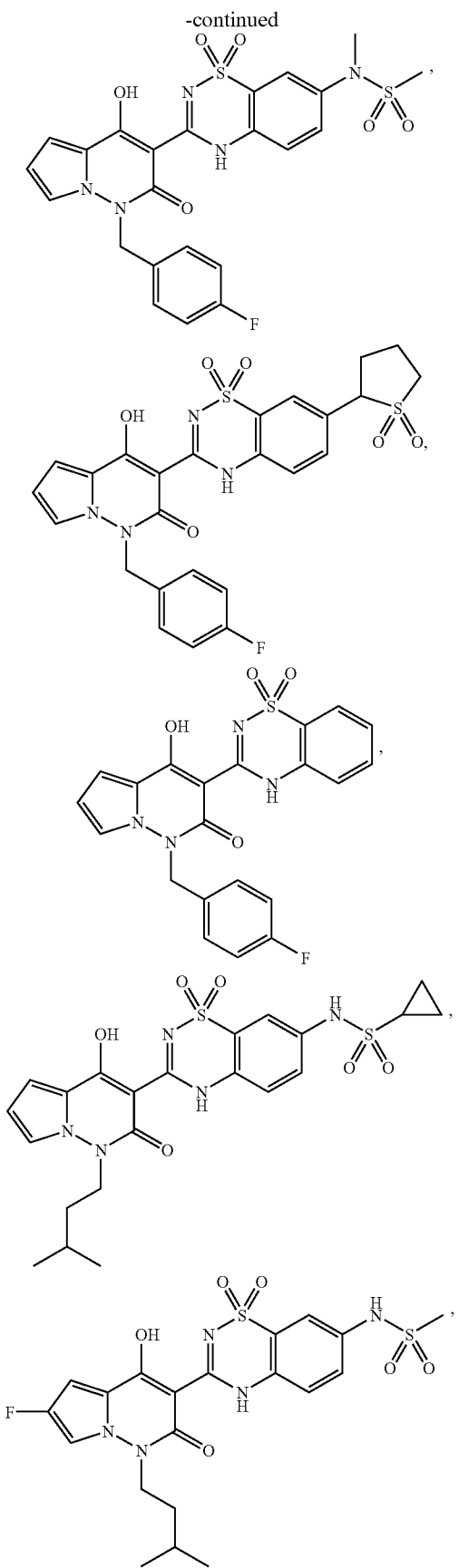
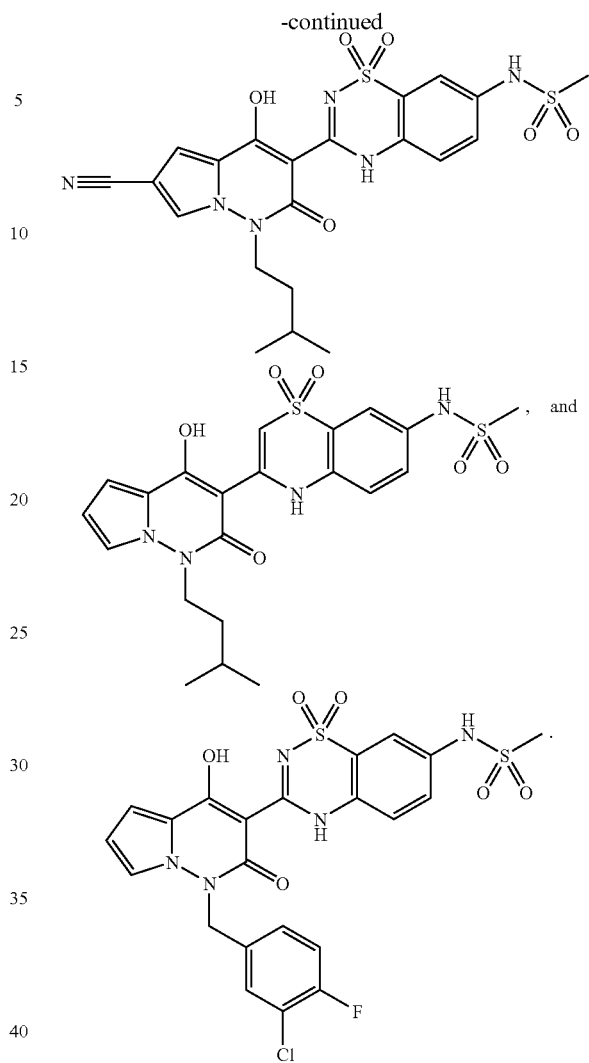

The invention is also directed to pharmaceutically acceptable salts, hydrates, and solvates of the compounds of Formula I. Advantageous methods of making the compounds of Formula I are also described.

In one aspect, the invention encompasses a method for treating or preventing hepatitis C virus infection in a mammal in need thereof, preferably in a human in need thereof, comprising administering to the patient a therapeutically or prophylactically effective amount of a Formula I compound. In one embodiment, the invention encompasses a method for treating or preventing hepatitis C virus infection by administering to a patient in need thereof a therapeutically or prophylactically effective amount of a Formula I compound that is an inhibitor of HCV NS5B polymerase.

In another aspect, the invention encompasses a method for treating or preventing hepatitis C virus infection in a patient in need thereof, comprising administering to the patient a therapeutically or prophylactically effective amount of a compound of Formula I and a pharmaceutically acceptable excipient, carrier, or vehicle.

In another aspect, the invention encompasses a method for treating or preventing hepatitis C virus infection in a patient in need thereof, comprising administering to the patient a therapeutically or prophylactically effective amount of a compound of Formula I and an additional therapeutic agent, preferably an additional antiviral agent or an immunomodulatory agent.

DETAILED DESCRIPTION OF THE INVENTION

Where the following terms are used in this specification, they are used as defined below:

The terms "comprising," "having" and "including" are used herein in their open, non-limiting sense.

The term "alkyl", as used herein, unless otherwise indicated, includes saturated monovalent hydrocarbon radicals having straight, branched, or cyclic moieties (including fused and bridged bicyclic and spirocyclic moieties), or a combination of the foregoing moieties. For an alkyl group to have cyclic moieties, the group must have at least three carbon atoms.

The term "alkylene", as used herein, unless otherwise indicated, includes a divalent radical derived from alkyl, as exemplified by —$CH_2CH_2CH_2CH_2$—.

The term "alkenyl", as used herein, unless otherwise indicated, includes alkyl moieties having at least one carbon-carbon double bond wherein alkyl is as defined above and including E and Z isomers of said alkenyl moiety.

The term "alkynyl", as used herein, unless otherwise indicated, includes alkyl moieties having at least one carbon-carbon triple bond wherein alkyl is as defined above.

The term "alkoxy", as used herein, unless otherwise indicated, includes O-alkyl groups wherein alkyl is as defined above.

The term "Me" means methyl, "Et" means ethyl, and "Ac" means acetyl.

The term "cycloalkyl", as used herein, unless otherwise indicated refers to a non-aromatic, saturated or partially saturated, monocyclic or fused, spiro or unfused bicyclic or tricyclic hydrocarbon referred to herein containing a total of from 3 to 10 carbon atoms, preferably 5-8 ring carbon atoms. Exemplary cycloalkyls include monocyclic rings having from 3-7, preferably 3-6, carbon atoms, such as cyclopropyl, cyclobutyl, cyclopentyl, cyclohexyl, cycloheptyl and the like. Illustrative examples of cycloalkyl are derived from, but not limited to, the following:

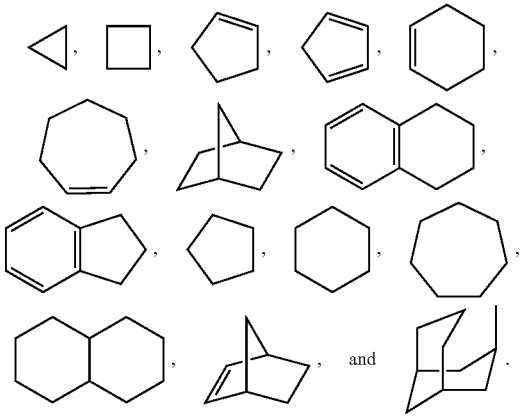

The term "aryl", as used herein, unless otherwise indicated, includes an organic radical derived from an aromatic hydrocarbon by removal of one hydrogen, such as phenyl or naphthyl.

The term "heterocyclic" or "heterocyclyl", as used herein, unless otherwise indicated, includes aromatic (e.g., heteroaryls) and non-aromatic heterocyclic groups containing one to four heteroatoms each selected from O, S and N, wherein each heterocyclic group has from 4-10 atoms in its ring system, and with the proviso that the ring of said group does not contain two adjacent O atoms. Non-aromatic heterocyclic groups include groups having only 3 atoms in their ring system, but aromatic heterocyclic groups must have at least 5 atoms in their ring system. The heterocyclic groups include benzo-fused ring systems. An example of a 4 membered heterocyclic group is azetidinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). The 4-10 membered heterocyclic may be optionally substituted on any ring carbon, sulfur, or nitrogen atom(s) by one to two oxo, per ring. An example of a heterocyclic group wherein 2 ring carbon atoms are substituted with oxo moieties is 1,1-dioxo-thiomorpholinyl. Other illustrative examples of 4-10 membered heterocyclic are derived from, but not limited to, the following:

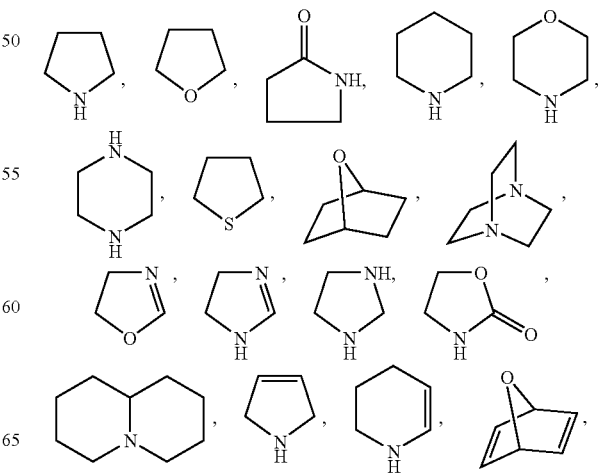

-continued

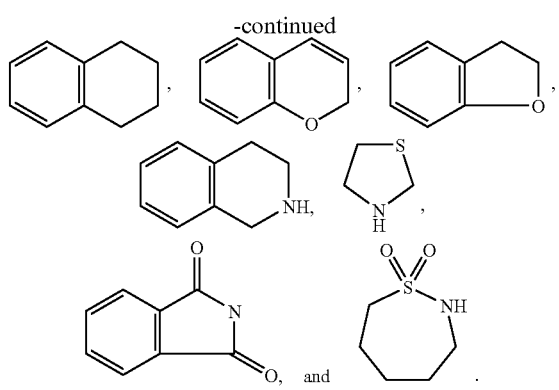

Unless defined otherwise, "alkyl," "alkylene," "alkenyl," "alkynyl," "aryl," "cycloalkyl," or "heterocyclyl" are each optionally and independently substituted by 1-3 substituents selected from alkylamine, amino, aryl, cycloalkyl, heterocyclyl, $C_1$-$C_6$ alkyl, $C_1$-$C_6$ haloalkyl, $C_1$-$C_6$ hydroxyalkyl, $C_1$-$C_6$ alkoxy, $C_1$-$C_6$ alkylamine, $C_1$-$C_6$ dialkylamine, $C_2$-$C_6$ alkenyl, or $C_2$-$C_6$ alkynyl, wherein each of which may be interrupted by one or more hetero atoms, carboxyl, cyano, halo, hydroxy, nitro, —C(O)OH, —C(O)$_2$—($C_1$-$C_6$ alkyl), —C(O)$_2$—($C_3$-$C_8$ cycloalkyl), —C(O)$_2$-(aryl), —C(O)$_2$-(heterocyclyl), —C(O)$_2$—($C_1$-$C_6$ alkylene)aryl, —C(O)$_2$—($C_1$-$C_6$ alkylene)heterocyclyl, —C(O)$_2$—($C_1$-$C_6$ alkylene)cycloalkyl, —C(O)($C_1$-$C_6$ alkyl), —C(O)($C_3$-$C_8$ cycloalkyl), —C(O)(aryl), —C(O)(heterocyclyl), —C(O)($C_1$-$C_6$ alkylene)aryl, —C(O)($C_1$-$C_6$ alkylene)heterocyclyl, and —C(O) ($C_1$-$C_6$ alkylene)cycloalkyl, wherein each of these optional substituents can be further optionally substituted by 1-5 substituents selected from amino, cyano, halo, hydroxy, nitro, $C_1$-$C_6$ alkylamine, $C_1$-$C_6$ dialkylamine, $C_1$-$C_6$ alkyl, $C_1$-$C_6$ alkoxy, $C_1$-$C_6$ alkenyl, and $C_1$-$C_6$ hydroxyalkyl, wherein each alkyl is optionally substituted by one or more halo substituents, e.g., $CF_3$.

The term "immunomodulator" refers to natural or synthetic products capable of modifying the normal or aberrant immune system through stimulation or suppression.

The term "preventing" refers to the ability of a compound or composition of the invention to prevent a disease identified herein in patients diagnosed as having the disease or who are at risk of developing such disease. The term also encompasses preventing further progression of the disease in patients who are already suffering from or have symptoms of such disease.

The term "patient" or "subject" means an animal (e.g., cow, horse, sheep, pig, chicken, turkey, quail, cat, dog, mouse, rat, rabbit, guinea pig, etc.) or a mammal, including chimeric and transgenic animals and mammals. In the treatment or prevention of HCV infection, the term "patient" or "subject" preferably means a monkey or a human, most preferably a human. In a specific embodiment the patient or subject is infected by or exposed to the hepatitis C virus. In certain embodiments, the patient is a human infant (age 0-2), child (age 2-17), adolescent (age 12-17), adult (age 18 and up) or geriatric (age 70 and up) patient. In addition, the patient includes immunocompromised patients such as HIV positive patients, cancer patients, patients undergoing immunotherapy or chemotherapy. In a particular embodiment, the patient is a healthy individual, i.e., not displaying symptoms of other viral infections.

The term a "therapeutically effective amount" refers to an amount of the compound of the invention sufficient to provide a benefit in the treatment or prevention of viral disease, to delay or minimize symptoms associated with viral infection or viral-induced disease, or to cure or ameliorate the disease or infection or cause thereof. In particular, a therapeutically effective amount means an amount sufficient to provide a therapeutic benefit in vivo. Used in connection with an amount of a compound of the invention, the term preferably encompasses a non-toxic amount that improves overall therapy, reduces or avoids symptoms or causes of disease, or enhances the therapeutic efficacy of or synergies with another therapeutic agent.

The term a "prophylactically effective amount" refers to an amount of a compound of the invention or other active ingredient sufficient to result in the prevention of infection, recurrence or spread of viral infection. A prophylactically effective amount may refer to an amount sufficient to prevent initial infection or the recurrence or spread of the infection or a disease associated with the infection. Used in connection with an amount of a compound of the invention, the term preferably encompasses a non-toxic amount that improves overall prophylaxis or enhances the prophylactic efficacy of or synergies with another prophylactic or therapeutic agent.

The term "in combination" refers to the use of more than one prophylactic and/or therapeutic agents simultaneously or sequentially and in a manner that their respective effects are additive or synergistic.

The term "treating" refers to:

(i) preventing a disease, disorder, or condition from occurring in an animal that may be predisposed to the disease, disorder and/or condition, but has not yet been diagnosed as having it;

(ii) inhibiting the disease, disorder, or condition, i.e., arresting its development; and (iii) relieving the disease, disorder, or condition, i.e., causing regression of the disease, disorder, and/or condition.

The terms "R" and "S" indicate the specific stereochemical configuration of a substituent at an asymmetric carbon atom in a chemical structure as drawn.

The term "rac" indicates that a compound is a racemate, which is defined as an equimolar mixture of a pair of enantiomers. A "rac" compound does not exhibit optical activity. The chemical name or formula of a racemate is distinguished from those of the enantiomers by the prefix (±)- or rac- (or racem-) or by the symbols RS and SR.

The compounds of the invention may exhibit the phenomenon of tautomerism. While Formula I cannot expressly depict all possible tautomeric forms, it is to be understood that Formula I is intended to represent any tautomeric form of the depicted compound and is not to be limited merely to a specific compound form depicted by the formula drawings. For illustration, and in no way limiting the range of tautomers, the compounds of Formula I may exist as the following:

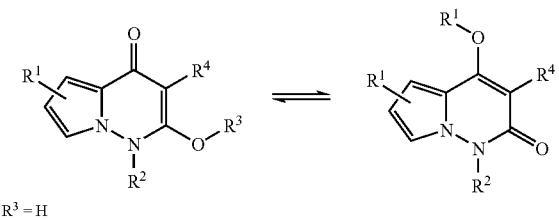

$R^3 = H$

Some of the inventive compounds may exist as single stereoisomers (i.e., essentially free of other stereoisomers), racemates, and/or mixtures of enantiomers and/or diastereomers.

All such single stereoisomers, racemates and mixtures thereof are intended to be within the scope of the present invention. Preferably, the inventive compounds that are optically active are used in optically pure form.

As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, the compounds of the present invention are used in a form that is at least 90% free of other enantiomers or diastereomers of the compounds, that is, a form that contains at least 90% of a single isomer (80% enantiomeric excess ("e.e.") or diastereomeric excess ("d.e.")), more preferably at least 95% (90% e.e. or d.e.), even more preferably at least 97.5% (95% e.e. or d.e.), and most preferably at least 99% (98% e.e. or d.e.).

Additionally, the Formula I is intended to cover solvated as well as unsolvated forms of the identified structures. For example, Formula I includes compounds of the indicated structure in both hydrated and non-hydrated forms. Other examples of solvates include the structures in combination with isopropanol, ethanol, methanol, DMSO, ethyl acetate, acetic acid, or ethanolamine.

In addition to compounds of Formula I, the invention includes pharmaceutically acceptable prodrugs, pharmaceutically active metabolites, and pharmaceutically acceptable salts of such compounds and metabolites.

"A pharmaceutically acceptable prodrug" is a compound that may be converted under physiological conditions or by solvolysis to the specified compound or to a pharmaceutically acceptable salt of such compound prior to exhibiting its pharmacological effect (s). Typically, the prodrug is formulated with the objective(s) of improved chemical stability, improved patient acceptance and compliance, improved bioavailability, prolonged duration of action, improved organ selectivity, improved formulation (e.g., increased hydrosolubility), and/or decreased side effects (e.g., toxicity). The prodrug can be readily prepared from the compounds of Formula I using methods known in the art, such as those described by *Burger's Medicinal Chemistry and Drug Chemistry*, 1, 172-178, 949-982 (1995). See also Bertolini et al., *J. Med. Chem.*, 40, 2011-2016 (1997); Shan, et al., *J. Pharm. Sci.*, 86 (7), 765-767; Bagshawe, *Drug Dev. Res.*, 34, 220-230 (1995); Bodor, *Advances in Drug Res.*, 13, 224-331 (1984); Bundgaard, *Design of Prodrugs* (Elsevier Press 1985); Larsen, *Design and Application of Prodrugs*, Drug Design and Development (Krogsgaard-Larsen et al., eds., Harwood Academic Publishers, 1991); Dear et al., *J. Chromatogr. B*, 748, 281-293 (2000); Spraul et al., *J. Pharmaceutical & Biomedical Analysis*, 10, 601-605 (1992); and Prox et al., *Xenobiol.*, 3, 103-112 (1992).

"A pharmaceutically active metabolite" is intended to mean a pharmacologically active product produced through metabolism in the body of a specified compound or salt thereof. After entry into the body, most drugs are substrates for chemical reactions that may change their physical properties and biologic effects. These metabolic conversions, which usually affect the polarity of the Formula I compounds, alter the way in which drugs are distributed in and excreted from the body. However, in some cases, metabolism of a drug is required for therapeutic effect. For example, anticancer drugs of the anti-metabolite class must be converted to their active forms after they have been transported into a cancer cell.

Since most drugs undergo metabolic transformation of some kind, the biochemical reactions that play a role in drug metabolism may be numerous and diverse. The main site of drug metabolism is the liver, although other tissues may also participate.

A feature characteristic of many of these transformations is that the metabolic products, or "metabolites," are more polar than the parent drugs, although a polar drug does sometime yield a less polar product. Substances with high lipid/water partition coefficients, which pass easily across membranes, also diffuse back readily from tubular urine through the renal tubular cells into the plasma. Thus, such substances tend to have a low renal clearance and a long persistence in the body. If a drug is metabolized to a more polar compound, one with a lower partition coefficient, its tubular reabsorption will be greatly reduced. Moreover, the specific secretory mechanisms for anions and cations in the proximal renal tubules and in the parenchymal liver cells operate upon highly polar substances.

As a specific example, phenacetin (acetophenetidin) and acetanilide are both mild analgesic and antipyretic agents, but are transformed within the body to a more polar and more effective metabolite, p-hydroxyacetanilide (acetaminophen), which is widely used today. When a dose of acetanilide is given to a person, the successive metabolites peak and decay in the plasma sequentially. During the first hour, acetanilide is the principal plasma component. In the second hour, as the acetanilide level falls, the metabolite acetaminophen concentration reaches a peak. Finally, after a few hours, the principal plasma component is a further metabolite that is inert and can be excreted from the body. Thus, the plasma concentrations of one or more metabolites, as well as the drug itself, can be pharmacologically important.

"A pharmaceutically acceptable salt" is intended to mean a salt that retains the biological effectiveness of the free acids and bases of the specified compound and that is not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present invention with a mineral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an α-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds and salts may exist in different crystal or polymorphic forms, all of which are intended to be within the scope of the present invention and specified formulas.

Methods of Treatment and Prevention of Hepatitis C Viral Infections

The present invention provides methods for treating or preventing a hepatitis C virus infection in a patient in need thereof.

The present invention further provides methods for introducing a therapeutically effective amount of the Formula I compound or combination of such compounds into the blood stream of a patient in the treatment and/or prevention of hepatitis C viral infections.

The magnitude of a prophylactic or therapeutic dose of a Formula I compound of the invention or a pharmaceutically acceptable salt, solvate, or hydrate, thereof in the acute or chronic treatment or prevention of an infection will vary, however, with the nature and severity of the infection, and the route by which the active ingredient is administered. The dose, and in some cases the dose frequency, will also vary according to the infection to be treated, the age, body weight, and response of the individual patient. Suitable dosing regimens can be readily selected by those skilled in the art with due consideration of such factors.

The methods of the present invention are particularly well suited for human patients. In particular, the methods and doses of the present invention can be useful for immunocompromised patients including, but not limited to cancer patients, HIV infected patients, and patients with an immunodegenerative disease. Furthermore, the methods can be useful for immunocompromised patients currently in a state of remission. The methods and doses of the present invention are also useful for patients undergoing other antiviral treatments. The prevention methods of the present invention are particularly useful for patients at risk of viral infection. These patients include, but are not limited to health care workers, e.g., doctors, nurses, hospice care givers; military personnel; teachers; childcare workers; patients traveling to, or living in, foreign locales, in particular third world locales including social aid workers, missionaries, and foreign diplomats. Finally, the methods and compositions include the treatment of refractory patients or patients resistant to treatment such as resistance to reverse transcriptase inhibitors, protease inhibitors, etc.

Doses

Toxicity and efficacy of the compounds of the invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$.

The data obtained from the cell culture assays and animal studies can be used in formulating a range of dosage of the compounds for use in humans. The dosage of such compounds lie preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture; alternatively, the dose of the Formula I compound may be formulated in animal models to achieve a circulating plasma concentration range of the compound that corresponds to the concentration required to achieve a fixed magnitude of response. Such information can be used to more accurately determine useful doses in humans. Levels in plasma may be measured, for example, by high performance liquid chromatography.

The protocols and compositions of the invention are preferably tested in vitro, and then in vivo, for the desired therapeutic or prophylactic activity, prior to use in humans. For example, in vitro assays which can be used to determine whether administration of a specific therapeutic protocol is indicated, include in vitro cell culture assays in which cells that are responsive to the effects of the Formula I compounds are exposed to the ligand and the magnitude of response is measured by an appropriate technique. The assessment of the Formula I compound is then evaluated with respect to the Formula I compound potency, and the degree of conversion of the Formula I compound prodrug. Compounds for use in methods of the invention can be tested in suitable animal model systems prior to testing in humans, including but not limited to in rats, mice, chicken, cows, monkeys, rabbits, hamsters, etc. The compounds can then be used in the appropriate clinical trials.

The magnitude of a prophylactic or therapeutic dose of a prodrug of a Formula I compound of the invention or a pharmaceutically acceptable salt, solvate, or hydrate thereof in the acute or chronic treatment or prevention of an infection or condition will vary with the nature and severity of the infection, and the route by which the active ingredient is administered. The dose, and perhaps the dose frequency, will also vary according to the infection to be treated, the age, body weight, and response of the individual patient. Suitable dosing regimens can be readily selected by those skilled in the art with due consideration of such factors. In one embodiment, the dose administered depends upon the specific compound to be used, and the weight and condition of the patient. Also, the dose may differ for various particular Formula I compounds; suitable doses can be predicted on the basis of the aforementioned in vitro measurements and on the basis of animal studies, such that smaller doses will be suitable for those Formula I compounds that show effectiveness at lower concentrations than other Formula I compounds when measured in the systems described or referenced herein. In general, the dose per day is in the range of from about 0.001 to 100 mg/kg, preferably about 1 to 25 mg/kg, more preferably about 5 to 15 mg/kg. For treatment of humans infected by hepatitis C viruses, about 0.1 mg to about 15 g per day is administered in about one to four divisions a day, preferably 100 mg to 12 g per day, more preferably from 100 mg to 8000 mg per day.

Additionally, the recommended daily dose ran can be administered in cycles as single agents or in combination with other therapeutic agents. In one embodiment, the daily dose is administered in a single dose or in equally divided doses. In a related embodiment, the recommended daily dose can be administered once time per week, two times per week, three times per week, four times per week or five times per week.

In one embodiment, the compounds of the invention are administered to provide systemic distribution of the compound within the patient. In a related embodiment, the compounds of the invention are administered to produce a systemic effect in the body.

In another embodiment the compounds of the invention are administered via oral, mucosal (including sublingual, buccal, rectal, nasal, or vaginal), parenteral (including subcutaneous, intramuscular, bolus injection, intraarterial, or intravenous), transdermal, or topical administration. In a specific embodiment the compounds of the invention are administered via mucosal (including sublingual, buccal, rectal, nasal, or vaginal), parenteral (including subcutaneous, intramuscular, bolus injection, intraarterial, or intravenous), transdermal, or topical administration. In a further specific embodiment, the compounds of the invention are administered via oral administration. In a further specific embodiment, the compounds of the invention are not administered via oral administration.

Different therapeutically effective amounts may be applicable for different infections, as will be readily known by those of ordinary skill in the art. Similarly, amounts sufficient to treat or prevent such infections, but insufficient to cause, or sufficient to reduce, adverse effects associated with conventional therapies are also encompassed by the above described dosage amounts and dose frequency schedules.

Combination Therapy

Specific methods of the invention further comprise the administration of an additional therapeutic agent (i.e., a therapeutic agent other than a compound of the invention). In certain embodiments of the present invention, the compounds of the invention can be used in combination with at least one other therapeutic agent. Therapeutic agents include, but are not limited to antibiotics, antiemetic agents, antidepressants, and antifungal agents, anti-inflammatory agents, antiviral agents, anticancer agents, immunomodulatory agents, α-interferons, β-interferons, ribavirin, alkylating agents, hormones, cytokines, or toll receptor-like modulators. In one embodiment the invention encompasses the administration of an additional therapeutic agent that is HCV specific or demonstrates anti-HCV activity.

The Formula I compounds of the invention can be administered or formulated in combination with antibiotics. For example, they can be formulated with a macrolide (e.g., tobramycin (Tobi®)), a cephalosporin (e.g., cephalexin (Keflex®), cephradine (Velosef®), cefuroxime (Ceftin®), cefprozil (Cefzil®), cefaclor (Ceclor®), cefixime (Suprax®) or cefadroxil (Duricef®)), a clarithromycin (e.g., clarithromycin (Biaxin®)), an erythromycin (e.g. erythromycin (EMycin®)), a penicillin (e.g., penicillin V (V-Cillin K® or Pen Vee K®)) or a quinolone (e.g., ofloxacin (Floxin®), ciprofloxacin (Cipro®) or norfloxacin (Noroxin®)), aminoglycoside antibiotics (e.g., apramycin, arbekacin, bambermycins, butirosin, dibekacin, neomycin, neomycin, undecylenate, netilmicin, paromomycin, ribostamycin, sisomicin, and spectinomycin), amphenicol antibiotics (e.g., azidamfenicol, chloramphenicol, florfenicol, and thiamphenicol), ansamycin antibiotics (e.g., rifamide and rifampin), carbacephems (e.g., loracarbef), carbapenems (e.g., biapenem and imipenem), cephalosporins (e.g., cefaclor, cefadroxil, cefamandole, cefatrizine, cefazedone, cefozopran, cefpimizole, cefpiramide, and cefpirome), cephamycins (e.g., cefbuperazone, cefmetazole, and cefminox), monobactams (e.g., aztreonam, carumonam, and tigemonam), oxacephems (e.g. flomoxef, and moxalactam), penicillins (e.g., amdinocillin, amdinocillin pivoxil, amoxicillin, bacampicillin, benzylpenicillinic acid, benzylpenicillin sodium, epicillin, fenbenicillin, floxacillin, penamccillin, penethamate hydriodide, penicillin o-benethamine, penicillin 0, penicillin V, penicillin V benzathine, penicillin V hydrabamine, penimepicycline, and phencihicillin potassium), lincosamides (e.g., clindamycin, and lincomycin), amphomycin, bacitracin, capreomycin, colistin, enduracidin, enviomycin, tetracyclines (e.g., apicycline, chlortetracycline, clomocycline, and demeclocycline), 2,4-diaminopyrimidines (e.g., brodimoprim), nitrofurans (e.g., furaltadone, and furazolium chloride), quinolones and analogs thereof (e.g., cinoxacin, clinafloxacin, flumequine, and grepagloxacin), sulfonamides (e.g., acetyl sulfamethoxypyrazine, benzylsulfamide, noprylsulfamide, phthalylsulfacetamide, sulfachrysoidine, and sulfacytine), sulfones (e.g., diathymosulfone, glucosulfone sodium, and solasulfone), cycloserine, mupirocin and tuberin.

The Formula I compounds of the invention can also be administered or formulated in combination with an antiemetic agent. Suitable antiemetic agents include, but are not limited to, metoclopromide, domperidone, prochlorperazine, promethazine, chlorpromazine, trimethobenzamide, ondansetron, granisetron, hydroxyzine, acethylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinols, thiethylperazine, thioproperazine, tropisetron, and mixtures thereof.

The Formula I compounds of the invention can be administered or formulated in combination with an antidepressant. Suitable antidepressants include, but are not limited to, binedaline, caroxazone, citalopram, dimethazan, fencamine, indalpine, indeloxazine hydrocholoride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimeldine.

The Formula I compounds of the invention can be administered or formulated in combination with an antifungal agent. Suitable antifungal agents include but are not limited to amphotericin B, itraconazole, ketoconazole, fluconazole, intrathecal, flucytosine, miconazole, butoconazole, clotrimazole, nystatin, terconazole, tioconazole, ciclopirox, econazole, haloprogrin, naftifine, terbinafine, undecylenate, and griseofulvin.

The Formula I compounds of the invention can be administered or formulated in combination with an anti-inflammatory agent. Useful anti-inflammatory agents include, but are not limited to, non-steroidal anti-inflammatory drugs such as salicylic acid, acetylsalicylic acid, methyl salicylate, diflunisal, salsalate, olsalazine, sulfasalazine, acetaminophen, indomethacin, sulindac, etodolac, mefenamic acid, meclofenamate sodium, tolmetin, ketorolac, dichlofenac, ibuprofen, naproxen, naproxen sodium, fenoprofen, ketoprofen, flurbinprofen, oxaprozin, piroxicam, meloxicam, ampiroxicam, droxicam, pivoxicam, tenoxicam, nabumetome, phenylbutazone, oxyphenbutazone, antipyrine, aminopyrine, apazone and nimesulide; leukotriene antagonists including, but not limited to, zileuton, aurothioglucose, gold sodium thiomalate and auranofin; steroids including, but not limited to, alclometasone diproprionate, amcinonide, beclomethasone dipropionate, betametasone, betamethasone benzoate, betamethasone diproprionate, betamethasone sodium phosphate, betamethasone valerate, clobetasol proprionate, clocortolone pivalate, hydrocortisone, hydrocortisone derivatives, desonide, desoximatasone, dexamethasone, flunisolide, flucoxinolide, flurandrenolide, halcinocide, medrysone, methylprednisolone, methprednisolone acetate, methylprednisolone sodium succinate, mometasone furoate, paramethasone acetate, prednisolone, prednisolone acetate, prednisolone sodium phosphate, prednisolone tebuatate, prednisone, triamcinolone, triamcinolone acetonide, triamcinolone diacetate, and triamcinolone hexacetonide; and other anti-inflammatory agents including, but not limited to, methotrexate, colchicine, allopurinol, probenecid, sulfinpyrazone and benzbromarone.

The Formula I compounds of the invention can be administered or formulated in combination with another antiviral agent. Useful antiviral agents include, but are not limited to, protease inhibitors, nucleoside reverse transcriptase inhibitors, non-nucleoside reverse transcriptase inhibitors and nucleoside analogs. The antiviral agents include but are not limited to zidovudine, acyclovir, gangcyclovir, vidarabine, idoxuridine, trifluridine, levovirin, viramidine and ribavirin, as well as foscarnet, amantadine, rimantadine, saquinavir, indinavir, amprenavir, lopinavir, ritonavir, the α-interferons; β-interferons; adefovir, clevadine, entecavir, pleconaril.

The Formula I compounds of the invention can be administered or formulated in combination with an immunomodulatory agent. Immunomodulatory agents include, but are not limited to, methothrexate, leflunomide, cyclophosphamide, cyclosporine A, mycophenolate mofetil, rapamycin (sirolimus), mizoribine, deoxyspergualin, brequinar, malononitriloamindes (e.g., leflunamide), T cell receptor modulators, and cytokine receptor modulators, peptide mimetics, and antibodies (e.g., human, humanized, chimeric, monoclonal, polyclonal, Fvs, ScFvs, Fab or F(ab)$_2$ fragments or epitope binding fragments), nucleic acid molecules (e.g., antisense nucleic acid molecules and triple helices), small molecules, organic compounds, and inorganic compounds. Examples of T cell receptor modulators include, but are not limited to, anti-T cell receptor antibodies (e.g., anti-CD4 antibodies (e.g., cM-T412 (Boehringer), IDEC-CE9.1® (IDEC and SKB), mAB 4162W94, Orthoclone and OKTcdr4a (Janssen-Cilag)), anti-CD3 antibodies (e.g., Nuvion (Product Design Labs), OKT3 (Johnson & Johnson), or Rituxan (IDEC)), anti-CD5 antibodies (e.g., an anti-CD5 ricin-linked immunoconjugate), anti-CD7 antibodies (e.g., CHH-380 (Novartis)), anti-CD8 antibodies, anti-CD40 ligand monoclonal antibodies (e.g., IDEC-131 (IDEC)), anti-CD52 antibodies (e.g., CAMPATH 1H (Ilex)), anti-CD2 antibodies, anti-CD11a antibodies (e.g., Xanelim (Genentech)), anti-B7 antibodies (e.g., IDEC-114 (IDEC)), CTLA4-immunoglobulin, and toll receptor-like (TLR) modulators. Examples of cytokine receptor modulators include, but are not limited to, soluble cytokine receptors (e.g., the extracellular domain of a TNF-α receptor or a fragment thereof, the extracellular domain of an IL-1β receptor or a fragment thereof, and the extracellular domain of an IL-6 receptor or a fragment thereof), cytokines or fragments thereof (e.g., interleukin (IL)-2, IL-3, IL-4, IL-5, IL-6, IL-7, IL-8, IL-9, IL-10, IL-11, IL-12, IL-15, TNF-α, interferon (IFN)-α, IFN-β, IFN-γ, and GM-CSF), anti-cytokine receptor antibodies (e.g., anti-IFN receptor antibodies, anti-IL-2 receptor antibodies (e.g., Zenapax (Protein Design Labs)), anti-IL-4 receptor antibodies, anti-IL-6 receptor antibodies, anti-IL-10 receptor antibodies, and anti-IL-12 receptor antibodies), anti-cytokine antibodies (e.g., anti-IFN antibodies, anti-TNF-α antibodies, anti-IL-1β antibodies, anti-IL-6 antibodies, anti-IL-8 antibodies (e.g., ABX-IL-8 (Abgenix)), and anti-IL-12 antibodies).

The Formula I compounds of the invention can be administered or formulated in combination with an agent which inhibits viral enzymes, including but not limited to inhibitors of HCV protease, such as BILN 2061, SCH-503034, ITMN-191 or VX-950; and inhibitors of NS5B polymerase such as NM107 (and its prodrug NM283), R1626, R7078, BILN1941, GSK625433, GILD9128 or HCV-796.

The Formula I compounds of the invention can be administered or formulated in combination with an agent which inhibits HCV polymerase such as those described in Wu, *Curr Drug Targets Infect Disord.*, 3, 207-19 (2003) or in combination with compounds that inhibit the helicase function of the virus such as those described in Bretner M., et al., *Nucleosides Nucleotides Nucleic Acids.*, 22, 1531 (2003), or with inhibitors of other HCV specific targets such as those described in Zhang X., *IDrugs*, 5(2), 154-8 (2002).

The Formula I compounds of the invention can be administered or formulated in combination with an agent which inhibits viral replication.

The Formula I compounds of the invention can be administered or formulated in combination with cytokines. Examples of cytokines include, but are not limited to, interleukin-2 (IL-2), interleukin-3 (IL-3), interleukin-4 (IL-4), interleukin-5 (IL-5), interleukin-6 (IL-6), interleukin-7 (IL-7), interleukin-9 (IL-9), interleukin-10 (IL-10), interleukin-12 (IL-12), interleukin 15 (IL-15), interleukin 18 (IL-18), platelet derived growth factor (PDGF), erythropoietin (Epo), epidermal growth factor (EGF), fibroblast growth factor (FGF), granulocyte macrophage stimulating factor (GM-CSF), granulocyte colony stimulating factor (G-CSF), macrophage colony stimulating factor (M-CSF), prolactin, and interferon (IFN), e.g., IFN-α, and IFN-γ).

The Formula I compounds of the invention can be administered or formulated in combination with hormones. Examples of hormones include, but are not limited to, luteinizing hormone releasing hormone (LHRH), growth hormone (GH), growth hormone releasing hormone, ACTH, somatostatin, somatotropin, somatomedin, parathyroid hormone, hypothalamic releasing factors, insulin, glucagon, enkephalins, vasopressin, calcitonin, heparin, low molecular weight heparins, heparinoids, synthetic and natural opioids, insulin thyroid stimulating hormones, and endorphins.

The Formula I compounds of the invention can be administered or formulated in combination with β-interferons which include, but are not limited to, interferon β-1a, interferon β-1b.

The Formula I compounds of the invention can be administered or formulated in combination with α-interferons which include, but are not limited to, interferon α-1, interferon α-2a (roferon), interferon α-2b, intron, Peg-Intron, Pegasys, consensus interferon (infergen) and albuferon.

The Formula I compounds of the invention can be administered or formulated in combination with an absorption enhancer, particularly those which target the lymphatic system, including, but not limited to sodium glycocholate; sodium caprate; N-lauryl-β-D-maltopyranoside; EDTA; mixed micelle; and those reported in Muranishi *Crit. Rev. Ther. Drug Carrier Syst.*, 7-1-33, which is hereby incorporated by reference in its entirety. Other known absorption enhancers can also be used. Thus, the invention also encompasses a pharmaceutical composition comprising one or more Formula I compounds of the invention and one or more absorption enhancers.

The Formula I compounds of the invention can be administered or formulated in combination with an alkylating agent. Examples of alkylating agents include, but are not limited to nitrogen mustards, ethylenimines, methylmelamines, alkyl sulfonates, nitrosoureas, triazenes, mechlorethamine, cyclophosphamide, ifosfamide, melphalan, chlorambucil, hexamethylmelaine, thiotepa, busulfan, carmustine, streptozocin, dacarbazine and temozolomide.

The compounds of the invention and the other therapeutics agent can act additively or, more preferably, synergistically. In one embodiment, a composition comprising a compound of the invention is administered concurrently with the administration of another therapeutic agent, which can be part of the same composition or in a different composition from that comprising the compounds of the invention. In another embodiment, a compound of the invention is administered prior to or subsequent to administration of another therapeutic agent. In a separate embodiment, a compound of the invention is administered to a patient who has not previously undergone or is not currently undergoing treatment with another therapeutic agent, particularly an antiviral agent.

In one embodiment, the methods of the invention comprise the administration of one or more Formula I compounds of the invention without an additional therapeutic agent.

Pharmaceutical Compositions and Dosage Forms

Pharmaceutical compositions and single unit dosage forms comprising a Formula I compound of the invention, or a pharmaceutically acceptable salt, or hydrate thereof, are also encompassed by the invention. Individual dosage forms of the invention may be suitable for oral, mucosal (including sublingual, buccal, rectal, nasal, or vaginal), parenteral (including subcutaneous, intramuscular, bolus injection, intraarterial, or intravenous), transdermal, or topical administration. Pharmaceutical compositions and dosage forms of the invention typically also comprise one or more pharmaceutically acceptable excipients. Sterile dosage forms are also contemplated.

In an alternative embodiment, pharmaceutical composition encompassed by this embodiment includes a Formula I compound of the invention, or a pharmaceutically acceptable salt, or hydrate thereof, and at least one additional therapeutic agent. Examples of additional therapeutic agents include, but are not limited to, those listed above.

The composition, shape, and type of dosage forms of the invention will typically vary depending on their use. For example, a dosage form used in the acute treatment of a disease or a related disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease or disorder. These and other ways in which specific dosage forms encompassed by this invention will vary from one another will be readily apparent to those skilled in the art. See, e.g., *Remington's Pharmaceutical Sciences*, 18th ed., Mack Publishing, Easton Pa. (1990). Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

Typical pharmaceutical compositions and dosage forms comprise one or more carriers, excipients or diluents. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Carstensen, *Drug Stability: Principles & Practice*, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms of the invention comprise Formula I compounds of the invention, or a pharmaceutically acceptable salt or hydrate thereof comprise 0.1 mg to 1500 mg per unit to provide doses of about 0.01 to 200 mg/kg per day.

Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences,* 18th ed., Mack Publishing, Easton Pa. (1990).

Typical oral dosage forms of the invention are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Delayed Release Dosage Forms

Active ingredients of the invention can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry and/or lyophylized products ready to be dissolved or suspended in a pharmaceutically acceptable vehicle for injection (reconstitutable powders), suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

Transdermal Dosage Forms

Transdermal dosage forms include "reservoir type" or "matrix type" patches, which can be applied to the skin and worn for a specific period of time to permit the penetration of a desired amount of active ingredients.

Suitable excipients (e.g. carriers and diluents) and other materials that can be used to provide transdermal and topical dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof.

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Topical Dosage Forms

Topical dosage forms of the invention include, but are not limited to, creams, lotions, ointments, gels, solutions, emulsions, suspensions, or other forms known to one of skill in the art. See, e.g. *Remington's Pharmaceutical Sciences*, 18th eds., Mack Publishing, Easton Pa. (1990); and *Introduction to Pharmaceutical Dosage Forms*, 4th ed., Lea & Febiger, Philadelphia (1985).

Suitable excipients (e.g. carriers and diluents) and other materials that can be used to provide transdermal and topical dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof.

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

Mucosal Dosage Forms

Mucosal dosage forms of the invention include, but are not limited to, ophthalmic solutions, sprays and aerosols, or other forms known to one of skill in the art. See, e.g., *Remington's Pharmaceutical Sciences,* 18th eds., Mack Publishing, Easton Pa. (1990); and *Introduction to Pharmaceutical Dosage Forms,* 4th ed., Lea & Febiger, Philadelphia (1985). Dosage forms suitable for treating mucosal tissues within the oral cavity can be formulated as mouthwashes or as oral gels. In one embodiment, the aerosol comprises a carrier. In another embodiment, the aerosol is carrier free.

The Formula I compounds of the invention may also be administered directly to the lung by inhalation. For administration by inhalation, a Formula I compound can be conveniently delivered to the lung by a number of different devices. For example, a Metered Dose Inhaler ("MDI") which utilizes canisters that contain a suitable low boiling propellant, e.g., dichlorodifluoromethane, trichlorofluoromethane, dichlorotetrafluoroethane, carbon dioxide or other suitable gas can be used to deliver a Formula I compound directly to the lung. MDI devices are available from a number of suppliers such as 3M Corporation, Aventis, Boehringer Ingleheim, Forest Laboratories, Glaxo-Wellcome, Schering Plough and Vectura.

Alternatively, a Dry Powder Inhaler (DPI) device can be used to administer a Formula I compound to the lung (see, e.g., Raleigh et al., *Proc. Amer. Assoc. Cancer Research Annual Meeting,* 1999, 40, 397, which is herein incorporated by reference). DPI devices typically use a mechanism such as a burst of gas to create a cloud of dry powder inside a container, which can then be inhaled by the patient. DPI devices are also well known in the art and can be purchased from a number of vendors which include, for example, Fisons, Glaxo-Wellcome, Inhale Therapeutic Systems, ML Laboratories, Qdose and Vectura. A popular variation is the multiple dose DPI ("MDDPI") system, which allows for the delivery of more than one therapeutic dose. MDDPI devices are available from companies such as AstraZeneca, GlaxoWellcome, IVAX, Schering Plough, SkyePharma and Vectura. For example, capsules and cartridges of gelatin for use in an inhaler or insufflator can be formulated containing a powder mix of the compound and a suitable powder base such as lactose or starch for these systems.

Another type of device that can be used to deliver a Formula I compound to the lung is a liquid spray device supplied, for example, by Aradigm Corporation. Liquid spray systems use extremely small nozzle holes to aerosolize liquid drug formulations that can then be directly inhaled into the lung.

In one embodiment, a nebulizer device is used to deliver a Formula I compound to the lung. Nebulizers create aerosols from liquid drug formulations by using, for example, ultrasonic energy to form fine particles that can be readily inhaled (See e.g., Verschoyle et al., *British J Cancer,* 1999, 80, Suppl 2, 96, which is herein incorporated by reference). Examples of nebulizers include devices supplied by Sheffield/Systemic Pulmonary Delivery Ltd. (See, Armer et al., U.S. Pat. No. 5,954,047; van der Linden et al., U.S. Pat. No. 5,950,619; van der Linden et al., U.S. Pat. No. 5,970,974, which are herein incorporated by reference), Aventis and Batelle Pulmonary Therapeutics.

In one embodiment, an electrohydrodynamic ("EHD") aerosol device is used to deliver Formula I compounds to the lung. EHD aerosol devices use electrical energy to aerosolize liquid drug solutions or suspensions (see, e.g., Noakes et al., U.S. Pat. No. 4,765,539; Coffee, U.S. Pat. No., 4,962,885; Coffee, PCT Application, WO 94/12285; Coffee, PCT Application, WO 94/14543; Coffee, PCT Application, WO 95/26234, Coffee, PCT Application, WO 95/26235, Coffee, PCT Application, WO 95/32807, which are herein incorporated by reference). The electrochemical properties of the Formula I compounds formulation may be important parameters to optimize when delivering this drug to the lung with an EHD aerosol device and such optimization is routinely performed by one of skill in the art. EHD aerosol devices may more efficiently delivery drugs to the lung than existing pulmonary delivery technologies. Other methods of intra-pulmonary delivery of Formula I compounds will be known to the skilled artisan and are within the scope of the invention.

Liquid drug formulations suitable for use with nebulizers and liquid spray devices and EHD aerosol devices will typically include a Formula I compound with a pharmaceutically acceptable carrier. Preferably, the pharmaceutically acceptable carrier is a liquid such as alcohol, water, polyethylene glycol or a perfluorocarbon. Optionally, another material may be added to alter the aerosol properties of the solution or suspension of the Formula I compound. Preferably, this material is liquid such as an alcohol, glycol, polyglycol or a fatty acid. Other methods of formulating liquid drug solutions or suspension suitable for use in aerosol devices are known to those of skill in the art (see, e.g., Biesalski, U.S. Pat. Nos. 5,112,598; Biesalski, 5,556,611, which are herein incorporated by reference) A Formula I compound can also be formulated in rectal or vaginal compositions such as suppositories or retention enemas, e.g. containing conventional suppository bases such as cocoa butter or other glycerides.

In addition to the formulations described previously, a Formula I compound can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Alternatively, other pharmaceutical delivery systems can be employed. Liposomes and emulsions are well known examples of delivery vehicles that can be used to deliver Formula I compounds. Certain organic solvents such as dimethylsulfoxide can also be employed, although usually at the cost of greater toxicity. A Formula I compound can also be delivered in a controlled release system. In one embodiment, a pump can be used (Sefton, *CRC Crit. Ref Biomed Eng.,* 1987, 14, 201; Buchwald et al., *Surgery,* 1980, 88, 507; Saudek et al., *N. Engl. J. Med.,* 1989, 321, 574). In another embodiment, polymeric materials can be used (see *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger and Peppas, *J. Macromol. Sci. Rev. Macromol. Chem.,* 1983, 23, 61; see also Levy et al., *Science,* 1985, 228, 190; During et al., *Ann. Neurol.,* 1989, 25, 351; Howard et al., *J. Neurosurg.,* 71, 105

(1989). In yet another embodiment, a controlled-release system can be placed in proximity of the target of the compounds of the invention, e.g., the lung, thus requiring only a fraction of the systemic dose (see, e.g., Goodson, in *Medical Applications of Controlled Release*, supra, vol. 2, pp. 115 (1984)). Other controlled-release system can be used (see, e.g., Langer, *Science,* 1990, 249, 1527).

Suitable excipients (e.g., carriers and diluents) and other materials that can be used to provide mucosal dosage forms encompassed by this invention are well known to those skilled in the pharmaceutical arts, and depend on the particular site or method which a given pharmaceutical composition or dosage form will be administered. With that fact in mind, typical excipients include, but are not limited to, water, ethanol, ethylene glycol, propylene glycol, butane-1,3-diol, isopropyl myristate, isopropyl palmitate, mineral oil, and mixtures thereof, which are non-toxic and pharmaceutically acceptable. Examples of such additional ingredients are well known in the art. See, e.g, *Remington's Pharmaceutical Sciences,* 18th eds., Mack Publishing, Easton Pa. (1990).

The pH of a pharmaceutical composition or dosage form, or of the tissue to which the pharmaceutical composition or dosage form is applied, can also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Kits

The invention provides a pharmaceutical pack or kit comprising one or more containers comprising a Formula I compound useful for the treatment or prevention of a Hepatitis C virus infection. In other embodiments, the invention provides a pharmaceutical pack or kit comprising one or more containers comprising a Formula I compound useful for the treatment or prevention of a Hepatitis C virus infection and one or more containers comprising an additional therapeutic agent, including but not limited to those listed above, in particular an antiviral agent, an interferon, an agent which inhibits viral enzymes, or an agent which inhibits viral replication, preferably the additional therapeutic agent is HCV specific or demonstrates anti-HCV activity.

The invention also provides a pharmaceutical pack or kit comprising one or more containers comprising one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The inventive agents may be prepared using the reaction routes and synthesis schemes as described below, employing the general techniques known in the art using starting materials that are readily available. The synthesis of non-exemplified compounds according to the invention may be successfully performed by modifications apparent to those skilled in the art, e.g., by appropriately protecting interfering groups, by changing to other suitable reagents known in the art, or by making routine modifications of reaction conditions. Alternatively, other reactions disclosed herein or generally known in the art will be recognized as having applicability for preparing other compounds of the invention.

Preparation of Compounds

In the synthetic schemes described below, unless otherwise indicated all temperatures are set forth in degrees Celsius and all parts and percentages are by weight.

Reagents were purchased from commercial suppliers such as Aldrich Chemical Company or Lancaster Synthesis Ltd. and were used without further purification unless otherwise indicated. All solvents were purchased from commercial suppliers such as Aldrich, EMD Chemicals or Fisher and used as received.

The reactions set forth below were done generally under a positive pressure of argon or nitrogen at an ambient temperature (unless otherwise stated) in anhydrous solvents, and the reaction flasks were fitted with rubber septa for the introduction of substrates and reagents via syringe. Glassware was oven dried and/or heat dried.

The reactions were assayed by TLC and/or analyzed by LC-MS and terminated as judged by the consumption of starting material. Analytical thin layer chromatography (TLC) was performed on glass-plates precoated with silica gel 60 $F_{254}$ 0.25 mm plates (EMD Chemicals), and visualized with UV light (254 nm) and/or iodine on silica gel and/or heating with TLC stains such as ethanolic phosphomolybdic acid, ninhydrin solution, potassium permanganate solution or ceric sulfate solution. Preparative thin layer chromatography (prepTLC) was performed on glass-plates precoated with silica gel 60 $F_{254}$ 0.5 mm plates (20×20 cm, from Thomson Instrument Company) and visualized with UV light (254 nm).

Work-ups were typically done by doubling the reaction volume with the reaction solvent or extraction solvent and then washing with the indicated aqueous solutions using 25% by volume of the extraction volume unless otherwise indicated. Product solutions were dried over anhydrous $Na_2SO_4$ and/or $MgSO_4$ prior to filtration and evaporation of the solvents under reduced pressure on a rotary evaporator and noted as solvents removed in vacuo. Column chromatography was completed under positive pressure using Merck silica gel 60, 230-400 mesh or 50-200 mesh neutral alumina, ISCO Flash-chromatography using prepacked RediSep silica gel columns, or Analogix flash column chromatography using pre-packed SuperFlash silica gel columns. Hydrogenolysis was done at the pressure indicated in the examples or at ambient pressure.

$^1$H-NMR spectra and $^{13}$C-NMR were recorded on a Varian Mercury-VX400 instrument operating at 400 MHz. NMR spectra were obtained as $CDCl_3$ solutions (reported in ppm), using chloroform as the reference standard (7.27 ppm for the proton and 77.00 ppm for carbon), $CD_3OD$ (3.4 and 4.8 ppm for the protons and 49.3 ppm for carbon), DMSO-$d_6$ (2.49 ppm for proton), or internally tetramethylsilane (0.00 ppm) when appropriate. Other NMR solvents were used as needed. When peak multiplicities are reported, the following abbreviations are used: s (singlet), d (doublet), t (triplet), q (quartet), m (multiplet), br (broadened), bs (broad singlet), dd (doublet of doublets), dt (doublet of triplets). Coupling constants, when given, are reported in Hertz (Hz).

Infrared (IR) spectra were recorded on an ATR FT-IR Spectrometer as neat oils or solids, and when given are reported in wave numbers ($cm^{-1}$). Mass spectra reported are (+)-ES or APCI (+) LC/MS conducted by the Analytical Chemistry Department of Anadys Pharmaceuticals, Inc. Elemental analyses were conducted by the Atlantic Microlab, Inc. in Norcross, Ga. or by NuMega Resonance Labs, Inc. in San Diego, Calif. Melting points (mp) were determined on an open capillary apparatus, and are uncorrected.

The described synthetic pathways and experimental procedures may utilize many common chemical abbreviations, 2,2-DMP (2,2-dimethoxypropane), Ac (acetyl), ACN (acetonitrile), Aliquat® 336 (trioctylmethylammonium chloride), Bn (benzyl), BnOH (benzyl alcohol), Boc (tert-butoxycarbonyl), Boc$_2$O (di-tert-butyl dicarbonate), Bz (benzoyl), CSI (chlorosulfonyl isocyanate), DAST (diethylaminosulfur trifluoride), DBU (1,8-diazabicyclo[5,4,0]undec-7-ene), DCC (N,N'-dicyclohexylcarbodiimide), DCE (1,2-dichloroethane), DCM (dichloromethane), DEAD (diethylazodicarboxylate), DIEA (diisopropylethylamine), DMA (N,N-dimethylacetamide), DMAP (4-(N,N-dimethylamino)pyridine), DMF (N,N-dimethylformamide), DMSO (dimethyl sulfoxide), EDC (1-(3-dimethylaminopropyl)-3-ethylcarbodiimide hydrochloride), Et (ethyl), EtOAc (ethyl acetate), EtOH (ethanol), Et$_2$O (diethyl ether), HATU (O-(7-azabenzotriazol-1-yl)-1,1,3,3-tetramethyluronium hexafluorophosphate), HBTU (O-benzotriazol-1-yl-N,N,N',N'-tetramethyluronium hexafluorophosphate), HF (hydrogen fluoride), HOAc (acetic acid), HOBT (1-hydroxybenzotriazole hydrate), HPLC (high pressure liquid chromatography), iPrOH (isopropyl alcohol), IPA (isopropyl alcohol), KHMDS (potassium bis(trimethylsilyl)amide), KN(TMS)$_2$ (potassium bis(trimethylsilyl)amide), KO$^t$Bu (potassium tert-butoxide), KOH (potassium hydroxide), LDA (lithium diisopropylamine), MCPBA (3-chloroperbenzoic acid), Me (methyl), MeCN (acetonitrile), MeOH (methanol), MTBE (methyl tert-butyl ether), NaCNBH$_3$ (sodium cyanoborohydride), NaH (sodium hydride), NaN(TMS)$_2$ (sodium bis(trimethylsilyl)amide), NaOAc (sodium acetate), NaOEt (sodium ethoxide), NIS (N-iodosuccinimide), Phe (phenylalanine), PPTS (pyridinium p-toluenesulfonate), PS (polymer supported), Py (pyridine), pyBOP (benzotriazol-1-yloxy)tripyrrolidinophosphonium hexafluorophosphate), TEA (triethylamine), TFA (trifluoroacetic acid), TFAA (trifluoroacetic anhydride), THF (tetrahydrofuran), TLC (thin layer chromatography), Tol (toluoyl), Val (valine), and the like.

Scheme 1 provides a general procedure that was used to prepare 3-(1,1-dioxobenzo[1,2,4]thiadiazine)-pyrrolo[1,2-b]pyridazin-2-one compounds of Formula I.

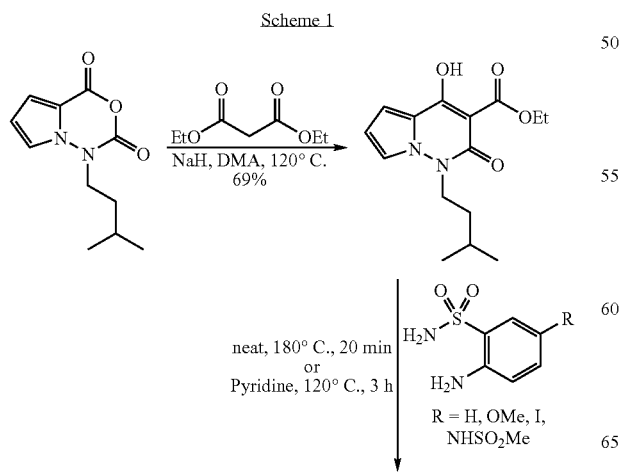

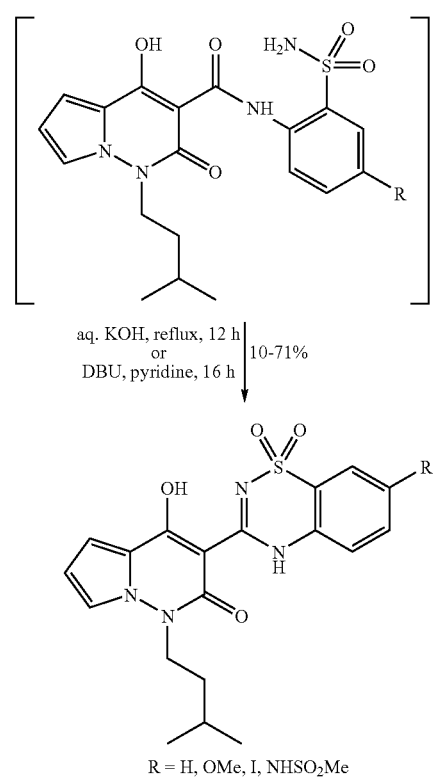

The cyclic anhydride intermediate, which can be obtained as described below, can be condensed with a dialkylmalonate in the presence of a strong base, such as sodium hydride, to yield the shown ester. The ester can be fused together with an ortho-amino sulfonamide compound to form the amide, which can be cyclized in the presence of a base (e.g., aq. KOH) to give the desired 3-(1,1-dioxobenzo[1,2,4]thiadiazine)-pyrrolo[1,2-b]pyridazin-2-one compounds.

Scheme 2 provides a general procedure that can be used to prepare the cyclic anhydride intermediates.

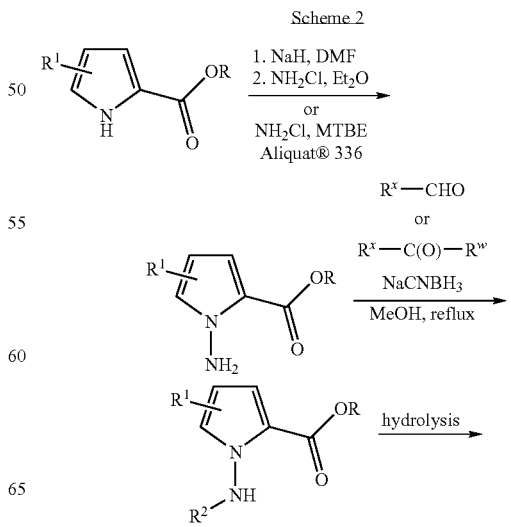

-continued

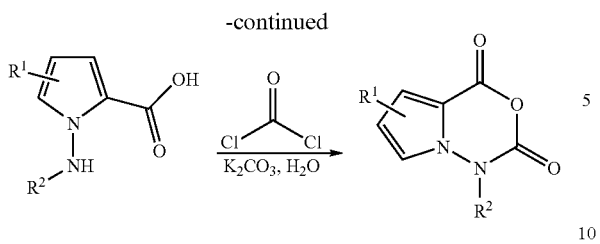

Commercially available pyrrole-2-carboxylic acid esters (alternatively, the commercially available acid can be protected as a suitable ester using standard methods for ester formation) can be N-aminated using monochloroamine to yield the hydrazine intermediates. These entities can be N-alkylated by reacting them with aldehydes or ketones, where $R^x$ and $R^w$ are $C_1$-$C_5$ alkyl, $C_3$-$C_8$ cycloalkyl, —$C_1$-$C_5$ alkylene($C_3$-$C_8$ cycloalkyl), —$C_1$-$C_5$ alkylene(aryl), —$C_1$-$C_5$ alkylene(heterocyclyl), aryl, or heterocyclyl, or $R^w$ can combine with $R^x$ to form a 3- to 8-membered ring, and a reducing agent, such as sodium cyanoborohydride. Deprotection of the esters followed by cyclization using phosgene or phosgene equivalents gives the desired cyclic anhydride intermediates.

Scheme 3 provides a procedure that was used to prepare the 4-(3-methyl-butyl)-6-oxa-3a,4-diaza-indene-5,7-dione intermediate.

Scheme 3

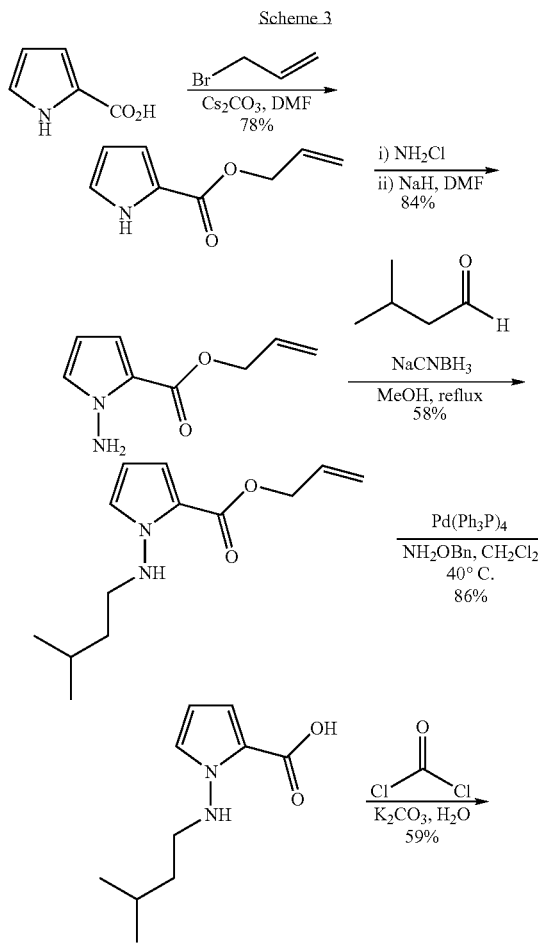

-continued

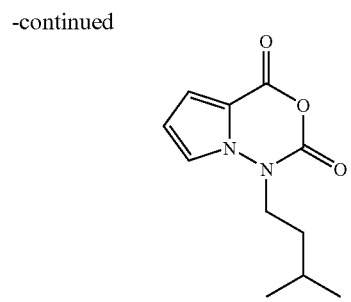

Pyrrole-2-carboxylic acid can be protected as an ester (e.g., allyl ester) using standard methods for ester formation. The ring nitrogen can be N-aminated using monochloroamine to yield the hydrazine intermediate, which can be N-alkylated with an aldehyde using know methods of reductive amination. Deprotection of the ester followed by cyclization using phosgene or phosgene equivalents can be used to give the desired 4-(3-methyl-butyl)-6-oxa-3a,4-diaza-indene-5,7-dione intermediate.

Schemes 4(a) and 4(b) provide general procedures that were used to prepare the 2-amino-5-methanesulfonylamino-benzenesulfonamide intermediate.

Scheme 4(a)

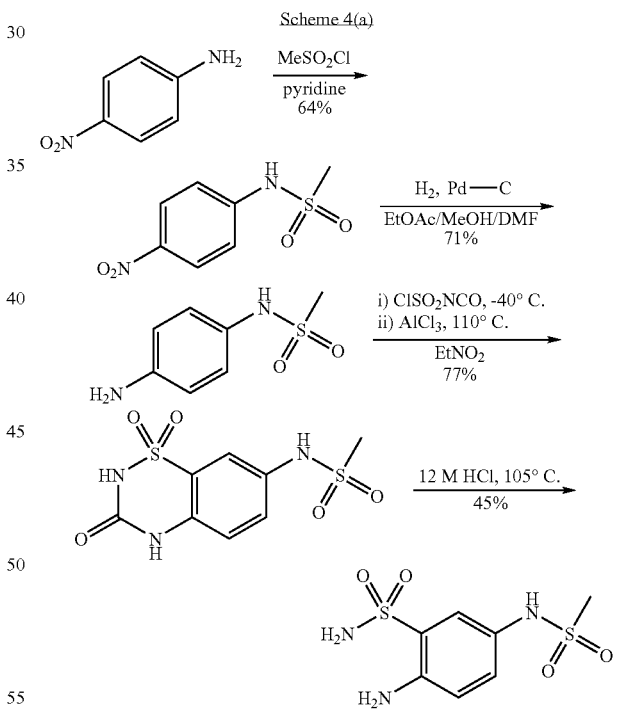

Commercially available 4-nitroaniline can be treated with sulfonyl chlorides, e.g., methanesulfonyl chloride, to obtain the corresponding sulfonamides. Reduction of the nitro group using standard conditions affords the corresponding anilines, which can be treated with chlorosulfonyl isocyanate followed by aluminum chloride to give the corresponding 1,1-dioxo-1,4-dihydro-2H-1$\lambda^6$-benzo[1,2,4]thiadiazin-3-ones. Opening of the cyclic ureas with a strong acid (e.g., hydrochloric acid) gives the desired 2-amino-5-sulfonylamino-benzenesulfonamide intermediates.

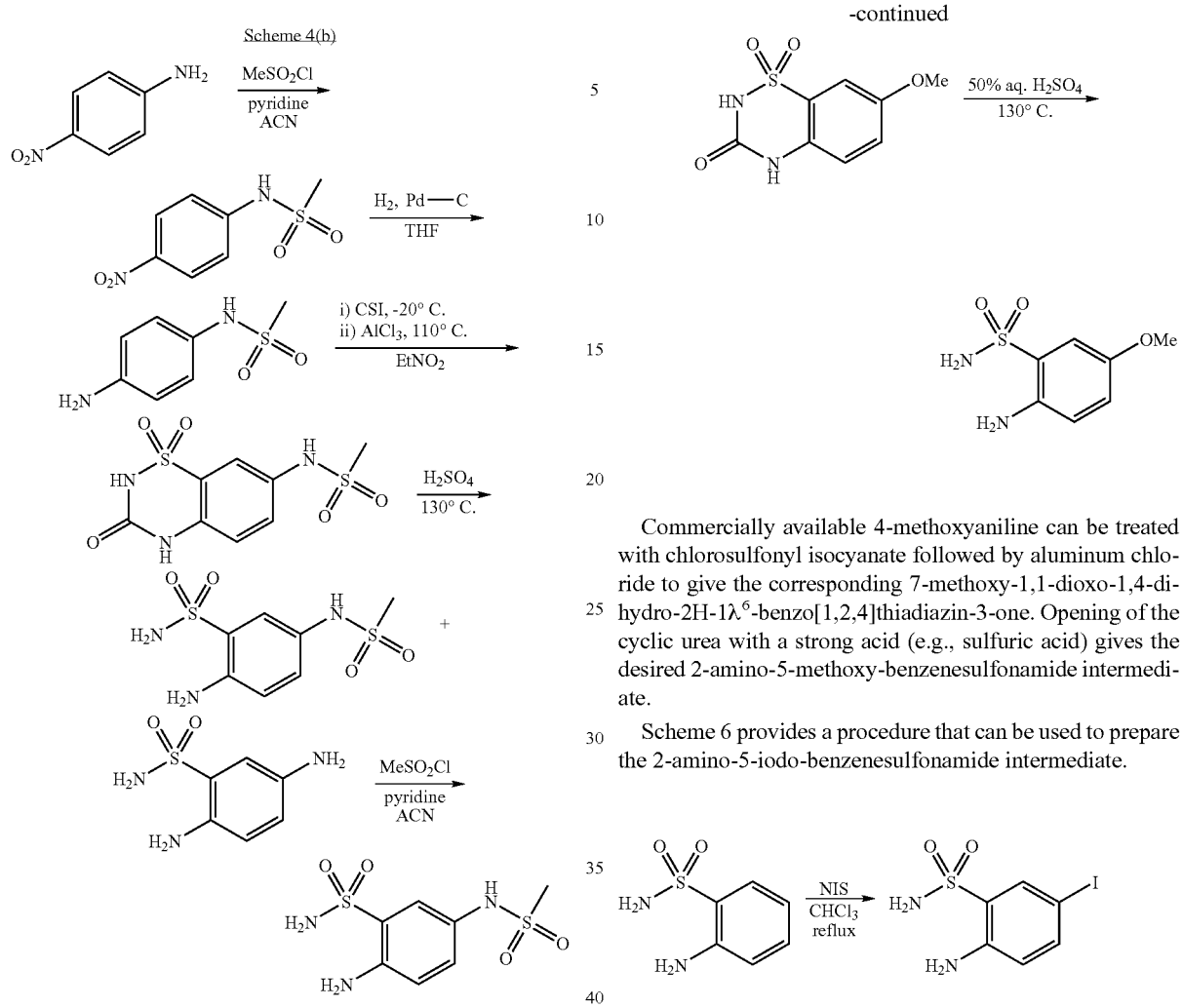

In a preferred route, commercially available 4-nitroaniline can be treated with sulfonyl chlorides, e.g., methanesulfonyl chloride, to obtain the corresponding sulfonamides. Reduction of the nitro group using standard conditions affords the corresponding anilines, which can be treated with chlorosulfonyl isocyanate followed by aluminum chloride to give the corresponding 1,1-dioxo-1,4-dihydro-2H-1$\lambda^6$-benzo[1,2,4]thiadiazin-3-ones. Opening of the cyclic ureas with a strong acid (e.g., sulfuric acid) gives the desired 2-amino-5-sulfonylamino-benzenesulfonamide intermediates along with some of the hydrolyzed 2,5-diaminobenzenesulfonamide, which can be converted back by treatment with sulfonyl chlorides, e.g., methanesulfonyl chloride, to obtain the desired 2-amino-5-sulfonylamino-benzenesulfonamide intermediates.

Scheme 5 provides a procedure that can be used to prepare the 2-amino-5-methoxy-benzenesulfonamide intermediate.

Scheme 5

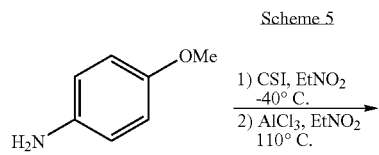

Commercially available 4-methoxyaniline can be treated with chlorosulfonyl isocyanate followed by aluminum chloride to give the corresponding 7-methoxy-1,1-dioxo-1,4-dihydro-2H-1$\lambda^6$-benzo[1,2,4]thiadiazin-3-one. Opening of the cyclic urea with a strong acid (e.g., sulfuric acid) gives the desired 2-amino-5-methoxy-benzenesulfonamide intermediate.

Scheme 6 provides a procedure that can be used to prepare the 2-amino-5-iodo-benzenesulfonamide intermediate.

Commercially available 2-amino-benzensulfonamide can be treated with N-iodosuccinimide to give the desired 2-amino-5-iodo-benzenesulfonamide intermediate.

Scheme 7 provides an alternative general procedure that was used to prepare 3-(1,1-dioxobenzo[1,2,4]thiadiazine)-pyrrolo[1,2-b]pyridazin-2-one compounds of Formula I.

Scheme 7

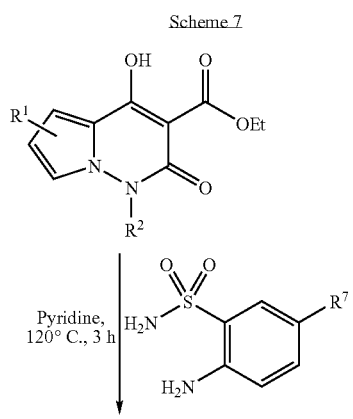

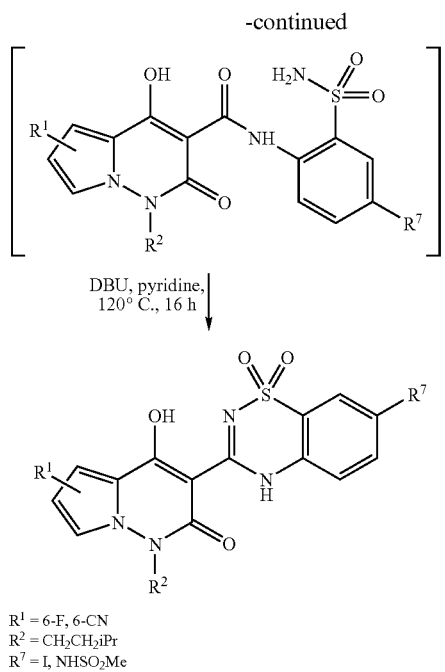

R¹ = 6-F, 6-CN
R² = CH₂CH₂iPr
R⁷ = I, NHSO₂Me

The 1-substituted 4-hydroxy-2-oxo-1,2-dihydro-pyrrolo[1,2-b]pyridazine-3-carboxylic acid ester intermediates can be fused together neat or in a suitable solvent (e.g., pyridine) with optionally substituted ortho-amino sulfonamide compounds to form the corresponding amides. The amide intermediates can be cyclized (without prior isolation) in the presence of a base (e.g., DBU) to give the desired 3-(1,1-dioxobenzo[1,2,4]thiadiazine)-pyrrolo[1,2-b]pyridazin-2-one compounds.

Scheme 8 provides a general procedure that can be used to prepare 1-substituted 6-fluoro-4-hydroxy-2-oxo-1,2-dihydro-pyrrolo[1,2-b]pyridazine-3-carboxylic acid ethyl ester intermediates.

Scheme 8

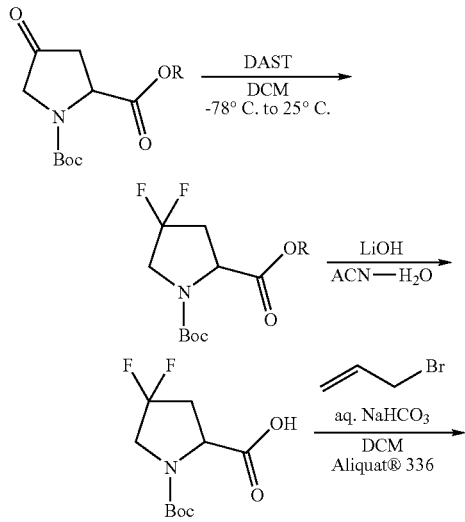

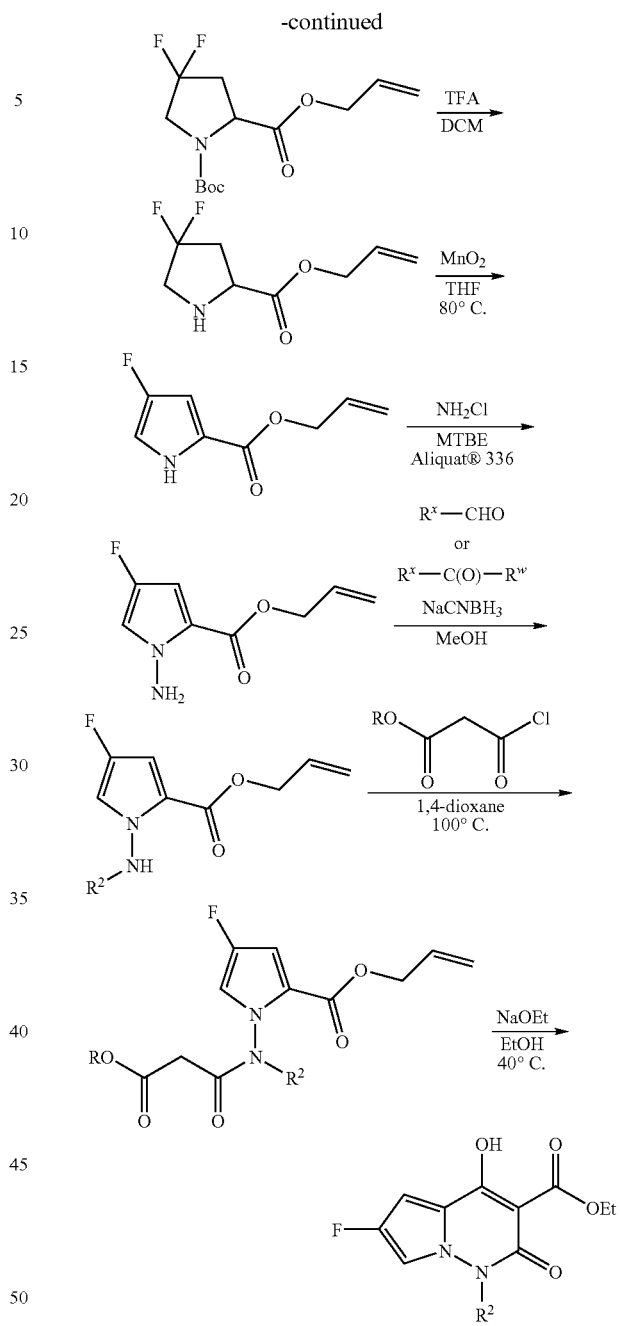

Commercially available 4-oxo-pyrrolidine-1,2-dicarboxylic acid 1-tert-butyl ester 2-methyl ester can be treated with a fluorinating agent, such as DAST, to afford the corresponding difluoro intermediates. Hydrolysis of the ester gives the acid, which can then be transformed into a suitable ester (such as an allyl ester) using standard conditions. Removal of the protecting group under standard conditions gives the free amine. Subsequent oxidation with an oxidizing agent (e.g., manganese dioxide) leads to the corresponding pyrrole intermediate. N-Amination with monochloramine affords the hydrazine intermediate, which can be N-alkylated by treatment with aldehydes or ketones, where $R^x$ and $R^w$ are $C_1$-$C_5$ alkyl, $C_3$-$C_8$ cycloalkyl, —$C_1$-$C_5$ alkylene($C_3$-$C_8$ cycloalkyl), —$C_1$-$C_5$ alkylene(aryl), —$C_1$-$C_5$ alkylene(heterocyclyl), aryl, or heterocyclyl, or R$^w$ can combine with R$^x$ to form a 3- to 8-membered ring, and a reducing agent, such as sodium cyanoborohydride. Acylation of the nitrogen with a malonyl chlorides (e.g., methyl malonyl chloride) gives the corresponding hydrazides, which can be cyclized in the presence of a base (e.g., sodium ethoxide) to give the desired 1-substituted 6-fluoro-4-hydroxy-2-oxo-1,2-dihydro-pyrrolo[1,2-b]pyridazine-3-carboxylic acid ethyl ester intermediates.

Scheme 9 provides a general procedure that can be used to prepare 1-substituted 6-cyano-4-hydroxy-2-oxo-1,2-dihydro-pyrrolo[1,2-b]pyridazine-3-carboxylic acid ethyl ester intermediates.

ment with aldehydes or ketones, where R$^x$ and R$^w$ are C$_1$-C$_5$ alkyl, C$_3$-C$_8$ cycloalkyl, —C$_1$-C$_5$ alkylene(C$_3$-C$_8$ cycloalkyl), —C$_1$-C$_5$ alkylene(aryl), —C$_1$-C$_5$ alkylene(heterocyclyl), aryl, or heterocyclyl, or R$^w$ can combine with R$^x$ to form a 3- to 8-membered ring, and a reducing agent, such as sodium cyanoborohydride. Acylation of the nitrogen with a malonyl chloride monoester (such as methyl malonyl chloride) gives the corresponding hydrazides, which can be cyclized in the presence of a base (e.g., sodium ethoxide) to give the desired 1-substituted 6-cyano-4-hydroxy-2-oxo-1,2-dihydro-pyrrolo[1,2-b]pyridazine-3-carboxylic acid ethyl ester intermediates.

Scheme 10 provides an alternative general procedure that was used to prepare 3-(1,1-dioxobenzo[1,2,4]thiadiazine)-pyrrolo[1,2-b]pyridazin-2-one compounds of Formula I

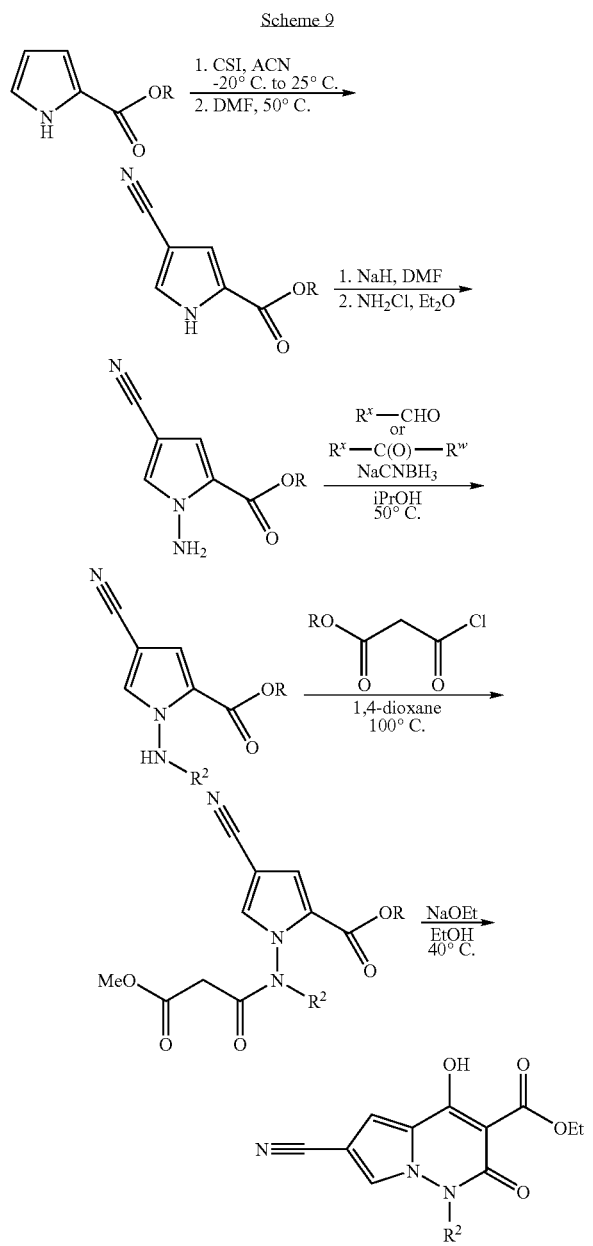

Scheme 9

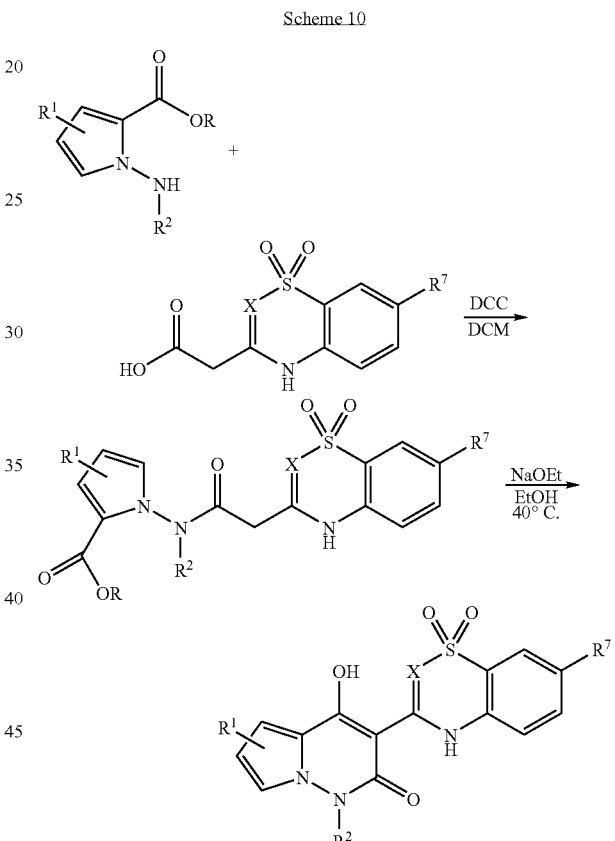

Scheme 10

R = OMe
R$^1$ = H
R$^2$ = CH$_2$CH$_2$iPr, CH$_2$CH$_2$tBu, 4-F-Bn, 3-Cl-4-F-Bn
R$^7$ = I, NHSO$_2$Me, NMeSO$_2$Me
X = N, CH

A 1H-pyrrole-2-carboxylic acid ester, such as a methyl ester, can be treated with chlorosulfonyl isocyanate (CSI) followed by N,N-dimethylformamide to introduce the cyano moiety. N-Amination with monochloramine affords the hydrazine intermediates, which can be N-alkylated by treat- The 1-substituted-1-amino-1H-pyrrole-2-carboxylic acid esters (e.g., methyl esters), which can be prepared as described in schemes 2, 3, 8, and 9, can be coupled with acid intermediates using standard peptide coupling conditions, such as DCC, to afford the corresponding amide intermediates. Treatment of these entities with a base (e.g., sodium ethoxide) gives the desired 3-(1,1-dioxobenzo[1,2,4]thiadiazine)-pyrrolo[1,2-b]pyridazin-2-one compounds of Formula I.

Scheme 11 provides a general procedure that can be used to prepare 7-substituted-1,1-dioxo-1,4-dihydro-1λ$^6$-benzo[1,2,4]thiadiazin-3-yl-acetic acid intermediates.

Scheme 11

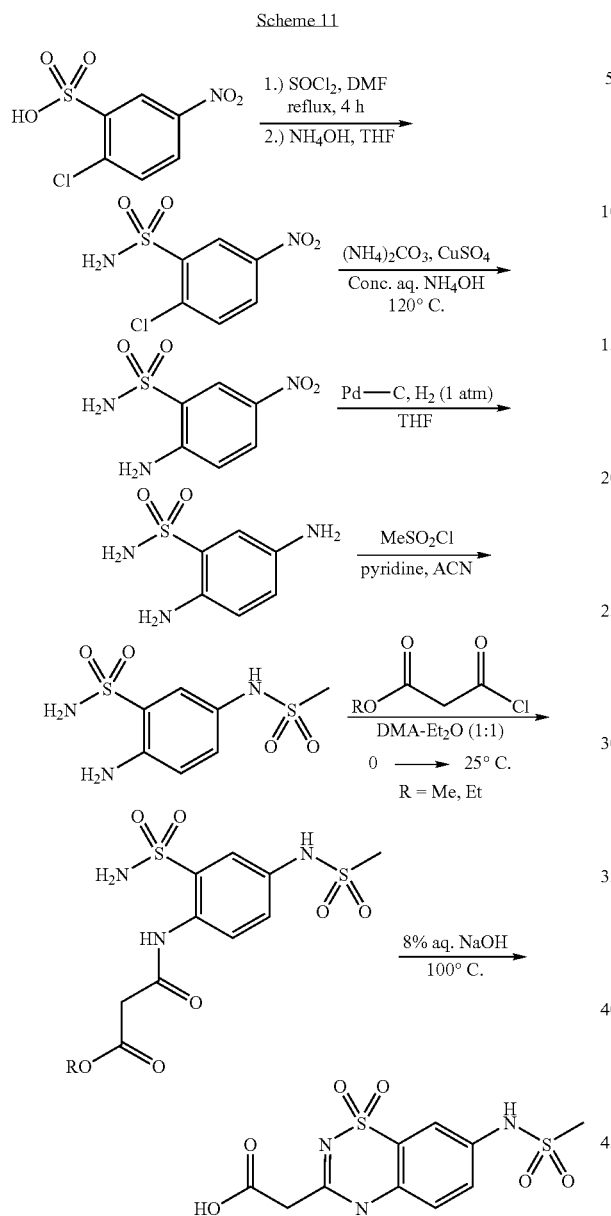

Commercially available 2-chloro-5-nitro-benzenesulfonic acid can be treated with thionyl chloride to give the sulfonylchloride, which can be further treated with ammonia to afford the sulfonamide intermediate. The chloride can be displaced with ammonia by treatment with ammonium hydroxide and ammonium carbonate in the presence of copper(II) sulfate. Reduction of the nitro group under standard hydrogenation conditions affords the aniline intermediate, which can be treated with a sulfonyl chloride, such as methylsulfonyl chloride, to yield the corresponding sulfonamide. Acylation of the 2-amino moiety with malonyl chlorides, e.g., ethyl 3-chloro-3-oxo-propionate, gives the corresponding amide, which can simultaneously be cyclized to the thiadiazine-dioxide and hydrolyzed to the desired acid intermediate.

Scheme 12 provides an alternative procedure that can be used to prepare the 2-chloro-5-nitro-benzenesulfonamide intermediate.

Scheme 12

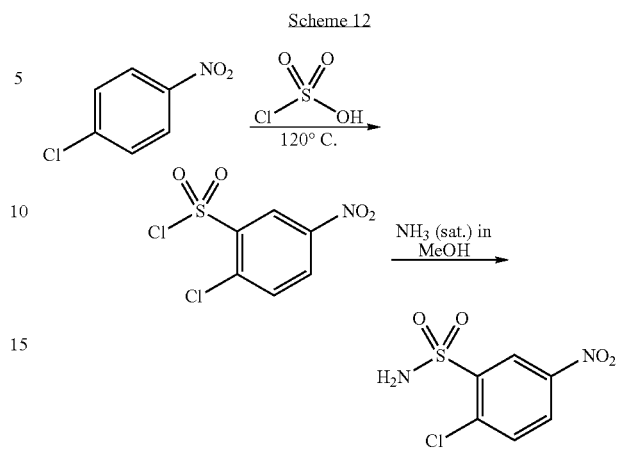

Commercially available 1-chloro-4-nitro-benzene can be reacted with chlorosulfonic acid to afford the corresponding sulfonylchloride. Treatment with a saturated solution of ammonia in methanol affords the desired the 2-chloro-5-nitro-benzenesulfonamide intermediate.

Scheme 13 provides an alternative procedure that can be used to prepare the 2,5-diamino-benzenesulfonamide intermediate.

Scheme 13

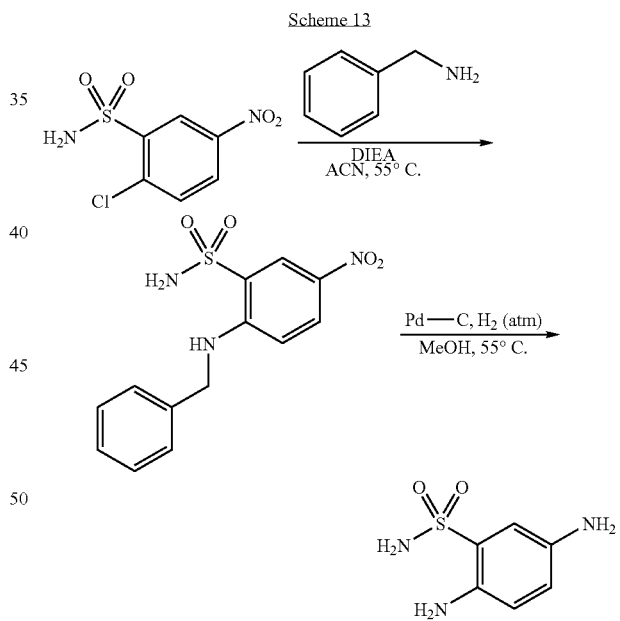

The 2-chloro-5-nitro-benzenesulfonamide intermediate (prepared as described in schemes 11 and 12) can be treated with a benzylic amine, such as benzyl amine, to displace the chloro moiety. Hydrogenation under standard conditions can be used to remove the benzylic group and to reduce the nitro group at the same time to afford the desired 2,5-diamino-benzenesulfonamide intermediate.

Scheme 14 provides an alternative procedure that can be used to prepare the 2-amino-5-nitro-benzenesulfonamide intermediate.

Scheme 14

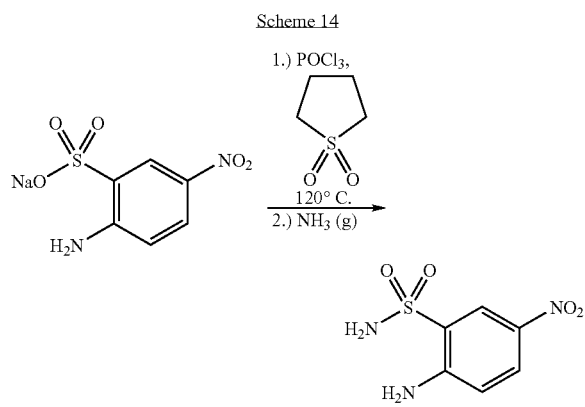

The commercially available sodium salt of 2-amino-5-nitro-benzenesulfonic acid can be converted to the corresponding sulfonyl chloride with phosphoryl chloride in the presence of a suitable co-solvent, such as sulfolane. Treatment with ammonia, e.g., ammonia solution in methanol or ammonia gas, affords the desired 2-amino-5-nitro-benzenesulfonamide intermediate.

Scheme 15 provides an alternative procedure that can be used to prepare the 2-amino-5-nitro-benzenesulfonamide intermediate.

Scheme 15

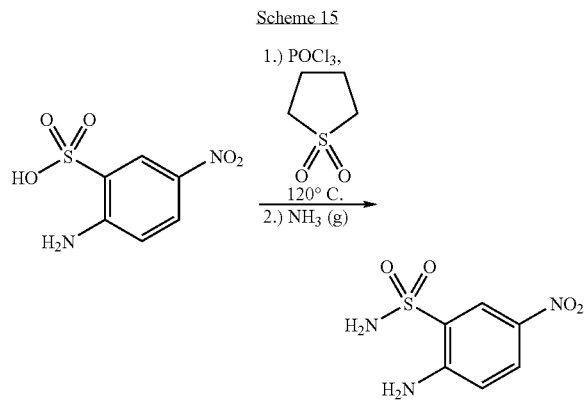

Commercially available 2-amino-5-nitro-benzenesulfonic acid can be converted to the corresponding sulfonyl chloride with phosphoryl chloride in the presence of a suitable co-solvent, such as sulfolane. Treatment with ammonia, e.g., aqueous ammonium hydroxide solution or ammonia gas, affords the desired 2-amino-5-nitro-benzenesulfonamide intermediate.

Scheme 16 provides an alternative procedure that can be used to prepare the N-(4-methanesulfonylamino-2-sulfamoyl-phenyl)-malonamic acid ethyl ester intermediate.

Scheme 16

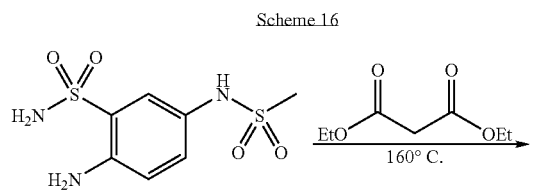

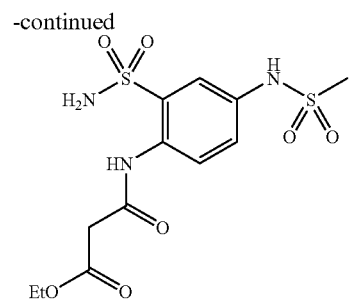

2-Amino-5-methanesulfonylamino-benzenesulfonamide (prepared as described in schemes 4 and 12) can be treated with a dialkyl malonate, such as diethyl malonate, to afford the desired N-(4-methanesulfonylamino-2-sulfamoyl-phenyl)-malonamic acid ethyl ester intermediate.

Scheme 17 provides a general procedure that can be used to prepare the (7-iodo-1,1-dioxo-1,4-dihydro-1$\lambda^6$-benzo[1,2,4]thiadiazin-3-yl)-acetic acid intermediate.

Scheme 17

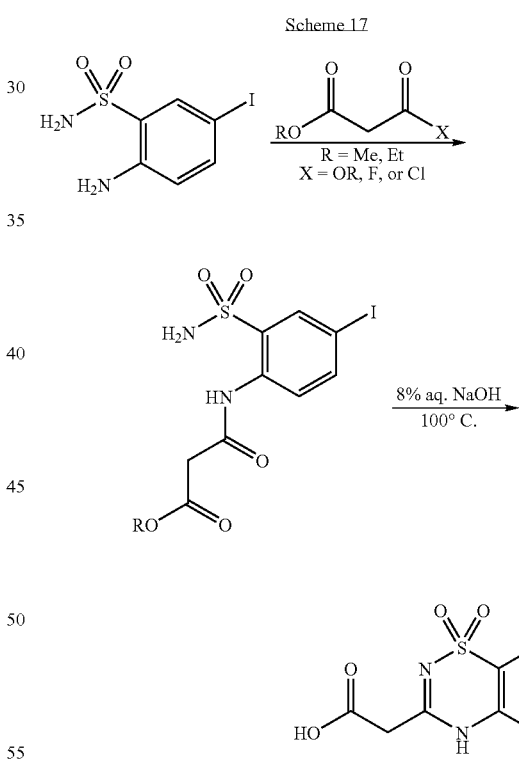

Acylation of 2-amino-5-iodo-benzenesulfonamide with a malonyl halide monoester, such as ethyl 3-chloro-3-oxo-propionate, or with a dialkyl malonate, such as diethyl malonate, affords the corresponding amide, which can simultaneously be cyclized to the thiadiazine-dioxide and hydrolyzed to the desired acid intermediate.

Scheme 18 provides a general procedure that can be used to prepare the 3-(1,1-dioxobenzo[1,2,4]thiadiazine)-pyrrolo[1,2-b]pyridazin-2-one compounds of Formula I from the corresponding iodo precursors.

Scheme 18

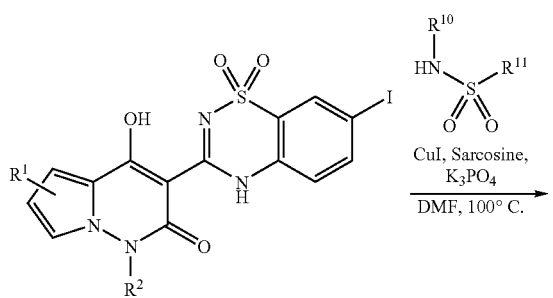

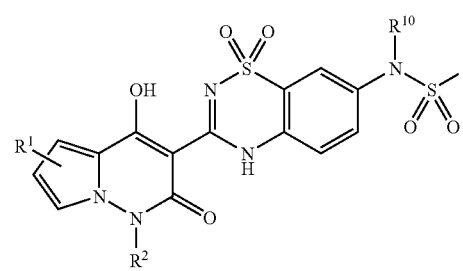

Optionally substituted 4-hydroxy-3-(7-iodo-1,1-dioxo-1,4-dihydro-1λ⁶-benzo[1,2,4]thiadiazin-3-yl)-pyrrolo[1,2-b]pyridazin-2-ones can be treated with substituted sulfonamides in a copper-mediated displacement reaction to afford the desired 3-(1,1-dioxobenzo[1,2,4]thiadiazine)-pyrrolo[1,2-b]pyridazin-2-one compounds of Formula I.

Scheme 19 provides a general procedure that can be used to prepare the 3-(1,1-dioxobenzo[1,2,4]thiadiazine)-pyrrolo[1,2-b]pyridazin-2-one compounds of Formula I from the corresponding iodo precursors.

Scheme 19

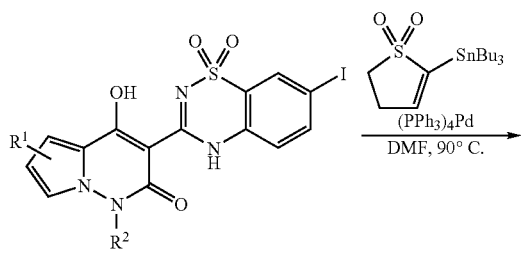

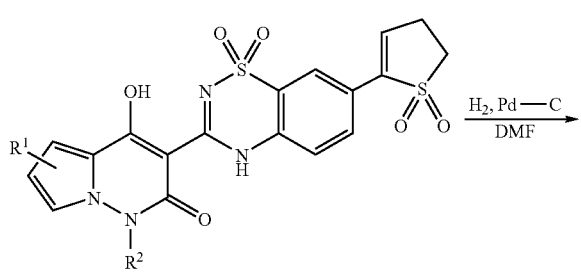

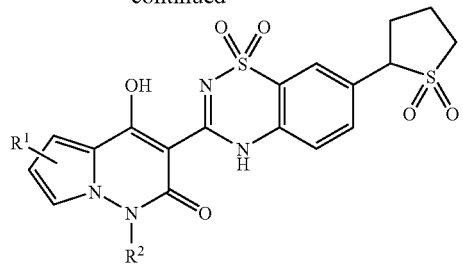

-continued

Optionally substituted 4-hydroxy-3-(7-iodo-1,1-dioxo-1,4-dihydro-1λ⁶-benzo[1,2,4]thiadiazin-3-yl)-pyrrolo[1,2-b]pyridazin-2-ones can be treated with stannanes, such as the unsaturated cyclic sulfone shown above, in a Stille-type palladium-catalyzed reaction to afford the unsaturated intermediates shown. Reduction of the alkene using standard hydrogenation conditions affords the desired 3-(1,1-dioxobenzo[1,2,4]thiadiazine)-pyrrolo[1,2-b]pyridazin-2-one compounds of Formula I.

Scheme 20 provides a general procedure that can be used to prepare 3-(1,1-dioxobenzo[1,4]thiazin)-pyrrolo[1,2-b]pyridazin-2-one compounds of Formula I.

Scheme 20

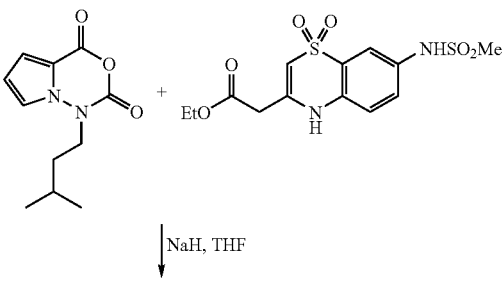

The cyclic anhydride and (7-methanesulfonylamino-1,1-dioxo-1,4-dihydro-1λ⁶-benzo[1,4]thiazin-3-yl)-acetic acid ethyl ester intermediate can be condensed in the presence of a base (e.g., sodium hydride) to yield the desired 3-(1,1-dioxobenzo[1,4]thiazin)-pyrrolo[1,2-b]pyridazin-2-one compound.

Scheme 21 provides a procedure that can be used to prepare the (7-methanesulfonylamino-1,1-dioxo-1,4-dihydro-1λ⁶-benzo[1,4]thiazin-3-yl)-acetic acid ethyl ester intermediate.

Scheme 21

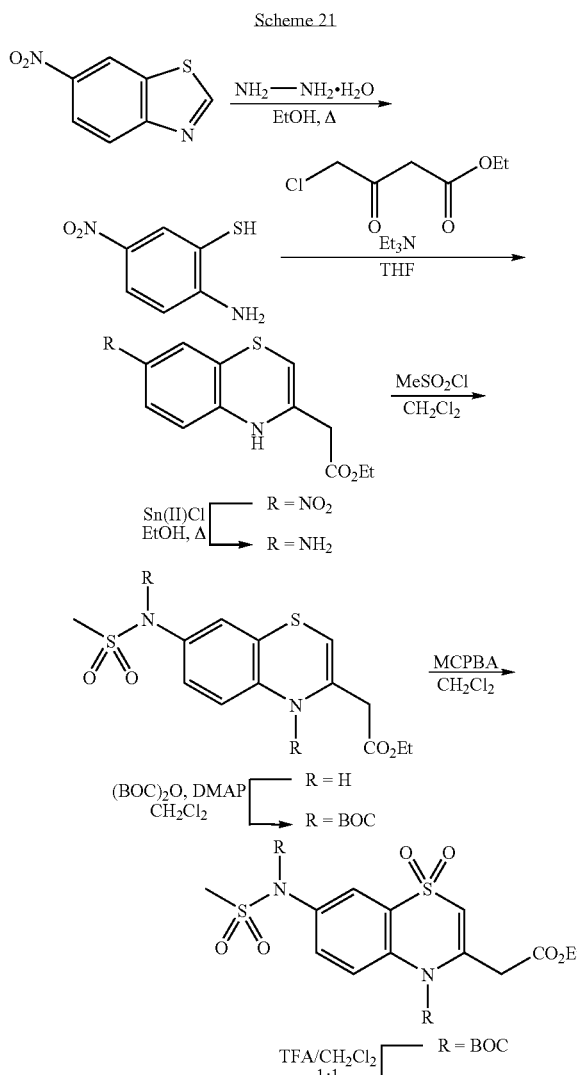

Scheme 22

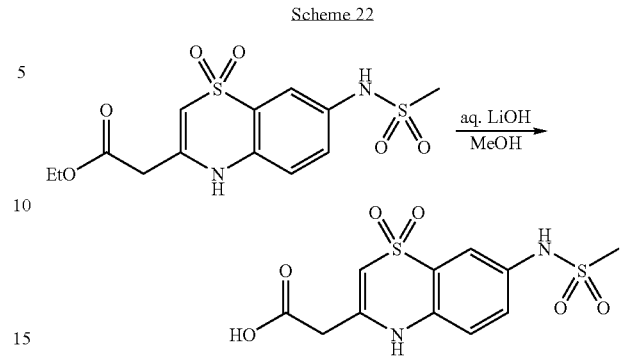

Hydrolysis of the 7-substituted-1,1-dioxo-1,4-dihydro-1λ⁶-benzo[1,4]thiazin-3-yl-acetic acid ester can be accomplished using standard conditions (e.g., lithium hydroxide) to afford the desired (7-methanesulfonylamino-1,1-dioxo-1,4-dihydro-1λ⁶-benzo[1,4]thiazin-3-yl)-acetic acid intermediate.

Scheme 23 provides a general procedure that can be used to prepare 7-(N-methyl)-substituted-1,1-dioxo-1,4-dihydro-1λ⁶-benzo[1,4]thiazin-3-yl-acetic acid intermediate.

Scheme 23

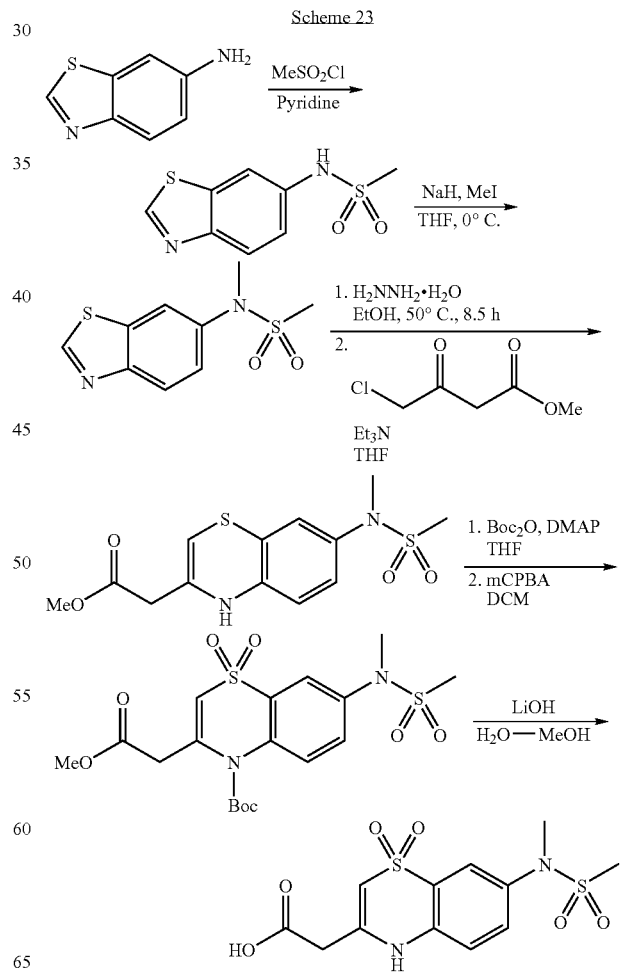

Commercially available 6-nitrobenzothiazole can be treated with hydrazine to obtain the 2-amino-5-nitro-benzenethiol, which can subsequently be reacted with chloroacetoacetate to give the (7-nitro-4H-benzo[1,4]thiazin-3-yl)-acetic acid ethyl ester. Reduction of the nitro group to the amino group can be accomplished by reaction with tin(II) chloride. Subsequent reaction with methansulfonyl chloride can be used to obtain the corresponding sulfonamide. Protection of both nitrogens with a suitable protecting group such as a Boc group can be achieved by using standard methods for protecting amino groups. The sulfide can be oxidized using a suitable oxidizing reagent (e.g., MCPBA) to give the sulfone. Finally, deprotection of the amino groups using trifluoroacetic acid can be used to afford the desired (7-methanesulfonylamino-1,1-dioxo-1,4-dihydro-1λ⁶-benzo[1,4]thiazin-3-yl)-acetic acid ethyl ester intermediate.

Scheme 22 provides a general procedure that can be used to prepare 7-substituted-1,1-dioxo-1,4-dihydro-1λ⁶-benzo[1,4]thiazin-3-yl-acetic acid intermediates.

Commercially available 6-aminobenzothiazole can be treated with a sulfonyl chloride, such as methanesulfonyl chloride, to obtain the corresponding sulfonamides. Reaction with methyl iodide, in the presence of a base, gives the corresponding N-methyl sulfonamide. Reaction with hydrazine hydrate and subsequent treatment with methyl chloroacetoacetate affords the corresponding 4H-benzo[1,4]thiazin-3-yl)-acetic acid methyl ester. Protection of the ring nitrogen with a suitable protecting group such as a Boc group can be achieved by using standard methods for protecting amino groups. The sulfide can be oxidized using a suitable oxidizing reagent (e.g., MCPBA) to give the sulfone. Finally, hydrolysis of the ester affords the desired [7-(methanesulfonyl-methyl-amino)-1,1-dioxo-1,4-dihydro-1$\lambda^6$-benzo[1,4]thiazin-3-yl]-acetic acid intermediate.

EXAMPLE 1

3-(1,1-Dioxo-1,4-dihydro-1$\lambda^6$-benzo[1,2,4]thiadi-azin-3-yl)-4-hydroxy-1-(3-methyl-butyl)-pyrrolo[1,2-b]pyridazin-2-one

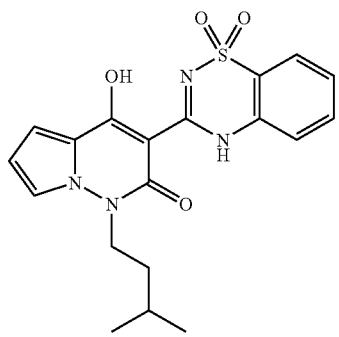

a) 1H-Pyrrole-2-carboxylic acid allyl ester

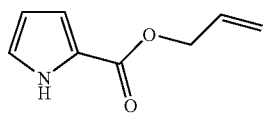

To a solution of 1H-pyrrole-2-carboxylic acid (1.5 g, 14 mmol) in N,N-dimethylformamide (50 mL) at 25° C. was added cesium carbonate (4.8 g, 14.7 mmol) and allyl bromide (1.34 mL, 15.4 mmol) and stirred for 16 h. The reaction mixture was treated with saturated aqueous ammonium chloride solution and diethyl ether (20 mL). The layers were separated and the aqueous layers were extracted with diethyl ether (3×100 mL). The combined organic layers were dried over magnesium sulfate, filtered and concentrated in vacuo to afford the crude desired product, 1H-pyrrole-2-carboxylic acid allyl ester (1.6 g, 10.6 mmol, 76% yield) as a yellow oil, which was used in the next step without further purification. $^1$H NMR (400 MHz, CDCl$_3$) δ 4.77 (1H, m), 5.35 (1H, dd, $J_1$=10.4 Hz, $J_2$=1.2 Hz), 5.39 (1H, dd, $J_1$=16.8 Hz, $J_2$=1.6 Hz), 6.26 (1H, m), 5.96 (1H, m), 6.94 (2H, m), 9.2 (1H, bs).

b) 1-Amino-1H-pyrrole-2-carboxylic acid allyl ester

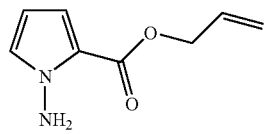

To a solution of 1H-pyrrole-2-carboxylic acid allyl ester (Example 1a, 0.75 g, 4.96 mmol) in N,N-dimethylformamide (20 mL) at 25° C. was added sodium hydride (0.316 g, 7.29 mmol) and stirred for 1 h. A solution of monochloroamine (36 mL, 7.19 mmol) in diethyl ether (0.2 M) was added and stirred for 1 h and then treated with saturated aqueous sodium bicarbonate solution (50 mL) and water (25 mL). The layers were separated and the aqueous layer was extracted with diethyl ether (3×50 mL). The combined organic layers were dried over magnesium sulfate, filtered and concentrated in vacuo to afford the crude desired product, 1-amino-1H-pyrrole-2-carboxylic acid allyl ester (0.90 g) as a yellow oil, which was used in the next step without further purification. $^1$H NMR (400 MHz, CDCl$_3$) δ 4.75 (2H, m), 5.28 (1H, dd, $J_1$=10.0 Hz, $J_2$=1.2 Hz), 5.40 (1H, dd, $J_1$=17.2 Hz, $J_2$=1.6 Hz), 6.03-5.90 (2H, m), 6.87 (1H, dd, $J_1$=4.0 Hz, $J_2$=1.6 Hz), 6.97 (1H, t, J=2.0 Hz).

Alternatively, 1-amino-1H-pyrrole-2-carboxylic acid allyl ester can be prepared as follows:

1H-Pyrrole-2-carboxylic acid allyl ester (Example 1a, 11.73 g, 78.12 mmol) was dissolved in methyl tert-butyl ether (150 mL) and a solution of sodium hydroxide (37 g, 925 mmol) in water (150 mL) was added. Solid ammonium chloride (25.1 g, 469 mmol), trioctylmethylammonium chloride ("Aliquat® 336", 1 mL) and 28% aqueous ammonium hydroxide solution (50 mL) were added to the biphasic mixture. Under vigorous stirring, a 6.15% aqueous bleach solution ("Chlorox", 250 mL) was slowly added over a period of 45 min via addition funnel upon which the color of the solution turned orange. After stirring for 1.5 h at 25° C., mixture was poured into methyl tert-butyl ether (150 mL) and the layers were separated. The organic layer was washed with a solution of sodium thiosulfate (10 g) in water (200 mL) and the organic layer was dried over sodium sulfate and filtered. The solvent was removed in vacuo to afford the desired product, 1-amino-1H-pyrrole-2-carboxylic acid allyl ester (8.03 g, 48.32 mmol, 62% yield) as a brown oil.

c) 1-(3-Methyl-butylamino)-1H-pyrrole-2-carboxylic acid allyl ester

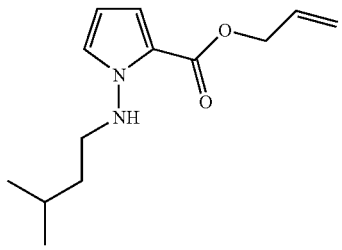

To a solution of 1-amino-1H-pyrrole-2-carboxylic acid allyl ester (Example 1b, 0.88 g, 5.3 mmol) in methanol (12 mL) was added isovaleryl aldehyde (0.74 mL, 6.9 mmol) and 1 drop 10% aqueous hydrochloric acid. The reaction mixture was stirred at 25° C. for 20 min, after which sodium cyanoborohydride (0.201 g, 3.2 mmol) was added and the resulting yellow solution was heated at reflux for 16 h. The reaction was quenched slowly with 10% aqueous hydrochloric acid and concentrated in vacuo. The crude slurry was redissolved in diethyl ether. The layers were separated and the aqueous layer was extracted with diethyl ether. The combined organic layers were dried over magnesium sulfate, filtered and concentrated in vacuo. The crude product was purified by column chromatography (Merck silica gel 60, 40-63 μm, ethyl acetate/hexane, 20-40%) to afford the desired product, 1-(3-methyl-butylamino)-1H-pyrrole-2-carboxylic acid allyl ester (0.70 g, 2.96 mmol, 60% yield) as a yellow oil. $^1$H NMR (400 MHz, CDCl$_3$) δ 0.92 (6H, d, J=6.8 Hz), 1.42 (2H, q, $J_1$=14.4 Hz, $J_2$=7.2 Hz), 1.68 (1H, m), 3.03 (2H, t, J=7.2 Hz), 4.76 (2H, d, J=5.6 Hz), 5.28 (1H, d, J=9.6 Hz), 5.40 (1H, d, J=17.2 Hz), 6.01-6.04 (2H, m), 6.89-6.90 (1H, m), 6.96-6.97 (1H, m).

d) 1-(3-Methyl-butylamino)-1H-pyrrole-2-carboxylic acid

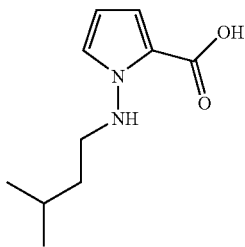

To a solution of 1-(3-methyl-butylamino)-1H-pyrrole-2-carboxylic acid allyl ester (Example 1c, 2.8 g, 16 mmol) in dichloromethane (70 mL) was added O-benzylhydroxylamine hydrochloride (2.56 g, 16 mmol). Tetrakis(triphenylphosphine)palladium(0) (3.6 g, 3.2 mmol) was added and the reaction mixture was heated at reflux for 16 h. The crude mixture was allowed to cool to 25° C. The solvent was removed in vacuo and redissolved in ethyl acetate (150 mL) and then washed with 10% aqueous hydrochloric acid solution (3×50 mL) and water (50 mL). The organic layer was dried over magnesium sulfate, filtered and concentrated in vacuo. The crude product was purified by column chromatography (Merck silica gel 60, 40-63 μm, ethyl acetate/hexane, 20-60%) to afford the desired product, 1-(3-methyl-butylamino)-1H-pyrrole-2-carboxylic acid (2.5 g, 13 mmol, 82% yield) as a yellow oil. $^1$H NMR (400 MHz, CDCl$_3$) δ 0.94 (6H, d, J=6.4 Hz), 1.41-1.47 (2H, q, J=15.2 Hz, $J_2$=6.8 Hz), 1.68 (1H, m), 6.18 (1H, dd, $J_1$=4.0 Hz, $J_2$=2.8 Hz), 6.98-7.02 (2H, m).

(e) 4-(3-Methyl-butyl)-6-oxa-3a,4-diaza-indene-5,7-dione

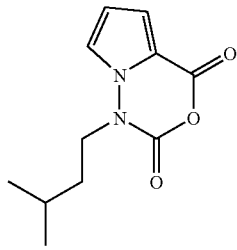

To a solution of 1-(3-methyl-butylamino)-1H-pyrrole-2-carboxylic acid (Example 1d, 0.25 g, 1.27 mmol) in water (2 mL) was added potassium carbonate (0.175 g, 1.27 mmol). The reaction mixture was cooled to 0° C. and phosgene (20% solution in toluene) (0.95 mL, 1.91 mmol) was slowly added dropwise. The resulting yellow solution was stirred for 16 h. Ethyl acetate (4 mL) was added and the layers were separated. The aqueous layer was extracted with ethyl acetate (3×5 mL). The combined organic layers were dried over magnesium sulfate, filtered and concentrated in vacuo. The crude product was purified by column chromatography (Merck silica gel 60, 40-63 μm, ethyl acetate/hexane, 20-50%) to afford the desired product, 4-(3-methyl-butyl)-6-oxa-3a,4-diaza-indene-5,7-dione (0.16 g, 0.72 mmol, 57% yield) as a tan solid. $^1$H NMR (400 MHz, DMSO-d$_6$) δ 0.93 (6H, d, J=6.8 Hz), 1.56 (2H, m), 1.65 (1H, m), 4.16 (2H, t, J=7.2 Hz), 6.50 (1H, m), 7.08 (1H, m), 7.70 (1H, m).

(f) 4-Hydroxy-1-(3-methyl-butyl)-2-oxo-1,2-dihydro-pyrrolo[1,2-b]pyridazine-3-carboxylic acid ethyl ester

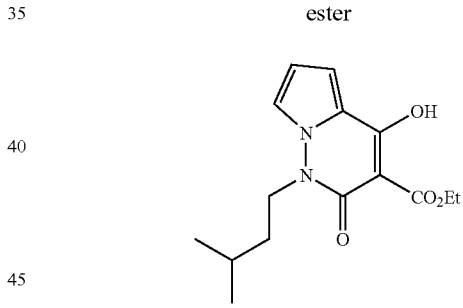

To a solution of 4-(3-methyl-butyl)-6-oxa-3a,4-diaza-indene-5,7-dione (Example 1e, 0.080 g, 0.36 mmol) and diethyl malonate (0.58 mL, 3.6 mmol) in N,N-dimethylacetamide (1 mL) was added sodium hydride (0.017 g, 0.43 mmol) and 1 drop of methanol. The reaction mixture was heated to 120° C. and stirred for 16 h. The reaction was allowed to cool to 25° C. and quenched with saturated aqueous ammonium chloride solution and ethyl acetate. The layers were separated and the aqueous layer was extracted with ethyl acetate (3×3 mL). The combined organic layers were dried over magnesium sulfate, filtered and concentrated in vacuo. The crude product was purified by column chromatography (Merck silica gel 60, 40-63 μm, ethyl acetate/dichloromethane, 2-5%) to afford the desired product, 4-hydroxy-1-(3-methyl-butyl)-2-oxo-1,2-dihydro-pyrrolo[1,2-b]pyridazine-3-carboxylic acid ethyl ester (0.058 g, 0.20 mmol, 55% yield) as a light tan solid. $^1$H NMR (400 MHz, DMSO-d$_6$) δ 0.93 (6H, d, J=6.4 Hz), 1.30 (3H, t, J=6.8 Hz), 1.49 (2H, q, $J_1$=15.2 Hz, $J_2$=7.6 Hz), 1.63 (1H, m), 4.23-4.30 (4H, m), 6.56 (1H, m), 6.87 (1H, m), 7.68 (1H, m); LC-MS (ESI) calcd for $C_{15}H_{20}N_2O_4$ 292.33. found 293.30 [M+H$^+$].

(g) 3-(1,1-Dioxo-1,4-dihydro-1λ⁶-benzo[1,2,4]thia-diazin-3-yl)-4-hydroxy-1-(3-methyl-butyl)-pyrrolo[1,2-b]pyridazin-2-one

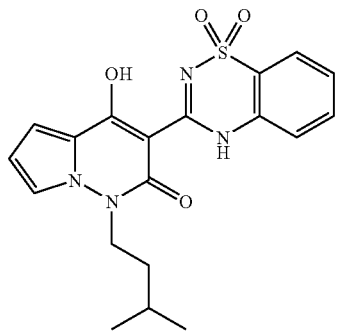

4-Hydroxy-1-(3-methyl-butyl)-2-oxo-1,2-dihydro-pyrrolo[1,2-b]pyridazine-3-carboxylic acid ethyl ester (Example 1f, 0.040 g, 0.14 mmol) was mixed with 2-amino-benzenesulfonamide (0.0235 g, 0.14 mmol) and the resulting mixture was heated to 180° C. for 20 min. The resulting crude oil was allowed to cool to 25° C. and ethanol (0.5 mL) was added and sonicated to afford a tan precipitate, which was collected and dried in vacuo. The crude solid was dissolved in 1.0 M aqueous potassium hydroxide solution (0.3 mL) and heated to 110° C. for 20 h. The reaction mixture was allowed to cool to 25° C. and 10% aqueous hydrochloric acid solution (0.5 mL) was added and the resulting white precipitate was collected. The solid was washed with methanol and dried in vacuo to afford the desired product, 3-(1,1-dioxo-1,4-dihydro-1λ⁶-benzo[1,2,4]thiadiazin-3-yl)-4-hydroxy-1-(3-methyl-butyl)-pyrrolo[1,2-b]pyridazin-2-one (0.028 g, 0.07 mmol, 52% yield) as a white solid. ¹H NMR (400 MHz, DMSO-d₆) δ 0.97 (6H, d, J=6.4 Hz), 1.28 (2H, bs), 1.61 (2H, q, J₁=15.2 Hz, J₂=6.8 Hz), 1.74 (1H, m), 4.43 (2H, t, J=8.0 Hz), 6.71 (1H, dd, J₁=4.4 Hz, J₂=2.4 Hz), 7.04 (1H, d, J=4.4 Hz), 7.23 (1H, t, J=8.0 Hz), 7.50 (1H, t, J=7.6 Hz), 7.63 (1H, d, J=8.4 Hz), 7.88 (1H, d, J=8.0 Hz), 7.90 (1H, m); LC-MS (ESI) calcd for C₁₉H₂₀N₄O₄S 400.45. found 401.28 [M+H⁺].

EXAMPLE 2

4-Hydroxy-3-(7-methoxy-1,1-dioxo-1,4-dihydro-1λ⁶-benzo[1,2,4]thiadiazin-3-yl)-1-(3-methyl-butyl)-pyrrolo[1,2-b]pyridazin-2-one

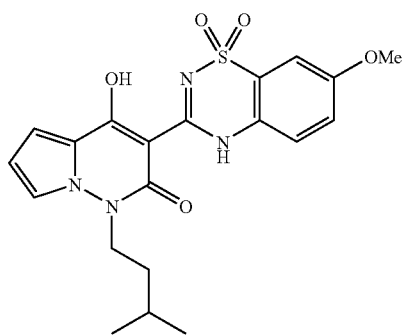

a) 7-Methoxy-1,1-dioxo-1,4-dihydro-2H-1λ⁶-benzo[1,2,4]thiadiazin-3-one

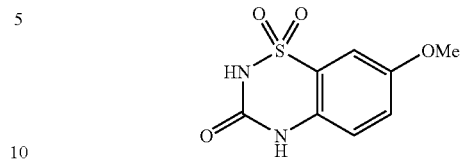

Chlorosulfonyl isocyanate (17 mL, 195 mmol) was dissolved in nitroethane (150 mL) and cooled to −40° C. A solution of 4-methoxyaniline (20 g, 162 mmol) in nitroethane (100 mL) was then added dropwise with stirring. After the addition was completed, the reaction was stirred for an additional 5 min and aluminum chloride (25 g, 195 mmol) was added. The mixture was then quickly heated to 110° C. with stirring for 20 min. The crude material was then poured onto ice and the precipitate was collected by vacuum filtration, washed with cold water, and dried in vacuo to afford the desired product, 7-methoxy-1,1-dioxo-1,4-dihydro-2H-1λ⁶-benzo[1,2,4]thiadiazin-3-one (35 g, 153.5 mmol, 79% yield) as a purple powder. ¹H NMR (400 MHz, DMSO-d₆): δ 3.6 (br, 1H), 3.78 (s, 3H), 7.2 (m, 3H), 11.05 (s, 1H).

b) 2-Amino-5-methoxy-benzenesulfonamide

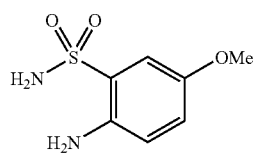

A solution of 7-methoxy-1,1-dioxo-1,4-dihydro-2H-1λ⁶-benzo[1,2,4]thiadiazin-3-one (Example 2a, 15 g, 65.7 mmol) in a 50% aqueous sulfuric acid solution (140 mL) was heated at 130° C. for 6 h. The solution was then poured over ice and neutralized at 0° C. with the addition of saturated aqueous sodium hydroxide solution. The mixture was then extracted with ethyl acetate. The organic phase was washed with brine, and dried over magnesium sulfate, filtered and dried in vacuo to afford the desired product, 2-amino-5-methoxy-benzenesulfonamide (8.1 g, 40.1 mmol, 61% yield) as a brown solid. See procedure described in Girard, Y., et al., *J. Chem. Soc. Perkin Trans* 1, 1043-1047 (1979). ¹H NMR (400 MHz, DMSO -d₆): δ 3.65 (s, 3H), 5.40 (s, 2H), 6.73 (d, 1H, J=8.8 Hz), 6.90 (dd, 1H, J₁=8.8 Hz, J₂=2.8 Hz), 7.07 (d, 1H, J=2.8 Hz), 7.19 (s, 2H).

c) 4-Hydroxy-3-(7-methoxy-1,1-dioxo-1,4-dihydro-1λ⁶-benzo[1,2,4]thiadiazin-3-yl)-1-(3-methyl-butyl)-pyrrolo[1,2-b]pyridazin-2-one

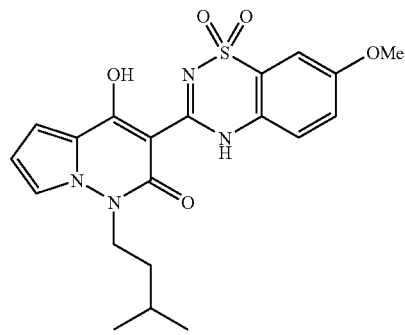

4-Hydroxy-1-(3-methyl-butyl)-2-oxo-1,2-dihydro-pyrrolo[1,2-b]pyridazine-3-carboxylic acid ethyl ester (Example 1f, 0.040 g, 0.14 mmol) was mixed with 2-amino-5-methoxy-benzenesulfonamide (Example 2b, 0.0235 g, 0.14 mmol) and the resulting mixture was heated to 180° C. for 20 min. The resulting crude oil was allowed to cool to 25° C. and ethanol (0.5 mL) was added and sonicated to afford a tan precipitate, which was collected and dried in vacuo. The crude solid was dissolved in 1.0 M aqueous potassium hydroxide solution (0.5 mL) and heated to 110° C. for 12 h. The reaction mixture was allowed to cool to 25° C. and 10% aqueous hydrochloric acid solution (0.5 mL) was added and the resulting white precipitate was collected. The crude solid was washed with methanol and dried in vacuo to afford the desired product, 4-hydroxy-3-(7-methoxy-1,1-dioxo-1,4-dihydro-1λ⁶-benzo[1,2,4]thiadiazin-3-yl)-1-(3-methyl-butyl)-pyrrolo[1,2-b]pyridazin-2-one (0.027 g, 0.063 mmol, 47% yield) as a white solid. ¹H NMR (400 MHz, DMSO-d₆) δ 1.07 (6H, d, J=6.4 Hz), 1.69 (1H, m), 1.78 (1H, m), 3.89 (3H, s), 4.39 (2H, t, J=7.6 Hz), 6.60 (1H, dd, J₁=4.4 Hz, J₂=2.8 Hz), 7.04 (1H, d, J=4.4 Hz), 7.05 (1H, dd, J₁=4.8 Hz, J₂=2.0 Hz), 7.25 (1H, m), 7.17 (1H, m), 7.39 (1H, d, J=2.0 Hz); LC-MS (ESI) calcd for C₁₉H₂₂N₄O₅S 430.49. found 431.33 [M+H⁺].

EXAMPLE 3

N-{3-[4-Hydroxy-1-(3-methyl-butyl)-2-oxo-1,2-dihydro-pyrrolo[1,2-b]pyridazin-3-yl]-1,1-dioxo-1,4-dihydro-1λ⁶-benzo[1,2,4]thiadiazin-7-yl}-methane-sulfonamide

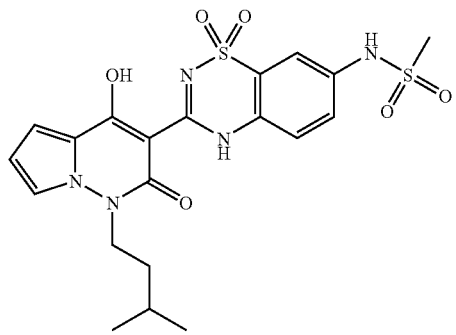

a) N-(4-Nitro-phenyl)-methanesulfonamide

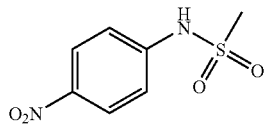

4-Nitro-phenylamine (25 g, 181 mmol) was dissolved in pyridine (450 mL). Methanesulfonyl chloride (14.0 mL, 181 mmol) was added dropwise while stirring. The mixture was stirred for 16 h at 25° C. The solution was concentrated in vacuo to a volume of ~50 mL. The mixture was diluted with ethyl acetate (400 mL), washed with 1.0 M aqueous hydrochloric acid solution (5×200 mL). The combined aqueous layers were back-extracted with ethyl acetate (200 mL). The combined organic layers were dried over magnesium sulfate, filtered and concentrated in vacuo to a volume of ~250 mL. The product precipitated and was collected by vacuum filtration. The filtrate was concentrated in vacuo to a volume of ~125 mL upon which additional product precipitated. The solid was collected by vacuum filtration. The solids were combined to afford the desired product, N-(4-nitro-phenyl)-methanesulfonamide (25 g, 115.62 mmol, 64% yield) as a pale yellow solid. ¹H NMR (400 MHz, DMSO-d₆) δ 3.17 (3H, s), 7.35 (2H, d, J=9.4 Hz), 8.20 (2H, d, J=9.1 Hz), 10.69 (1H, s).

b) N-(4-Amino-phenyl)-methanesulfonamide

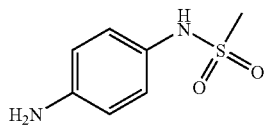

N-(4-Nitro-phenyl)-methanesulfonamide (Example 3a, 25 g, 115.62 mmol) was dissolved in N,N-dimethylformamide (15 mL) with gentle heating to ~50° C. via heat gun. Ethyl acetate (100 mL) and methanol (100 mL) were added followed by 10% palladium on carbon (4 g). The mixture was degassed while stirring and the flask was charged with hydrogen gas via balloon. The mixture was stirred at 25° C. for 4.5 h. The mixture was filtered through Celite (rinsed with ethyl acetate) and concentrated in vacuo to a yellow green solution with a volume of ~10 mL. Dichloromethane (~50 mL) was added and a solid began to precipitate. The mixture was stirred at 25° C. for 30 min. The solid was collected by vacuum filtration and dried in vacuo to afford the desired product, N-(4-amino-phenyl)-methanesulfonamide (15.32 g, 82.26 mmol, 71% yield) as a beige powder. ¹H NMR (400 MHz, DMSO-d₆) δ 2.79 (3H, s), 5.00 (2H, s), 6.49 (2H, d, J=8.5 Hz), 6.87 (2H, d, J=8.6 Hz), 8.87 (1H, s).

c) N-(1,1,3-Trioxo-1,2,3,4-tetrahydro-1λ⁶-benzo[1,2,4]thiadiazin-7-yl)-methanesulfonamide

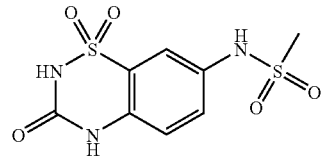

Chloro-sulfonyl-isocyanate (1.7 mL, 19.6 mmol) was dissolved in nitroethane (10 mL) and chilled to −40° C. under nitrogen. N-(4-Amino-phenyl)-methanesulfonamide (Example 3b, 3 g, 16.1 mmol) was added dropwise as a pre-dissolved solution in nitroethane (25 mL). The mixture was stirred at −40° C. for 15 min. Aluminum chloride (8 g, 60 mmol) was added and the mixture was heated at 110° C. for 30 min while stirring. The mixture was poured onto ice (~150 g). Upon melting, the product was extracted into ethyl acetate (5×250 mL). The combined organic layers were dried over magnesium sulfate, filtered and concentrated in vacuo to afford the desired product, N-(1,1,3-trioxo-1,2,3,4-tetrahydro-1$\lambda^6$-benzo[1,2,4]thiadiazin-7-yl)-methanesulfonamide (3.63 g, 12.46 mmol, 77% yield) as a beige solid. $^1$H NMR (400 MHz, DMSO-d$_6$) δ 3.00 (3H, s), 7.22 (1H, d, J=8.5 Hz), 7.46 (1H, dd, J$_1$=8.8 Hz, J$_2$=2.7 Hz), 7.51 (1H, d, J=2.4 Hz), 9.92 (1H, s), 11.20 (1H, s).

d) 2-Amino-5-methanesulfonylamino-benzenesulfonamide

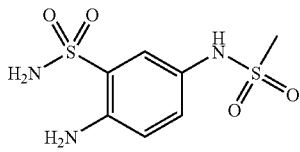

N-(1,1,3-Trioxo-1,2,3,4-tetrahydro-1$\lambda^6$-benzo[1,2,4]thiadiazin-7-yl)-methanesulfonamide (Example 3c, 1 g, 3.4 mmol) was suspended in 12 M aqueous hydrochloric acid solution (60 mL). The mixture was stirred at 105° C. for 16 h. All solids were dissolved at this point. The mixture was diluted with water (250 mL). The solution was concentrated in vacuo to an orange solid. The solid was dissolved in water (20 mL) and concentrated in vacuo to an orange solid. The solid was dissolved in water (5 mL) and the product was extracted into ethyl acetate (6×20 mL). The combined organic phase was dried over magnesium sulfate, filtered and concentrated in vacuo to an orange solid. Purification by flash column chromatography (Merck silica gel 60, 40-63 μm, 75% ethyl acetate in hexanes) afforded the desired product, 2-amino-5-methanesulfonylamino-benzenesulfonamide (0.41 g, 1.55 mmol, 45% yield), as a beige solid. $^1$H NMR (400 MHz, DMSO-d$_6$) δ 2.86 (3H, s), 5.77 (2H, s), 6.76 (1H, d, J=8.6 Hz), 7.11 (1H, dd, J$_1$=8.6 Hz, J$_2$=2.4 Hz), 7.25 (2H, bs), 7.43 (1H, d, J=3.1 Hz), 9.16 (1H, s).

Alternatively, the 2-amino-5-methanesulfonylamino-benzenesulfonamide intermediate of 3(d) above was preferably made according to the following procedure:

(a)': N-(4-Nitro-phenyl)-methanesulfonamide

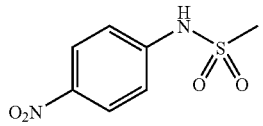

A solution of methanesulfonylchloride (47.1 mL, 0.61 mol) in acetonitrile (160 mL) was added over 40 min to a solution of 4-nitroaniline (80.0 g, 0.58 mol) and pyridine (70.2 mL, 0.87 mol) in acetonitrile (400 mL) at 25° C. The mixture was stirred at 25° C. for 19 h, and then water (800 mL) was added. The resulting suspension was stirred at 25° C. for 30 min, and then was filtered through medium paper using a Büchner funnel. The collected solid was washed with water (2×150 mL) and air-dried overnight to afford the desired product, N-(4-nitro-phenyl)-methanesulfonamide (111.4 g, 0.52 mol, 89% yield) as a pale yellow solid. $^1$H NMR (400 MHz, DMSO-d$_6$) δ 3.17 (3H, s), 7.35 (2H, d, J=9.4 Hz), 8.20 (2H, d, J=9.1 Hz), 10.69 (1H, s).

(b)': N-(4-Amino-phenyl)-methanesulfonamide

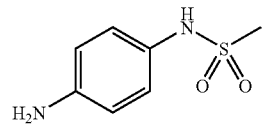

5% Palladium on carbon ("wet", 11.1 g) was added to a solution of N-(4-nitro-phenyl)-methanesulfonamide (Example 3a', 111.4 g, 0.52 mol) in tetrahydrofuran (900 mL) at 25° C. The atmosphere above the resulting suspension was replaced with hydrogen gas and the reaction mixture was maintained under 1 atmosphere of hydrogen at 25° C. for 4 days using several balloons. The mixture was then filtered through Celite and the Celite was washed with tetrahydrofuran (3×100 mL). The combined filtrate and washings were concentrated in vacuo to approximately 300 mL volume and heptane (500 mL) was added dropwise via addition funnel over 45 min at 25° C. with vigorous stirring. The resulting suspension was stirred for an additional 45 min at 25° C., and then was filtered through medium paper using a Büchner funnel. The collected solid was washed with heptane (1×150 mL) and was air-dried to afford the desired product, N-(4-amino-phenyl)-methanesulfonamide (90.7 g, 0.49 mol, 95% yield) as a beige powder. $^1$H NMR (400 MHz, DMSO-d$_6$) δ 2.79 (3H, s), 5.00 (2H, s), 6.49 (2H, d, J=8.5 Hz), 6.87 (2H, d, J=8.6 Hz), 8.87 (1H, s).

(c)': N-(1,1,3-Trioxo-1,2,3,4-tetrahydro-1$\lambda^6$-benzo[1,2,4]thiadiazin-7-yl)-methanesulfonamide

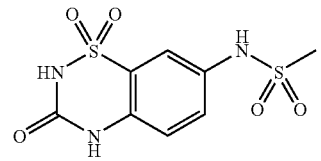

A solution of N-(4-amino-phenyl)-methanesulfonamide (Example 3b', 90.7 g, 0.49 mol) in nitroethane (900 mL) was added dropwise over 1.5 h to a mechanically stirred solution of chlorosulfonylisocyanate (50.6 mL, 0.54 mol) in nitroethane (150 mL) at −20° C. The resulting suspension was stirred at −20° C. for 30 min, then aluminum chloride (77.9 g, 0.58 mol) was added in one portion over 1 min. The resulting brown solution was warmed to 25° C., and then was heated at 110° C. for 1 h (considerable gas evolution was noted during this time). After cooling to −5° C., water (300 mL) was added dropwise via addition funnel over 15 min, followed by the rapid addition of more water (700 mL). The resulting suspension was allowed to warm to 25° C. and vigorously stirred for 30 min, and then was filtered through medium paper using a Büchner funnel. The collected solid was washed with water (1×300 mL) and was air-dried to afford the desired product, N-(1,1,3-trioxo-1,2,3,4-tetrahydro-1$\lambda^6$-benzo[1,2,4]thiadiazin-7-yl)-methanesulfonamide (115.2 g, 0.40 mmol, 81% yield) as a beige solid. $^1$H NMR (400 MHz, DMSO-d$_6$) δ 3.00 (3H, s), 7.22 (1H, d, J=8.5 Hz), 7.46 (1H, dd, J$_1$=8.8 Hz, J$_2$=2.7 Hz), 7.51 (1H, d, J=2.4 Hz), 9.92 (1H, s), 11.20 (1H, s).

(d)':
2-Amino-5-methanesulfonylamino-benzenesulfonamide

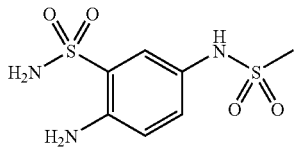

A mechanically stirred suspension of N-(1,1,3-trioxo-1,2,3,4-tetrahydro-1λ⁶-benzo[1,2,4]thiadiazin-7-yl)-methanesulfonamide (Example 3c', 115.2 g, 0.40 mol) in 9.0 M aqueous sulfuric acid (500 mL) was heated to 130° C. for 2.5 h (considerable gas evolution was noted during this time). The resulting brown solution was cooled to 0° C. and an aqueous solution of sodium hydroxide (351 g in 750 mL water; ca. 11.7 M) was added via addition funnel over 45 min. The pH of the reaction mixture was then adjusted to approximately 7.0 by the dropwise addition of 3.0 M aqueous sodium carbonate solution. The resulting suspension was allowed to warm to 25° C. and stirred for 1 h, then was filtered through medium paper using a Büchner funnel. The collected solid was washed with water (1×300 mL) and was dried in a vacuum oven at 50° C. to afford a mixture of 2-amino-5-methanesulfonylamino-benzenesulfonamide and 2,5-di-amino-benzenesulfonamide (1.5:1.0 ratio, 70.0 g, 75% yield) as a brown solid. $^1$H NMR (400 MHz, DMSO-$d_6$) δ: 2.86 (3H, s), 4.54 (2H, bs), 4.98 (2H, bs), 5.77 (2H, s), 6.55-6.60 (2H, m), 6.76 (1H, d, J=8.6 Hz), 6.87 (1H, d, J=2.2 Hz), 6.99 (2H, bs), 7.11 (1H, dd, $J_1$=8.6 Hz, $J_2$=2.4 Hz), 7.25 (2H, bs), 7.43 (1H, d, J=3.1 Hz), 9.16 (1H, s).

A solution of methanesulfonylchloride (8.2 mL, 0.11 mol) in acetonitrile (100 mL) was added over 15 min to a solution of the above mixture of 2-amino-5-methanesulfonylamino-benzenesulfonamide and 2,5-diamino-benzenesulfonamide (1.5:1.0 ratio, 60.0 g) and pyridine (12.0 mL, 0.15 mol) in acetonitrile (500 mL) at 25° C. The mixture was stirred at 25° C. for 15 h, and then was concentrated in vacuo to approximately 300 mL volume. Ethyl acetate (300 mL) was added and the resulting suspension was stirred at 25° C. for 10 min, and then was filtered through medium paper using a Büchner funnel. The collected solid was washed with water (1×200 mL) and was dried in a vacuum oven at 50° C. to afford the desired product, 2-amino-5-methanesulfonylamino-benzenesulfonamide (54.0 g, 0.20 mol, 80% yield) as a beige solid. $^1$H NMR (400 MHz, DMSO-$d_6$) δ 2.86 (3H, s), 5.77 (2H, s), 6.76 (1H, d, J=8.6 Hz), 7.11 (1H, dd, $J_1$=8.6 Hz, $J_2$=2.4 Hz), 7.25 (2H, bs), 7.43 (1H, d, J=3.1 Hz), 9.16 (1H, s).

e) N-{3-[4-Hydroxy-1-(3-methyl-butyl)-2-oxo-1,2-dihydro-pyrrolo[1,2-b]pyridazin-3-yl]-1,1-dioxo-1,4-dihydro-1λ⁶-benzo[1,2,4]thiadiazin-7-yl}-methanesulfonamide

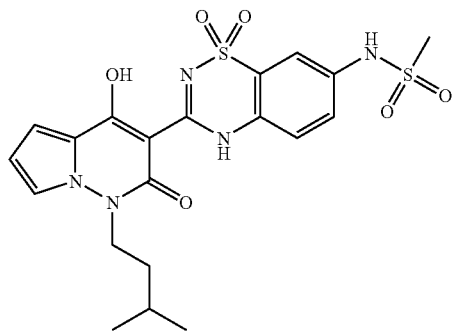

4-Hydroxy-1-(3-methyl-butyl)-2-oxo-1,2-dihydro-pyrrolo[1,2-b]pyridazine-3-carboxylic acid ethyl ester (Example 1f, 0.098 g, 0.33 mmol) and 2-amino-5-methanesulfonylamino-benzenesulfonamide (Example 3d or Example 3d', 0.089 g, 0.33 mmol) were mixed in pyridine (1.5 mL) and the mixture was stirred under a nitrogen atmosphere at 120° C. for 3 h. LC-MS analysis confirmed the disappearance of the starting material and the formation of the uncyclized intermediate 4-hydroxy-1-(3-methyl-butyl)-2-oxo-1,2-dihydro-pyrrolo[1,2-b]pyridazine-3-carboxylic acid (4-methanesulfonylamino-2-sulfamoyl-phenyl)-amide. 1,8-Diazabicyclo[5,4,0]undec-7-ene (DBU) (150 μL, 1.0 mmol) was added and the mixture was stirred under nitrogen atmosphere at 120° C. for 16 h. LC-MS analysis indicated completion of the reaction and the mixture was concentrated in vacuo. The crude material was dissolved in dimethylsulfoxide and purified by preparative HPLC (Column ODS-A 100 Å, 5μ. 150×21.2 mm. Flow 22 mL/min, 30-100% acetonitrile/water with 0.01% trifluoroacetic acid) and lyophilized from water and 1,4-dioxane to afford the desired product, N-{3-[4-hydroxy-1-(3-methyl-butyl)-2-oxo-1,2-dihydro-pyrrolo[1,2-b]pyridazin-3-yl]-1,1-dioxo-1,4-dihydro-1λ⁶-benzo[1,2,4]thiadiazin-7-yl}-methanesulfonamide (0.016 g, 0.032 mmol, 9.7% yield) as a light brown powder. $^1$H NMR (DMSO-$d_6$) δ 0.96 (6H, d, J=6.3 Hz), 1.55-1.60 (2H, m), 1.67-1.77 (1H, m), 3.07 (1H, s), 4.40 (2H, t, J=7.8 Hz), 6.70 (1H, s), 7.02 (1H, s), 7.52-7.67 (3H, m), 7.90 (1H, s), 10.20 (1H, s); LC-MS (ESI) calcd for $C_{20}H_{23}N_5O_6S_2$ 493.1 found 494.3 [M+H⁺].

EXAMPLE 4

N-{3-[1-(3,3-Dimethyl-butyl)-4-hydroxy-2-oxo-1,2-dihydro-pyrrolo[1,2-b]pyridazin-3-yl]-1,1-dioxo-1,4-dihydro-1λ⁶-benzo[1,2,4]thiadiazin-7-yl}-methanesulfonamide

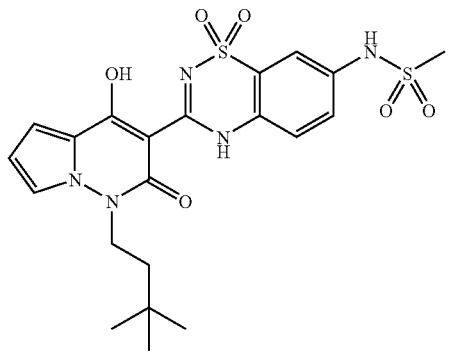

a) 2-Amino-5-iodo-benzenesulfonamide

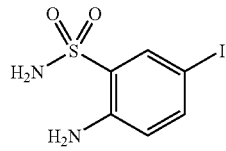

2-Amino-benzenesulfonamide (5.15 g, 29.3 mmol) was dissolved in chloroform (87 mL), and N-iodosuccinimide (7.29 g, 30.77 mmol) was added under a nitrogen atmosphere. The mixture was heated at reflux for 24 h, allowed to cool to 25° C., and filtered through a sinter funnel. The solid was washed with chloroform and 10% methanol/chloroform (3-8 times) to afford the desired product, 2-amino-5-iodo-benzenesulfonamide (6.78 g, 22.75 mmol, 78% yield) as a brown crystalline solid. $^1$H NMR (400 MHz, DMSO-$d_6$): 5.98 (s, 2H), 6.62 (d, 1H, J=8.8 Hz), 7.31 (s, 2H), 7.45 (dd, 1H, J=8.8, 2.4 Hz), 7.73 (d, 1H, J=2.0 Hz).

b) (7-iodo-1,1-dioxo-1,4-dihydro-1$\lambda^6$-benzo[1,2,4]thiadiazin-3-yl)-acetic acid

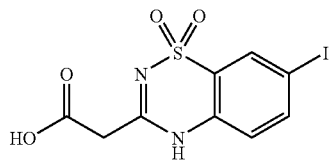

2-Amino-5-iodo-benzenesulfonamide (Example 4a, 2.0 g, 6.71 mmol) was dissolved in N,N-dimethylacetamide (5 mL) and diethyl ether (7 mL). Ethyl 3-chloro-3-oxo-propionate (0.916 g, 6.71 mmol) was added and the reaction mixture was stirred at 25° C. for 2 h. The reaction mixture was diluted with diethyl ether (10 mL) and water (20 mL). Upon mixing vigorously, a precipitate formed. The solid was collected by vacuum filtration, rinsed with 1.0 M aqueous hydrochloric acid solution (2×10 mL) and dried in vacuo for 2 h. The solid was dissolved in 8% aqueous sodium hydroxide solution (50 mL) and stirred at 100° C. for 15 min. Upon cooling to 25° C., the solution was neutralized with 6.0 M aqueous hydrochloric acid solution. Additional 1.0 M aqueous hydrochloric acid solution (20 mL) was added and the desired product precipitated. The solid was collected by vacuum filtration, rinsed with 1.0 M aqueous hydrochloric acid solution (2×10 mL) and dried in vacuo for 16 h to afford the desired product, (7-iodo-1,1-dioxo-1,4-dihydro-1$\lambda^6$-benzo[1,2,4]thiadiazin-3-yl)-acetic acid (2.0 g, 5.46 mmol, 81% yield) as a pale pink powder. $^1$H NMR (400 MHz, DMSO-$d_6$) δ: 3.58 (3H, s), 7.13 (1H, d, J=8.5 Hz), 7.98 (1H, dd, $J_1$=8.6 Hz, $J_2$=1.7 Hz), 8.03 (1H, d, J=2.5 Hz), 12.33 (1H, bs), 13.05 (1H, bs). LC-MS (ESI) calcd for $C_9H_7IN_2O_4S$ 365.92. found 366.95 [M+H$^+$].

c) 1-(3,3-Dimethyl-butylamino)-1H-pyrrole-2-carboxylic acid allyl ester

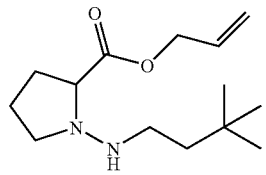

Dimethylsulfoxide (6.80 mL, 95.7 mmol) was added over 5 min to a solution of oxalylchloride (23.9 mL, 47.8 mmol) in dichloromethane at −78° C. The resulting mixture was stirred at −78° C. for 5 min, then 3,3-dimethyl-butan-1-ol (5.22 mL, 43.1 mmol) was added. After stirring an additional 30 min at −78° C., triethylamine (23.3 mL, 167 mmol) was added and the reaction mixture warmed to 0° C. and stirred at that temperature for 45 min. The mixture was then transferred to a separatory funnel and was washed with 0.5 M aqueous hydrochloric acid. The organic layer was dried over sodium sulfate, filtered and was concentrated in vacuo to a volume of about 70 mL (water bath temperature=0° C.). Methanol (100 mL) was added followed sequentially by 1-amino-1H-pyrrole-2-carboxylic acid allyl ester (Example 1b, 7.16 g, 43.1 mmol), acetic acid (6 mL), and sodium cyanoborohydride (5.42 g, 86.3 mmol). The reaction mixture was stirred at 23° C. for 2 h, and then was partitioned between saturated aqueous sodium bicarbonate solution (400 mL) and a 1:1 mixture of ethyl acetate and hexanes (2×200 mL). The organic layers were dried over sodium sulfate, filtered and concentrated in vacuo. Purification of the residue by flash column chromatography (Merck silica gel 60, 40-63 μm, 5→10% ethyl acetate in hexanes) afforded the desired product, 1-(3,3-dimethyl-butylamino)-1H-pyrrole-2-carboxylic acid allyl ester (4.04 g, 16.15 mmol, 37% yield) as a clear liquid. $^1$H NMR (400 MHz, CDCl$_3$) δ: 0.91 (9H, s), 1.42-1.46 (2H, m), 2.98-3.04 (2H, m), 4.75-4.77 (2H, m), 5.26-5.28 (1H, m), 5.37-5.41 (1H, m), 5.96-5.99 (1H, m), 6.01-6.05 (1H, m), 6.27-6.30 (1H, m), 6.89-6.91 (1H, m), 6.96-6.98 (1H, m).

d) 1-(3,3-Dimethyl-butyl)-4-hydroxy-3-(7-iodo-1,1-dioxo-1,4-dihydro-1$\lambda^6$-benzo[1,2,4]thiadiazin-3-yl)-pyrrolo[1,2-b]pyridazin-2-one

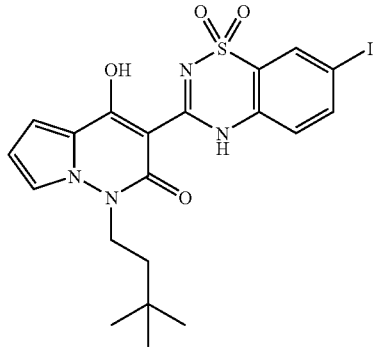

(7-Iodo-1,1-dioxo-1,4-dihydro-1$\lambda^6$-benzo[1,2,4]thiadiazin-3-yl)-acetic acid (Example 4b, 0.3 g, 0.819 mmol) was dissolved in N,N-dimethylformamide (4.1 mL). 1-(3,3-Dimethyl-butylamino)-1H-pyrrole-2-carboxylic acid allyl ester (Example 4c, 0.205 g, 0.819 mmol) was added followed by a 1.0 M solution of N,N-dicyclohexylcarbodiimide in dichloromethane (0.860 mL, 0.86 mmol). The mixture was stirred at 25° C. for 2 h. N,N-Dicyclohexylurea precipitation was visible at this point. The mixture was diluted with dichloromethane (5 mL) and filtered under reduced pressure. The filtrate was washed with 1.0 M aqueous hydrochloric acid solution (2×10 mL), saturated aqueous brine solution (10 mL), dried over magnesium sulfate, filtered and concentrated in vacuo to afford a golden oil. The oil was dissolved in ethanol (4.1 mL). A 21% solution of sodium ethoxide in ethanol (0.673 mL) was added and the mixture was stirred at 80° C. for 4 h. Additional sodium ethoxide in ethanol (0.673 mL) was added and the mixture was stirred at 80° C. for 4 h. Upon cooling to 25° C., the pH was adjusted to approximately 6 by the addition of 3.0 M aqueous hydrochloric acid solution. Immediate precipitation was observed. Methanol (3 mL) was added and the mixture was shaken vigorously. The solid was collected by vacuum filtration, rinsed with methanol (3×2 mL) and dried in vacuo for 16 h to afford the desired product, 1-(3,3-dimethyl-butyl)-4-hydroxy-3-(7-iodo-1,1-dioxo-1,4-dihydro-1$\lambda^6$-benzo[1,2,4]thiadiazin-3-yl)-pyrrolo[1,2-b]pyridazin-2-one (0.268 g, 0.67 mmol, 82% yield) as a white powder. LC-MS (ESI) calcd for $C_{20}H_{21}IN_4O_4S$. found 540.03. found 366.95 [M+H$^+$].

e) N-{3-[1-(3,3-Dimethyl-butyl)-4-hydroxy-2-oxo-1, 2-dihydro-pyrrolo[1,2-b]pyridazin-3-yl]-1,1-dioxo-1, 4-dihydro-1λ⁶-benzo[1,2,4]thiadiazin-7-yl}-methanesulfonamide

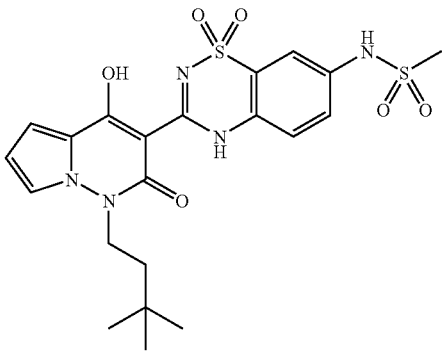

1-(3,3-Dimethyl-butyl)-4-hydroxy-3-(7-iodo-1,1-dioxo-1,4-dihydro-1λ⁶-benzo[1,2,4]thiadiazin-3-yl)-pyrrolo[1,2-b]pyridazin-2-one (Example 4d, 0.065 g, 0.120 mmol), potassium triphosphate (0.128 g, 0.60 mmol), sarcosine (0.006 g, 0.072 mmol), and copper (I) iodide (0.006 g, 0.03 mmol) were combined. Anhydrous N,N-dimethylformamide (2 mL) was added followed by methanesulfonamide (0.114 g, 1.2 mmol). The solution was degassed while stirring under vacuum and the flask was purged with nitrogen. The mixture was stirred at 100° C. for 2 h. Upon cooling, the mixture was diluted with ethyl acetate (100 mL), washed with 1.0 M aqueous hydrochloric acid solution (3×50 mL) and dried over magnesium sulfate. The entire organic layer was passed through a plug of silica gel. The filtrate was concentrated in vacuo to afford a solid. The solid was triturated with a 1:1 mixture of ethyl acetate and hexanes, collected by vacuum filtration, triturated with methanol and collected by vacuum filtration. The solid was dried in vacuo for 16 h to afford the desired product, N-{3-[1-(3,3-dimethyl-butyl)-4-hydroxy-2-oxo-1,2-dihydro-pyrrolo[1,2-b]pyridazin-3-yl]-1,1-dioxo-1, 4-dihydro-1λ⁶-benzo[1,2,4]thiadiazin-7-yl}-methanesulfonamide (0.031 g, 0.061 mmol, 51% yield) as a pale yellow powder. ¹H NMR (400 MHz, DMSO-d₆) δ: 1.01 (9H, s), 1.57-1.62 (2H, m), 3.07 (3H, s), 4.39-4.43 (2H, m), 6.70-6.72 (1H, m), 7.03 (1H, d, J=3.8 Hz), 7.53 (1H, dd, J₁=8.7 Hz, J₂=2.8 Hz), 7.60 (1H, d, J=2.3 Hz), 7.67 (1H, d, J=8.4 Hz), 7.75 (1H, s), 10.20 (1H, s), 13.72 (1H, bs). LC-MS (ESI) calcd for C₂₁H₂₅N₅O₆S₂. found 507.12. found 508.36 [M+H⁺].

EXAMPLE 5

N-{3-[1-(3,3-Dimethyl-butyl)-4-hydroxy-2-oxo-1,2-dihydro-pyrrolo[1,2-b]pyridazin-3-yl]-1,1-dioxo-1,4-dihydro-1λ⁶-benzo[1,2,4]thiadiazin-7-yl}-N-methyl-methanesulfonamide

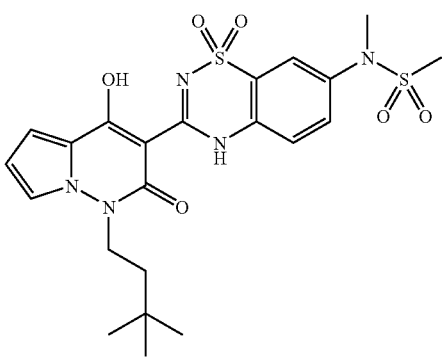

1-(3,3-Dimethyl-butyl)-4-hydroxy-3-(7-iodo-1,1-dioxo-1,4-dihydro-1λ⁶-benzo[1,2,4]thiadiazin-3-yl)-pyrrolo[1,2-b]pyridazin-2-one (Example 4d, 0.257 g, 0.476 mmol), potassium triphosphate (0.505 g, 2.38 mmol), sarcosine (0.025 g, 0.285 mmol), and copper (I) iodide (0.022 g, 0.119 mmol) were combined. Anhydrous N,N-dimethylformamide (9.5 mL) was added followed by N-methyl-methanesulfonamide (0.519 g, 4.76 mmol). The solution was degassed while stirring under vacuum and the flask purged with nitrogen. The mixture was stirred at 100° C. for 1 h. Additional copper (I) iodide (0.1 g, 0.525 mmol) was added. The mixture continued to stir at 100° C. for 3 h. Upon cooling, the mixture was diluted with ethyl acetate (200 mL), washed with 1.0 M aqueous hydrochloric acid solution (2×100 mL), dried over magnesium sulfate. The entire organic layer was passed through a plug of silica gel. Upon concentrating in vacuo to a volume of approximately 10 mL, the desired product precipitated. The solid was collected by vacuum filtration. The solid was recrystallized in ethyl acetate, collected by vacuum filtration and dried in vacuo to afford the desired product, N-{3-[1-(3,3-dimethyl-butyl)-4-hydroxy-2-oxo-1,2-dihydro-pyrrolo[1,2-b]pyridazin-3-yl]-1,1-dioxo-1,4-dihydro-1λ⁶-benzo[1,2,4]thiadiazin-7-yl}-N-methyl-methanesulfonamide (0.082 g, 0.157 mmol, 33% yield) as a pale yellow powder. ¹H NMR (400 MHz, DMSO-d₆) δ: 1.02 (9H, s), 1.58-1.62 (2H, m), 3.01 (3H, s), 3.31 (3H, s), 4.40-4.44 (2H, m), 6.72-6.72 (1H, m), 7.04 (1H, d, J=3.9 Hz), 7.70-7.76 (3H, m), 7.88 (1H, s), 13.78 (1H, bs). LC-MS (ESI) calcd for C₂₂H₂₇N₅O₆S₂. found 521.14. found 522.6 [M+H⁺].

EXAMPLE 6

N-{3-[4-Hydroxy-1-(3-methyl-butyl)-2-oxo-1,2-dihydro-pyrrolo[1,2-b]pyridazin-3-yl]-1,1-dioxo-1,4-dihydro-1λ⁶-benzo[1,2,4]thiadiazin-7-yl}-N-methyl-methanesulfonamide

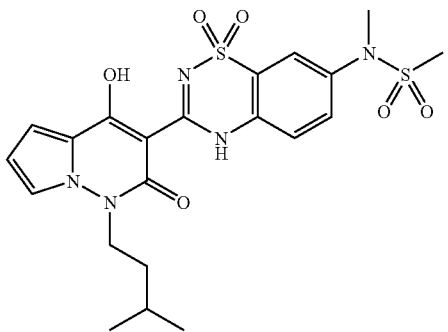

a) 4-Hydroxy-3-(7-iodo-1,1-dioxo-1,4-dihydro-1λ⁶-benzo[1,2,4]thiadiazin-3-yl)-1-(3-methyl-butyl)-pyrrolo[1,2-b]pyridazin-2-one

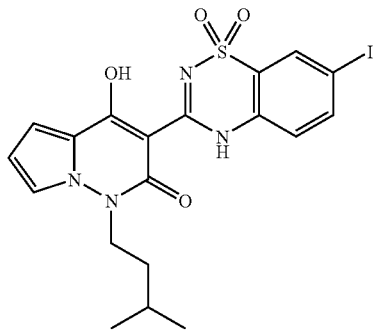

(7-Iodo-1,1-dioxo-1,4-dihydro-1λ⁶-benzo[1,2,4]thiadiazin-3-yl)-acetic acid (Example 4b, 0.2 g, 0.546 mmol) was dissolved in N,N-dimethylformamide (2.7 mL). 1-(3-Methyl-butylamino)-1H-pyrrole-2-carboxylic acid allyl ester (Example 1c, 0.129 g, 0.546 mmol) was added followed by a 1.0 M solution of N,N-dicyclohexylcarbodiimide in dichloromethane (0.574 mL, 0.574 mmol). The mixture was stirred at 25° C. for 2 h. N,N-Dicyclohexylurea precipitation was visible at this point. The mixture was diluted with dichloromethane (5 mL) and filtered under reduced pressure. The filtrate was washed with 1.0 M aqueous hydrochloric acid solution (2×10 mL), saturated aqueous brine solution (10 mL), dried over magnesium sulfate, filtered and concentrated in vacuo to afford a golden oil. The oil was dissolved in ethanol (2.7 mL). A 21% solution of sodium ethoxide in ethanol (0.448 mL) was added and the mixture was stirred at 80° C. for 4 h. Additional sodium ethoxide in ethanol (0.448 mL) was added and the mixture was stirred at 80° C. for 4 h. Upon cooling to 25° C., the pH was adjusted to approximately 6 by the addition of 3.0 M aqueous hydrochloric acid solution. Immediate precipitation was observed. Methanol (3 mL) was added and the mixture was shaken vigorously. The solid was collected by vacuum filtration, rinsed with methanol (3×2 mL) and dried in vacuo for 16 h to afford the desired product, 4-hydroxy-3-(7-iodo-1,1-dioxo-1,4-dihydro-1$\lambda^6$-benzo[1,2,4]thiadiazin-3-yl)-1-(3-methyl-butyl)-pyrrolo[1,2-b]pyridazin-2-one (0.196 g, 0.372 mmol, 68% yield) as a white powder. LC-MS (ESI) calcd for $C_{19}H_{19}IN_4O_4S$. found 526.02. found 527.15 [M+H$^+$].

b) N-{3-[4-Hydroxy-1-(3-methyl-butyl)-2-oxo-1,2-dihydro-pyrrolo[1,2-b]pyridazin-3-yl]-1,1-dioxo-1,4-dihydro-1$\lambda^6$-benzo[1,2,4]thiadiazin-7-yl}-N-methyl-methanesulfonamide

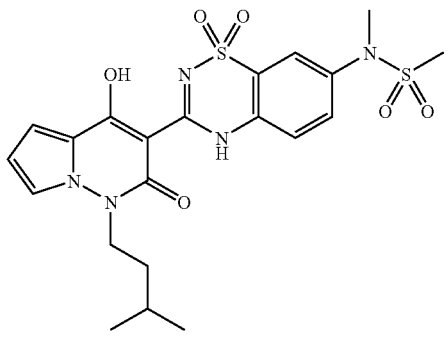

4-Hydroxy-3-(7-iodo-1,1-dioxo-1,4-dihydro-1$\lambda^6$-benzo[1,2,4]thiadiazin-3-yl)-1-(3-methyl-butyl)-pyrrolo[1,2-b]pyridazin-2-one (Example 6a, 0.188 g, 0.357 mmol), potassium triphosphate (0.379 g, 1.78 mmol), sarcosine (0.019 g, 0.214 mmol), and copper (I) iodide (0.017 g, 0.089 mmol) were combined. Anhydrous N,N-dimethylformamide (7 mL) was added followed by N-methyl-methanesulfonamide (0.39 g, 3.57 mmol). The solution was degassed while stirring under vacuum and the flask purged with nitrogen. The mixture was stirred at 100° C. for 1 h. Additional copper (I) iodide (0.1 g, 0.525 mmol) was added. The mixture continued to stir at 100° C. for 3 h. Upon cooling, the mixture was diluted with ethyl acetate (200 mL), washed with 1.0 M aqueous hydrochloric acid solution (2×100 mL), dried over magnesium sulfate, filtered and concentrated in vacuo to a solid. Purification by flash column chromatography (5% ethyl acetate in dichloromethane) followed by trituration from ethyl acetate and collection by vacuum filtration afforded the desired product, N-{3-[4-hydroxy-1-(3-methyl-butyl)-2-oxo-1,2-dihydro-pyrrolo[1,2-b]pyridazin-3-yl]-1,1-dioxo-1,4-dihydro-1$\lambda^6$-benzo[1,2,4]thiadiazin-7-yl}-N-methyl-methanesulfonamide (0.057 g, 0.112 mmol, 31% yield) as a pale yellow powder. $^1$H NMR (400 MHz, DMSO-d$_6$) δ: 0.97 (6H, d, J=6.4 Hz), 1.59 (2H, q, J=7.6 Hz), 1.73 (1H, septet, J=6.5 Hz), 3.01 (3H, s), 3.31 (3H, s), 4.41 (2H, t, J=7.9 Hz), 6.70-6.72 (1H, m), 7.04 (1H, d, J=4.5 Hz), 7.69-7.76 (2H, m), 7.88 (1H, d, J=2.3 Hz), 7.91 (1H, s), 13.79 (1H, bs). LC-MS (ESI) calcd for $C_{21}H_{25}N_5O_6S_2$. found 507.12. found 508.4 [M+H$^+$].

EXAMPLE 7

N-{3-[4-Hydroxy-1-(3-methyl-butyl)-2-oxo-1,2-dihydro-pyrrolo[1,2-b]pyridazin-3-yl]-1,1-dioxo-1,4-dihydro-1$\lambda^6$-benzo[1,4]thiazin-7-yl}-N-methyl-methanesulfonamide

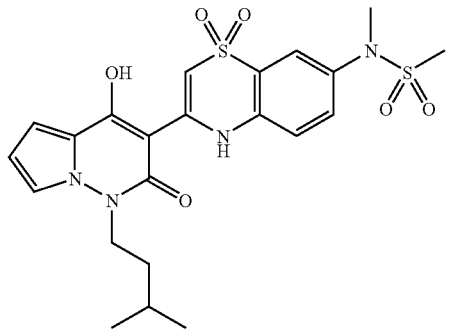

a) N-Benzothiazol-6-yl-methanesulfonamide

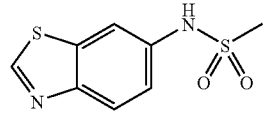

Methanesulfonyl chloride (4.93 mL, 63.7 mmol) was added over 5 min to a solution of benzothiazol-6-ylamine (9.58 g, 63.8 mmol) in pyridine (100 mL) at 25° C. The resulting mixture was stirred at 25° C. for 30 min, and then was concentrated in vacuo. The residue was partitioned between 1.0 M aqueous hydrochloric acid solution (150 mL) and ethyl acetate (2×150 mL). The organic layers were dried over sodium sulfate, filtered and concentrated in vacuo. Trituration of the residue with diethyl ether afforded a solid that was collected by vacuum filtration and dried in vacuo to afford the desired product, N-benzothiazol-6-yl-methanesulfonamide (13.3 g, 58.3 mmol, 91% yield) as a pink solid. $^1$H NMR (400 MHz, DMSO-d$_6$) δ: 3.03 (3H, s), 7.36 (1H, dd, J$_1$=2.3 Hz, J$_2$=8.6 Hz), 7.94 (1H, d, J=1.6 Hz), 8.02 (1H, d, J=9.2 Hz), 9.27 (1H, s), 9.95 (1H, s).

b) N-Benzothiazol-6-yl-N-methyl-methanesulfonamide

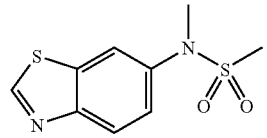

Sodium hydride (2.56 g of a 60% dispersion in mineral oil, 64.0 mmol) was added to a solution of N-benzothiazol-6-ylmethanesulfonamide (Example 7a, 13.3 g, 58.2 mmol) in tetrahydrofuran at 0° C. After 15 min, iodomethane (36.2 mL, 581 mmol) was added and the reaction mixture was warmed to 25° C., stirred for 4 h, then was partitioned between 1.0 M aqueous hydrochloric acid solution (300 mL) and ethyl acetate (2×250 mL). The organic layers were dried over sodium sulfate, filtered and concentrated in vacuo. Trituration of the residue with diethyl ether afforded a solid that was collected by vacuum filtration and dried in vacuo to afford the desired product, N-benzothiazol-6-yl-N-methyl-methanesulfonamide (12.1 g, 50 mmol, 86% yield) as a pink solid. $^1$H NMR (400 MHz, DMSO-$d_6$) δ: 3.00 (3H, s), 3.31 (3H, s), 7.57 (1H, dd, $J_1$=2.2 Hz, $J_2$=8.7 Hz), 8.07 (1H, d, J=8.5 Hz), 8.23 (1H, d, J=1.7 Hz), 9.40 (1H, s).

c) [7-(Methanesulfonyl-methyl-amino)-4H-benzo[1,4]thiazin-3-yl]-acetic acid methyl ester

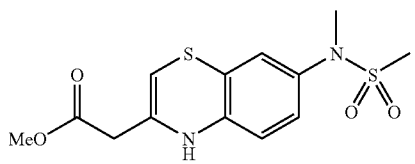

Hydrazine monohydrate (20.1 mL, 414 mmol) was added to a solution of N-benzothiazol-6-yl-N-methyl-methanesulfonamide (Example 7b, 10.06 g, 41.5 mmol) in ethanol (150 mL) at 25° C. The reaction mixture was heated to 50° C. for 13 h, and then was concentrated in vacuo. The residue was dissolved in 1.0 M aqueous hydrochloric acid solution (100 mL) and the pH was adjusted to 7 by the addition of 6.0 M aqueous hydrochloric acid solution. The resulting mixture was extracted with ethyl acetate (2×150 mL) and the aqueous layer was acidified to pH 3 by the addition of 6.0 M aqueous hydrochloric acid solution, and then neutralized to pH 7 by the addition of solid sodium bicarbonate. The mixture was again extracted with ethyl acetate (1×150 mL) and all organic layers were combined, dried over sodium sulfate, filtered and concentrated in vacuo. The orange solid thus obtained was dissolved in tetrahydrofuran (150 mL) and triethylamine (12.3 mL, 88.2 mmol), and 4-chloro-3-oxo-butyric acid methyl ester (5.10 mL, 44.2 mmol) were added sequentially at 25° C. The reaction mixture was stirred at 25° C. for 2 h, and then was partitioned between 1.0 M aqueous hydrochloric acid solution (150 mL) and ethyl acetate (2×150 mL). The organic layers were dried over sodium sulfate, filtered and concentrated in vacuo. Purification of the residue by flash column chromatography (Merck silica gel 60, 40-63 μm, 20→100% ethyl acetate in hexanes) afforded the desired product, [7-(methanesulfonyl-methyl-amino)-4H-benzo[1,4]thiazin-3-yl]-acetic acid methyl ester (8.40 g, 25.6 mmol, 64% yield) as a yellow solid. $^1$H NMR (400 MHz, CDCl$_3$) δ: 2.86 (3H, s), 3.27 (3H, s), 3.43 (2H, s), 3.72 (3H, s), 6.86 (1H, d, J=8.6 Hz), 7.12 (1H, dd, $J_1$=2.3 Hz, $J_2$=8.6 Hz), 7.21 (1H, d, J=2.4 Hz), 10.63 (1H, s).

d) 7-(Methanesulfonyl-methyl-amino)-3-methoxycarbonylmethyl-1,1-dioxo-1H-1λ$^6$-benzo[1,4]thiazine-4-carboxylic acid tert-butyl ester

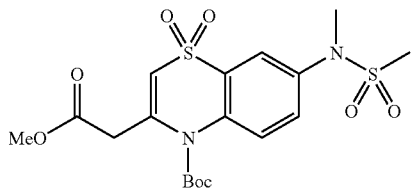

Di-tert-butyl carbonate (11.2 g, 51.1 mmol) and 4-dimethylaminopyridine (0.625 g, 5.11 mmol) were added sequentially to a solution of [7-(methanesulfonyl-methylamino)-4H-benzo[1,4]thiazin-3-yl]-acetic acid methyl ester (Example 7c, 8.40 g, 25.6 mmol) in tetrahydrofuran (100 mL) at 25° C. The reaction mixture was stirred at 25° C. for 15 h, and then was partitioned between 1.0 M aqueous hydrochloric acid solution (150 mL) and ethyl acetate (2×150 mL). The organic layers were dried over sodium sulfate, filtered and concentrated in vacuo. The residue was dissolved in dichloromethane (150 mL) at 25° C. and m-chloroperbenzoic acid (17.2 g, 77% maximum purity, 76.7 mmol) was added. After stirring for 50 min at 25° C., sodium thiosulfate (15 g, dissolved in 150 mL water) was added and the biphasic mixture was stirred at 25° C. for 30 min then poured into a separatory funnel containing a 1:1 mixture of ethyl acetate and hexanes (350 mL). The phases were separated and the organic layer was washed sequentially with 1.0 M aqueous sodium hydroxide solution (100 mL), 1.0 M aqueous hydrochloric acid solution (100 mL), and saturated aqueous sodium bicarbonate solution (100 mL). The organic layer was dried over sodium sulfate, filtered and was concentrated in vacuo. Purification of the residue by flash column chromatography (Merck silica gel 60, 40-63 μm, 20→90% ethyl acetate in hexanes) afforded the desired product, 7-(methanesulfonyl-methyl-amino)-3-methoxycarbonylmethyl-1,1-dioxo-1H-1λ$^6$-benzo[1,4]thiazine-4-carboxylic acid tert-butyl ester (4.29 g, 9.32 mmol, 36% yield) as a yellow foam. $^1$H NMR (400 MHz, CDCl$_3$) (mixture of several isomers/tautomers) δ: 1.51 (s), 1.54 (s), 1.55 (s), 2.87 (s), 2.88 (s), 3.35 (s), 3.37 (s), 3.71 (s), 3.83 (s), 3.87 (s), 5.88 (s), 6.39 (s), 7.64-7.68 (m), 7.77-7.78 (m), 7.83-7.85 (m), 10.02 (s).

e) [7-(Methanesulfonyl-methyl-amino)-1,1-dioxo-1,4-dihydro-1λ$^6$-benzo[1,4]thiazin-3-yl]-acetic acid

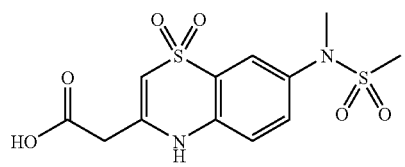

A 2.0 M aqueous solution of lithium hydroxide (7.0 mL, 14.0 mmol) was added to a solution of 7-(methanesulfonyl-methyl-amino)-3-methoxycarbonylmethyl-1-dioxo-1H-1λ$^6$-benzo[1,4]thiazine-4-carboxylic acid tert-butyl ester (Example 7d, 1.29 g, 2.80 mmol) in methanol at 25° C. The reaction mixture was stirred at 25° C. for 5 h, and then was partitioned between 0.5 M aqueous hydrochloric acid solution (150 mL) and ethyl acetate (2×150 mL). The organic layers were dried over sodium sulfate, filtered and concentrated in vacuo. Trituration of the residue with a 5:1 mixture of diethyl ether and acetonitrile afforded the desired product, [7-(methanesulfonyl-methyl-amino)-1,1-dioxo-1,4-dihydro-1λ$^6$-benzo[1,4]thiazin-3-yl]-acetic acid (0.286 g, 0.83 mmol, 30% yield) as an orange solid. $^1$H NMR (400 MHz, DMSO-$d_6$) δ: 2.96 (3H, s), 3.26 (3H, s), 3.48 (2H, s), 6.03 (1H, s), 7.29 (1H, d, J=8.6 Hz), 7.58 (1H, dd, $J_1$=2.3 Hz, $J_2$=9.5 Hz), 7.79 (1H, d, J=2.3 Hz), 10.80 (1H, s), 12.79 (1H, s).

f) N-{3-[4-Hydroxy-1-(3-methyl-butyl)-2-oxo-1,2-dihydro-pyrrolo[1,2-b]pyridazin-3-yl]-1,1-dioxo-1,4-dihydro-1λ⁶-benzo[1,4]thiazin-7-yl}-N-methyl-methanesulfonamide

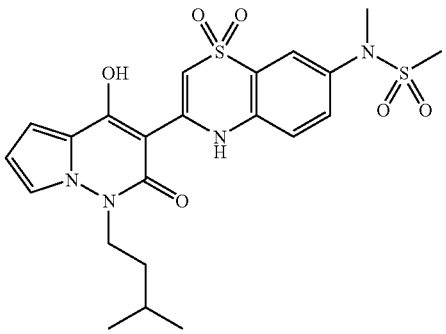

1-(3-Methyl-butylamino)-1H-pyrrole-2-carboxylic acid allyl ester (Example 1c, 0.112 g, 0.473 mmol) and [7-(methanesulfonyl-methyl-amino)-1,1-dioxo-1,4-dihydro-1λ⁶-benzo[1,4]thiazin-3-yl]-acetic acid (Example 7e, 0.164 g, 0.473 mmol) were dissolved in a 3:1 mixture of dichloromethane and N,N-dimethylformamide (4 mL) at 25° C. A solution of N,N-dicyclohexylcarbodiimide (0.473 mL, 1.0 M in dichloromethane, 0.473 mmol) was added and the reaction mixture was stirred at 25° C. for 1 h then filtered. The filtrate was concentrated in vacuo and the residue was dissolved in ethanol (4 mL) at 25° C. A 21% solution of sodium ethoxide in ethanol (0.368 mL, 1.14 mmol) was added and the reaction mixture was heated at 80° C. for 6 h. After cooling to 25° C., the mixture was partitioned between 0.5 M aqueous hydrochloric acid solution (150 mL) and ethyl acetate (2×150 mL). The organic layers were dried over sodium sulfate, filtered and concentrated in vacuo. Sequential purification of the residue by flash column chromatography (Merck silica gel 60, 40-63 μm, 50→100% ethyl acetate in hexanes) and preparative HPLC [column=Luna 5μ C18(2) 100 Å Axia 50×21.2 mm Id; eluent=0→100% acetonitrile in water (both containing 0.05% trifluoroacetic acid) over 7.0 min, flow=30 mL/min] afforded the desired product, N-{3-[4-hydroxy-1-(3-methyl-butyl)-2-oxo-1,2-dihydro-pyrrolo[1,2-b]pyridazin-3-yl]-1,1-dioxo-1,4-dihydro-1λ⁶-benzo[1,4]thiazin-7-yl}-N-methyl-methanesulfonamide (0.060 g, 0.119 mmol, 25% yield) as a yellow solid. ¹H NMR (400 MHz, DMSO-d₆) δ: 0.94 (6H, d, J=6.4 Hz), 1.50-1.54 (2H, m), 1.64-1.70 (1H, m), 2.99 (3H, bs), 3.28 (3H, bs), 4.29-4.32 (2H, m), 5.74 (1H, s), 6.12 (1H, bs), 6.49 (1H, bs), 6.90 (1H, bs), 7.30 (1H, bs), 7.60 (1H, bs), 7.82 (1H, bs). LC-MS (ESI) calcd for C₂₂H₂₆N₄O₆S₂ 506.13. found 507.25 [M+H⁺].

EXAMPLE 8

N-{3-[1-(3,3-Dimethyl-butyl)-4-hydroxy-2-oxo-1,2-dihydro-pyrrolo[1,2-b]pyridazin-3-yl]-1,1-dioxo-1,4-dihydro-1λ⁶-benzo[1,4]thiazin-7-yl}-methanesulfonamide

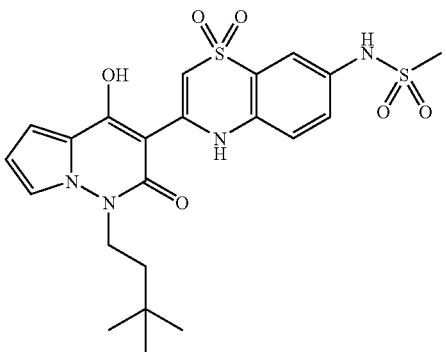

a) 2-Amino-5-nitro-benzenethiol

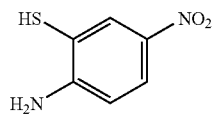

A solution of 6-nitrobenzothiazole (5 g, 27.7 mmol) in ethanol (50 mL) was treated with mono hydrazine hydrate (19 g, 388 mmol). The reaction mixture was stirred for 3 h at 25° C. and concentrated in vacuo. The resulting red oil was taken up in ethyl acetate, carefully acidified with 0.1 M aqueous hydrochloric acid solution until the solution turned light yellow. The reaction mixture was extracted with ethyl acetate, dried over magnesium sulfate, filtered, and concentrated in vacuo. The resulting orange solid was triturated with diethyl ether and dried in vacuo to afford the desired product, 2-amino-5-nitro-benzenethiol (4.1 g, 23.9 mmol, 86% yield) as a yellow solid. ¹H NMR (400 MHz, Acetone-d₆) δ 6.43 (bs, 2H), 6.82 (d, 1H, J=8.7 Hz), 7.65 (d, 1H, J=2.2 Hz), 7.88 (dd, 1H, J₁=8.9 Hz, J₂=2.7 Hz). LC-MS (ESI) calcd for C₆H₆N₂O₂S [M+H⁺] 171.01. found 193.20 [M+Na⁺].

b) (7-Nitro-4H-benzo[1,4]thiazin-3-yl)-acetic acid ethyl ester

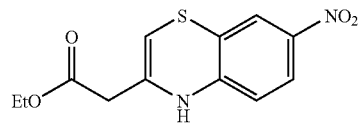

A solution of 2-amino-5-nitro-benzenethiol (Example 8a, 4.1 g, 23.9 mmol) in tetrahydrofuran (60 mL) was treated with triethylamine (4.8 g, 47.8 mmol) and ethyl chloroacetoacetate (4.3 g, 26.3 mmol). The reaction mixture was stirred at 25° C. for 12 h, concentrated in vacuo, taken up in ethyl acetate, and heated at 80° C. for 3 h. The reaction mixture was allowed to cool to 25° C., washed with brine solution, dried over sodium sulfate, and concentrated in vacuo. The resulting brown solid was triturated with diethyl ether to afford the desired product, (7-nitro-4H-benzo[1,4]thiazin-3-yl)-acetic acid ethyl ester (5.8 g, 20.7 mmol, 87% yield) as a yellow solid. ¹H NMR (400 MHz, CDCl₃) δ 1.32 (t, 3H, J=7.1 Hz), 3.49 (s, 2H), 4.21 (q, 2H, J=7.0 Hz), 4.89 (s, 1H), 6.91 (d, 1H, J=8.7 Hz), 8.00 (dd, 1H, J₁=9.5 Hz, J₂=2.3 Hz), 8.12 (d, 1H, J=3.1 Hz), 10.95 (bs, 1H). LC-MS (ESI) calcd for C₁₂H₁₂N₂O₄S [M+H⁺] 281.05. found 281.23 [M+H⁺].

c) (7-Amino-4H-benzo[1,4]thiazin-3-yl)-acetic acid ethyl ester

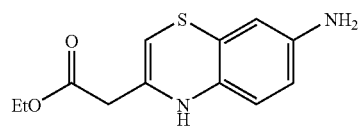

A solution of (7-nitro-4H-benzo[1,4]thiazin-3-yl)-acetic acid ethyl ester (Example 8b, 5.8 g, 20.7 mmol) in ethanol (90 mL) was treated with tin (II) chloride and 1.0 M aqueous hydrochloric acid solution (3 mL). The reaction was heated at 100° C. for 3 h. The suspension was allowed to cool and concentrated. The crude material was suspended in ethyl acetate (90 mL) and treated with 6.0 M aqueous sodium hydroxide solution (90 mL). The resulting precipitate was filtered. The filter cake was thoroughly washed with ethyl acetate, the filtrated was washed with brine solution, and concentrated in vacuo. The crude oil was purified by flash chromatography (Merck silica gel 60, 40-63 μm, ethyl acetate/hexanes) to afford the desired product, (7-amino-4H-benzo[1,4]thiazin-3-yl)-acetic acid ethyl ester (2.38 g, 9.51 mmol, 46% yield) as a white solid. $^1$H NMR (400 MHz, CDCl$_3$) δ 1.21 (t, 3H, J=7.1 Hz), 3.30 (s, 2H), 3.43 (bs, 2H), 4.08 (q, 2H, J=7.1 Hz), 4.52 (s, 1H), 6.39 (dd, 1H, $J_1$=8.3 Hz, $J_2$=2.7 Hz), 6.46 (d, 1H, J=2.3 Hz), 6.62 (d, 1H, J=7.6 Hz), 10.38 (bs, 1H). LC-MS (ESI) calcd for $C_{12}H_{14}N_2O_2S$ [M+H$^+$] 251.08. found 251.23 [M+H$^+$].

d) (7-Methanesulfonylamino-4H-benzo[1,4]thiazin-3-yl)-acetic acid ethyl ester

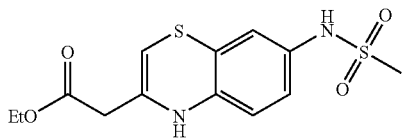

A solution of (7-amino-4H-benzo[1,4]thiazin-3-yl)-acetic acid ethyl ester (Example 8c, 2.38 g, 9.51 mmol) in dichloromethane (80 mL) was cooled to 0° C. and treated with triethylamine (3.1 g, 30.4 mmol) followed by dropwise addition of methanesulfonyl chloride (1.37 g, 9.51 mmol). The reaction mixture was stirred at 0° C. for 0.5 h and allowed to warm to 25° C. The reaction mixture was concentrated in vacuo and purified by flash chromatography (Merck silica gel 60, 40-63 μm, ethyl acetate/hexanes) to afford the desired product, (7-methanesulfonylamino-4H-benzo[1,4]thiazin-3-yl)-acetic acid ethyl ester (2.2 g, 6.7 mmol, 71% yield) as a light tan solid. $^1$H NMR (400 MHz, CDCl$_3$) δ 1.31 (t, 3H, J=7.0 Hz), 3.00 (s, 3H), 3.43 (s, 2H), 4.19 (quartet, 2H, J=7.1 Hz), 4.73 (s, 1H), 6.28 (s, 1H), 6.85 (d, 1H, J=8.5 Hz), 6.99 (dd, 1H, $J_1$=8.5 Hz, $J_2$=2.4 Hz), 7.12 (d, 1H, J=2.3 Hz), 10.64 (bs, 1H). LC-MS (ESI) calcd for $C_{13}H_{16}N_2O_4S$ [M+H$^+$] 329.06. found 329.10 [M+H$^+$].

e) [7-(Methanesulfonyl-tert-butyloxycarbonyl-amino)-4-tert-butyloxycarbonyl-4H-benzo[1,4]thiazin-3-yl]-acetic acid ethyl ester

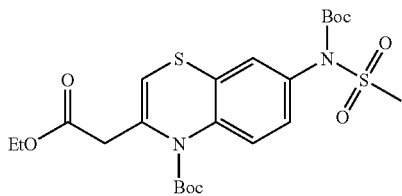

A solution of (7-methanesulfonylamino-4H-benzo[1,4]thiazin-3-yl)-acetic acid ethyl ester (Example 8d, 2.2 g, 6.7 mmol) in anhydrous tetrahydrofuran (60 mL) was treated with di-tert-butyl-dicarbonate (3.2 g, 14.7 mmol) and 4-(dimethylamino)pyridine (0.82 g, 6.7 mmol). The reaction mixture was stirred at 25° C. under a nitrogen atmosphere for 3 h. The solvent was removed in vacuo and the residue was dissolved in dichloromethane. The resulting solution was washed with 1.0 M aqueous hydrochloric acid solution, the organic layer was dried over sodium sulfate, filtered, and concentrated in vacuo. The crude oil was purified by flash chromatography (Merck silica gel 60, 40-63 μm, ethyl acetate/hexanes) to afford the desired product, [7-(methanesulfonyl-tert-butyloxycarbonyl-amino)-4-tert-butyloxycarbonyl-4H-benzo[1,4]thiazin-3-yl]-acetic acid ethyl ester (1.59 g, 3.01 mmol, 45% yield) as a colorless resin. $^1$H NMR (400 MHz, CDCl$_3$) δ 1.16 (t, 3H, J=7.0 Hz), 1.48 (s, 9H), 1.52 (s, 9H), 3.42 (s, 3H), 3.67 (bs, 2H), 4.07 (q, 2H, J=7.3 Hz), 6.26 (s, 1H), 7.09 (1H, $J_1$=0.0 Hz, $J_2$=0.0 Hz), 7.08-7.11 (m, 2H), 7.42 (d, 1H, J=7.8 Hz). LC-MS (ESI) calcd for $C_{23}H_{32}N_2O_8S_2$ [M+H$^+$] 529.16. found 429.48 [M-Boc$^+$].

f) [7-(Methanesulfonyl-tert-butyloxycarbonyl-amino)-4-tert-butyloxycarbonyl-1,1-dioxo-1,4-dihydro-1λ$^6$-benzo[1,4]thiazin-3-yl]-acetic acid ethyl ester

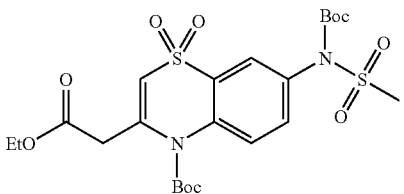

A solution of [7-(methanesulfonyl-tert-butyloxycarbonyl-amino)-4-tert-butyloxycarbonyl-4H-benzo[1,4]thiazin-3-yl]-acetic acid ethyl ester (Example 8e, 1.59 g, 3.01 mmol) in dichloromethane (50 mL) was treated with 3-chloroperoxybenzoic acid (2.23 g, 12.9 mmol). The reaction mixture was stirred for 12 h at 25° C. A solution of aqueous sodium thiosulfate (2.0 g, 12.9 mmol) was added, and the reaction was stirred for an additional 0.5 h. The organic layer was separated, washed sequentially with 1.0 M aqueous sodium hydroxide solution, 1.0 M aqueous hydrochloric acid solution, saturated aqueous sodium bicarbonate solution, and brine, dried over sodium sulfate, filtered, and concentrated in vacuo. The crude oil was purified by flash chromatography (Merck silica gel 60, 40-63 μm, ethyl acetate/hexanes) to afford the desired product, [7-(methanesulfonyl-tert-butyloxycarbonyl-amino)-4-tert-butyloxycarbonyl-1,1-dioxo-1,4-dihydro-1λ$^6$-benzo[1,4]thiazin-3-yl]-acetic acid ethyl ester (1.1 g, 1.96 mmol, 64% yield) as a white solid. $^1$H NMR (400 MHz, CDCl$_3$) δ 1.23 (t, 3H, J=7.0 Hz), 1.50 (s, 9H), 1.56 (s, 9H), 3.46 (s, 3H), 3.81 (s, 2H), 4.15 (q, 2H, J=7.4 Hz), 6.40 (s, 1H), 7.45 (dd, 1H, $J_1$=9.1 Hz, $J_2$=2.7 Hz), 7.72 (d, 1H, J=2.3 Hz), 7.91 (d, 1H, J=8.6 Hz). LC-MS (ESI) calcd for $C_{23}H_{32}N_2O_8S_2$ [M+H$^+$] 560.16. found 361.18 [M−(2× Boc)$^+$].

g) (7-Methanesulfonylamino-1,1-dioxo-1,4-dihydro-1λ$^6$-benzo[1,4]thiazin-3-yl)-acetic acid ethyl ester

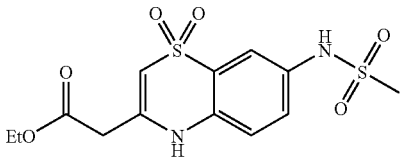

A solution of [7-(methanesulfonyl-tert-butyloxycarbonyl-amino)-4-tert-butyloxycarbonyl-1,1-dioxo-1,4-dihydro-1λ$^6$-benzo[1,4]thiazin-3-yl]-acetic acid ethyl ester (Example 8f, 0.30 g, 0.54 mmol) in 1:1 dichloromethane/trifluoroacetic acid was stirred at 25° C. for 2 h. The reaction mixture was concentrated in vacuo and the residue was dissolved in ethyl acetate. The solution was washed with saturated aqueous sodium bicarbonate solution and brine solution. The organic layer was dried over sodium sulfate, filtered, and concentrated in vacuo to afford the desired product, (7-methanesulfonylamino-1,1-dioxo-1,4-dihydro-1λ$^6$-benzo[1,4]thiazin-3-yl)-acetic acid ethyl ester (0.17 g, 0.47 mmol, 86% yield) as a yellow solid. $^1$H NMR (400 MHz, CDCl$_3$) δ 1.32 (t, 3H, J=6.9 Hz), 3.03 (s, 3H), 4.02 (s, 2H), 4.21 (q, 2H, J=7.0 Hz), 5.02 (s, 1H), 6.96 (s, 1H), 7.02 (d, 1H, J=8.4 Hz), 7.53 (dd, 1H, J$_1$=8.7 Hz, J$_2$=2.4 Hz), 7.65 (d, 1H, J=2.2 Hz), 10.73 (s, 1H). LC-MS (ESI) calcd for $C_{13}H_{16}N_2O_6S_2$ [M+H$^+$] 361.04. found 361.18 [M+H$^+$].

h) (7-Methanesulfonylamino-1,1-dioxo-1,4-dihydro-1λ$^6$-benzo[1,4]thiazin-3-yl)-acetic acid

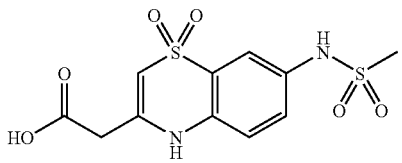

A solution of (7-methanesulfonylamino-1,1-dioxo-1,4-dihydro-1λ$^6$-benzo[1,4]thiazin-3-yl)-acetic acid ethyl ester (Example 8g, 0.245 g, 0.680 mmol) in methanol (15 mL) was cooled to 0° C. in an ice-water bath and treated with 2.0 M aqueous lithium hydroxide solution (1.7 mL, 3.40 mmol). The reaction mixture was allowed to warm to 25° C. and stirred for 1 h. The reaction was poured into 0.5 M aqueous hydrochloric acid solution (50 mL) on ice, extracted with ethyl acetate (3×50 mL), dried over magnesium sulfate, filtered, and concentrated in vacuo to give an orange solid. The crude solid was triturated with diethyl ether to afford the desired product, (7-methanesulfonylamino-1,1-dioxo-1,4-dihydro-1λ$^6$-benzo[1,4]thiazin-3-yl)-acetic acid (0.175 g, 0.526 mmol, 77% yield) as a light orange solid. LC-MS (ESI) calcd for $C_{11}H_{12}N_2O_6S_2$ 332.4. found 333.3 [M+H$^+$].

i) N-{3-[1-(3,3-Dimethyl-butyl)-4-hydroxy-2-oxo-1,2-dihydro-pyrrolo[1,2-b]pyridazin-3-yl]-1,1-dioxo-1,4-dihydro-1λ$^6$-benzo[1,4]thiazin-7-yl}-methanesulfonamide

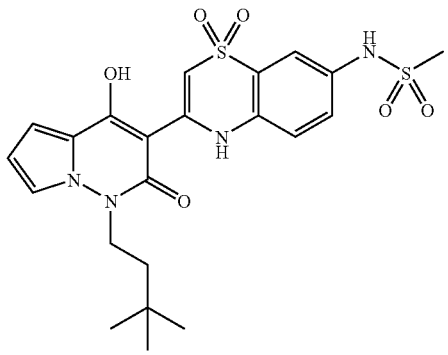

N,N-Dicyclohexylcarbodiimide (0.476 mL of a 1.0 M solution in dichloromethane, 0.476 mmol) was added to a solution of (7-methanesulfonylamino-1,1-dioxo-1,4-dihydro-1λ$^6$-benzo[1,4]thiazin-3-yl)-acetic acid (Example 8h, 0.190 g, 0.572 mmol) and 1-(3,3-dimethyl-butylamino)-1H-pyrrole-2-carboxylic acid allyl ester (Example 4c, 0.119 g, 0.475 mmol) in a 3:1 mixture of dichloromethane and N,N-dimethylformamide (6 mL) at 25° C. The reaction mixture was stirred at 25° C. for 1 h then was filtered. The filtrate was concentrated in vacuo and the residue was dissolved in ethanol (12 mL) at 25° C. A 21% solution of sodium ethoxide in ethanol (0.23 mL, 0.71 mmol) was added and the reaction mixture was heated at 80° C. for 5 h. After cooling to 25° C., the mixture was partitioned between 1.0 M aqueous hydrochloric acid solution (150 mL) and ethyl acetate (2×150 mL). The organic layers were dried over sodium sulfate, filtered and concentrated in vacuo. Purification of the residue by flash column chromatography (Merck silica gel 60, 40-63 μm, 40→100% ethyl acetate in hexanes) afforded a solid which was triturated with diethyl ether to afford the desired product, N-{3-[1-(3,3-dimethyl-butyl)-4-hydroxy-2-oxo-1,2-dihydro-pyrrolo[1,2-b]pyridazin-3-yl]-1,1-dioxo-1,4-dihydro-1λ$^6$-benzo[1,4]thiazin-7-yl}-methanesulfonamide (0.101 g, 0.20 mmol, 42% yield) as a yellow solid. $^1$H NMR (400 MHz, CDCl$_3$) δ: 1.07 (9H, s), 1.65-1.72 (2H, m), 3.09 (3H, s), 4.25-4.29 (2H, m), 5.54 (2H, s), 6.43-6.45 (1H, m), 7.01-7.03 (1H, m), 7.08-7.09 (1H, m), 7.30 (1H, d, J=8.5 Hz), 7.39 (1H, bs), 7.61 (1H, dd, J$_1$=2.3 Hz, J$_2$=8.6 Hz), 7.73 (1H, d, J=2.4 Hz). LC-MS (ESI) calcd for $C_{22}H_{26}N_4O_6S_2$ 506.13. found 507.27 [M+H$^+$].

EXAMPLE 9

N-{3-[1-(4-Fluoro-benzyl)-4-hydroxy-2-oxo-1,2-dihydro-pyrrolo[1,2-b]pyridazin-3-yl]-1,1-dioxo-1,4-dihydro-1λ$^6$-benzo[1,2,4]thiadiazin-7-yl}-methanesulfonamide

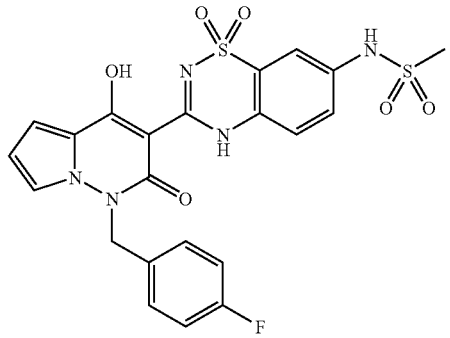

a) 1-(4-Fluoro-benzylamino)-1H-pyrrole-2-carboxylic acid allyl ester

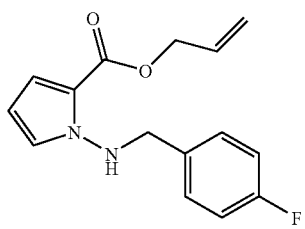

Sodium cyanoborohydride (2.29 g, 36.4 mmol) was added to a solution of 1-amino-1H-pyrrole-2-carboxylic acid allyl ester (Example 1b, 3.03 g, 18.2 mmol), 4-fluorobenzaldehyde (1.96 mL, 18.3 mmol) and acetic acid (6 mL), in methanol (120 mL) at 25° C. The reaction mixture was stirred at 25° C. for 18 h, and then was concentrated in vacuo to a volume of about 30 mL. The remaining liquid was partitioned between half-saturated aqueous sodium bicarbonate solution (150 mL) and a 1:1 mixture of ethyl acetate and hexanes (2×200 mL). The organic layers were dried over sodium sulfate, filtered and concentrated in vacuo. Purification of the residue by flash column chromatography (Merck silica gel 60, 40-63 μm, 0→40% ethyl acetate in hexanes) afforded the desired product, 1-(4-fluoro-benzylamino)-1H-pyrrole-2-carboxylic acid allyl ester (1.87 g, 6.8 mmol, 37% yield) as a clear liquid.

$^1$H NMR (400 MHz, CDCl$_3$) δ: 4.08 (2H, d, J=5.4 Hz), 4.75-4.77 (1H, m), 5.27-5.30 (1H, m), 5.37-5.41 (1H, m), 5.95-5.97 (1H, m), 5.98-6.05 (1H, m), 6.58-6.61 (1H, m), 6.75-6.76 (1H, m), 6.89-6.91 (1H, m), 6.97-7.01 (2H, m), 7.22-7.25 (2H, m).

b) 1-(4-Fluoro-benzyl)-4-hydroxy-3-(7-iodo-1,1-dioxo-1,4-dihydro-1λ$^6$-benzo[1,2,4]thiadiazin-3-yl)-pyrrolo[1,2-b]pyridazin-2-one

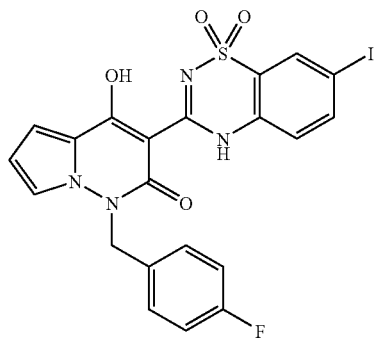

N,N-Dicyclohexylcarbodiimide (4.33 mL of a 1.0 M solution in dichloromethane, 4.33 mmol) was added to a solution of (7-iodo-1,1-dioxo-1,4-dihydro-1λ$^6$-benzo[1,2,4]thiadiazin-3-yl)-acetic acid (Example 4b, 1.58 g, 4.32 mmol) and 1-(4-fluoro-benzylamino)-1H-pyrrole-2-carboxylic acid allyl ester (Example 9a, 1.08 g, 3.94 mmol) in a 4:1 mixture of dichloromethane and N,N-dimethylformamide (25 mL) at 25° C. The reaction mixture was stirred at 25° C. for 2.5 h then was filtered. The filtrate was concentrated in vacuo and the residue was dissolved in ethanol (20 mL) at 25° C. A 21% solution of sodium ethoxide in ethanol (8.0 mL, 24.6 mmol) was added and the reaction mixture was heated at 80° C. for 8 h. After cooling to 25° C., the mixture was partitioned between 1.0 M aqueous hydrochloric acid solution (150 mL) and ethyl acetate (2×150 mL). The organic layers were dried over sodium sulfate, filtered and concentrated in vacuo to give a dark solid. Trituration of this material with methanol afforded a grey solid that was collected by vacuum filtration to afford the desired product, 1-(4-fluoro-benzyl)-4-hydroxy-3-(7-iodo-1,1-dioxo-1,4-dihydro-1λ$^6$-benzo[1,2,4]thiadiazin-3-yl)-pyrrolo[1,2-b]pyridazin-2-one (1.42 g, 2.52 mmol, 64% yield). $^1$H NMR (400 MHz, DMSO-d$_6$) δ: 5.64 (2H, s), 6.58-6.60 (1H, m), 7.01-7.02 (1H, m), 7.14-7.18 (2H, m), 7.42-7.46 (2H, m), 7.70-7.70 (1H, m), 8.02-8.04 (1H, m), 8.12-8.12 (1H, m), 13.70 (1H, s).

c) N-{3-[1-(4-Fluoro-benzyl)-4-hydroxy-2-oxo-1,2-dihydro-pyrrolo[1,2-b]pyridazin-3-yl]-1,1-dioxo-1,4-dihydro-1λ$^6$-benzo[1,2,4]thiadiazin-7-yl}-methanesulfonamide

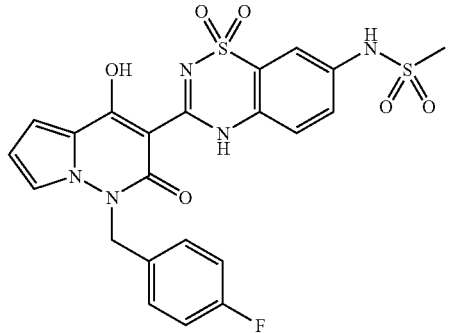

1-(4-Fluoro-benzyl)-4-hydroxy-3-(7-iodo-1,1-dioxo-1,4-dihydro-1λ$^6$-benzo[1,2,4]thiadiazin-3-yl)-pyrrolo[1,2-b]pyridazin-2-one (Example 9b, 0.257 g, 0.455 mmol), potassium phosphate (tribasic) (0.483 g, 2.28 mmol), copper(I) iodide (0.022 g, 0.11 mmol), sarcosine (0.024 g, 0.273 mmol, and methanesulfonamide (0.433 g, 4.55 mmol) were dissolved in N,N-dimethylformamide (9 mL) at 25° C. The mixture was heated to 100° C. for 6 h, then was allowed to cool to 25° C., diluted with ethyl acetate (10 mL), and filtered through Celite. The filtrate was concentrated in vacuo and the residue was purified by flash column chromatography (Merck silica gel 60, 40-63 μm, 0→10% methanol in dichloromethane) to afford a yellow solid. Sequential trituration of this material with methanol and diethyl ether afforded the desired product, N-{3-[1-(4-fluoro-benzyl)-4-hydroxy-2-oxo-1,2-dihydro-pyrrolo[1,2-b]pyridazin-3-yl]-1,1-dioxo-1,4-dihydro-1λ$^6$-benzo[1,2,4]thiadiazin-7-yl}-methanesulfonamide (0.113 g, 0.21 mmol, 47% yield) as a yellow solid. $^1$H NMR (400 MHz, DMSO-d$_6$) δ: 3.08 (3H, s), 5.65 (2H, s), 6.59-6.61 (1H, m), 7.01-7.02 (1H, m), 7.14-7.18 (2H, m), 7.42-7.46 (2H, m), 7.54 (1H, dd, J$_1$=2.3 Hz, J$_2$=8.6 Hz), 7.62 (1H, d, J=2.5 Hz), 7.66 (1H, d, J=8.9 Hz), 7.71 (1H, s), 10.21 (1H, s), 13.66 (1H, s). LC-MS (ESI) calcd for C$_{22}$H$_{18}$FN$_5$O$_6$S$_2$ 531.07. found 532.10 [M+H$^+$].

EXAMPLE 10

N-{3-[1-(4-Fluoro-benzyl)-4-hydroxy-2-oxo-1,2-dihydro-pyrrolo[1,2-b]pyridazin-3-yl]-1-dioxo-1,4-dihydro-1λ$^6$-benzo[1,2,4]thiadiazin-7-yl}-N-methyl-methanesulfonamide

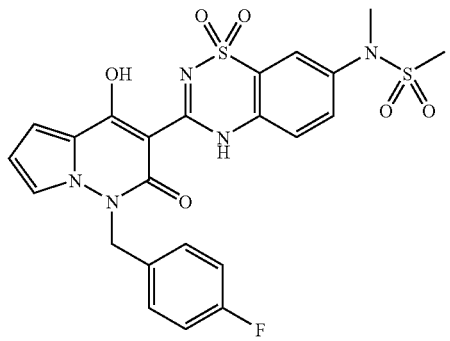

1-(4-Fluoro-benzyl)-4-hydroxy-3-(7-iodo-1,1-dioxo-1,4-dihydro-1λ$^6$-benzo[1,2,4]thiadiazin-3-yl)-pyrrolo[1,2-b]pyridazin-2-one (Example 9b, 0.269 g, 0.477 mmol), potassium phosphate (tribasic) (0.506 g, 2.38 mmol), copper(I) iodide (0.023 g, 0.119 mmol), sarcosine (0.026 g, 0.290 mmol, and N-methyl-methanesulfonamide (0.520 g, 4.77 mmol) were dissolved in N,N-dimethylformamide (9 mL) at 25° C. The mixture was heated to 100° C. for 6 h, then was allowed to cool to 25° C., diluted with ethyl acetate (10 mL), and filtered through Celite. The filtrate was concentrated in vacuo and the residue was purified by flash column chromatography (Merck silica gel 60, 40-63 μm, 0→10% methanol in dichloromethane) to afford a yellow solid. Sequential trituration of this material with methanol and diethyl ether afforded the desired product, N-{3-[1-(4-fluoro-benzyl)-4-hydroxy-2-oxo-1,2-dihydro-pyrrolo[1,2-b]pyridazin-3-yl]-1,1-dioxo-1,4-dihydro-1λ$^6$-benzo[1,2,4]thiadiazin-7-yl}-N-methyl-methanesulfonamide (0.169 g, 0.31 mmol, 65% yield) as a yellow solid. $^1$H NMR (400 MHz, DMSO-d$_6$) δ: 3.02 (3H, s), 3.31 (3H, s), 5.65 (2H, s), 6.59-6.61 (1H, m), 7.01-7.03 (1H, m), 7.14-7.19 (2H, m), 7.42-7.46 (2H, m), 7.68-7.71 (2H, m), 7.75 (1H, dd, J$_1$=2.4 Hz, J$_2$=8.7 Hz), 7.90 (1H, d, J=2.2 Hz), 13.72 (1H, s). LC-MS (ESI) calcd for C$_{23}$H$_{20}$FN$_5$O$_6$S$_2$ 545.08. found 546.15 [M+H$^+$].

EXAMPLE 11

3-[7-(1,1-Dioxo-tetrahydro-1λ$^6$-thiophen-2-yl)-1,1-dioxo-1,4-dihydro-1λ$^6$-benzo[1,2,4]thiadiazin-3-yl]-1-(4-fluoro-benzyl)-4-hydroxy-pyrrolo[1,2-b]pyridazin-2-one

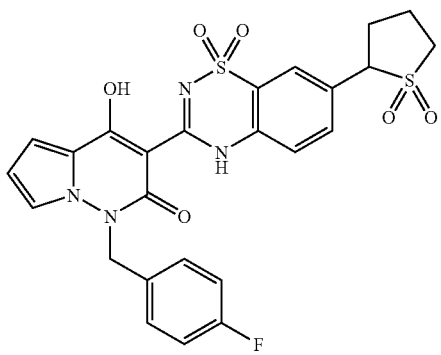

a) Tributyl-(1,1-dioxo-4,5-dihydro-1H-1λ$^6$-thiophen-2-yl)-stannane

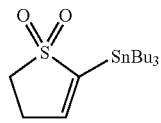

n-Butyllithium (6.72 mL of a 1.6 M solution in hexanes, 10.7 mmol) was added over 5 min to a solution of 2,3-dihydro-thiophene 1,1-dioxide (1.21 g, 10.2 mmol, prepared as described in *J. Organomet. Chem.*, 665, 167 (2003)) in tetrahydrofuran (60 mL) at −78° C. The reaction mixture was stirred at −78° C. for 30 min, then tributyltin chloride (3.04 mL, 11.2 mmol) was added over 5 min. After stirring at −78° C. for 45 min, the mixture was warmed to 25° C. and stirred for an additional 45 min then was concentrated in vacuo. The residue was diluted with chloroform (50 mL) and filtered. The filtrate was partitioned between water (100 mL) and a 1:1 mixture of ethyl acetate and hexanes (1×200 mL). The organic layer was dried over sodium sulfate, filtered and was concentrated in vacuo. Purification of the residue by flash column chromatography (Merck silica gel 60, 40-63 μm, 20→30% ethyl acetate in hexanes) afforded the desired product, tributyl-(1,1-dioxo-4,5-dihydro-1H-1λ$^6$-thiophen-2-yl)-stannane (1.13 g, 2.77 mmol, 27% yield) as a yellow solid. $^1$H NMR (400 MHz, CDCl$_3$) δ: 0.90-0.95 (9H, m), 1.15-1.21 (6H, m), 1.29-1.40 (8H, m), 1.50-1.67 (6H, m), 2.96-3.00 (1H, m), 3.11-3.14 (1H, m), 6.57 (1H, t, J=3.1 Hz).

b) 3-[7-(1,1-Dioxo-4,5-dihydro-1H-1λ$^6$-thiophen-2-yl)-1,1-dioxo-1,4-dihydro-1λ$^6$-benzo[1,2,4]thiadiazin-3-yl]-1-(4-fluoro-benzyl)-4-hydroxy-pyrrolo[1,2-b]pyridazin-2-one

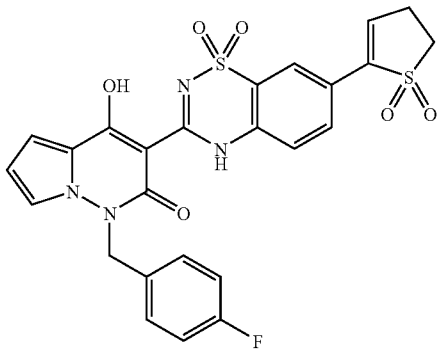

1-(4-Fluoro-benzyl)-4-hydroxy-3-(7-iodo-1,1-dioxo-1,4-dihydro-1λ$^6$-benzo[1,2,4]thiadiazin-3-yl)-pyrrolo[1,2-b]pyridazin-2-one (Example 9b, 0.207 g, 0.371 mmol), tributyl-(1,1-dioxo-4,5-dihydro-1H-1λ$^6$-thiophen-2-yl)-stannane (Example 11a, 0.181 g, 0.442 mmol) and tetrakis(triphenylphosphine)palladium(0) (0.025 g, 0.020 mmol) were dissolved in N,N-dimethylformamide (8 mL) at 25° C. The mixture was heated to 90° C. for 24 h, then was allowed to cool to 25° C. and filtered through Celite. The filtrate was concentrated in vacuo and the residue was purified by flash column chromatography (Merck silica gel 60, 40-63 μm, 0→7% methanol in dichloromethane) to afford a brown solid. This material was re-chromatographed (Merck silica gel 60, 40-63 μm, 40→100% ethyl acetate in hexanes, followed by 100% ethyl acetate, followed by 0→7% methanol in dichloromethane) to afford the desired product, 3-[7-(1,1-dioxo-4,5-dihydro-1H-1λ$^6$-thiophen-2-yl)-1,1-dioxo-1,4-dihydro-1λ$^6$-benzo[1,2,4]thiadiazin-3-yl]-1-(4-fluoro-benzyl)-4-hydroxy-pyrrolo[1,2-b]pyridazin-2-one (0.100 g, 0.180 mmol, 48.6% yield). LC-MS (ESI) calcd for C$_{25}$H$_{19}$FN$_4$O$_6$S$_2$ 554.07. found 555.00 [M+H$^+$].

c) 3-[7-(1,1-Dioxo-tetrahydro-1λ⁶-thiophen-2-yl)-1,1-dioxo-1,4-dihydro-1λ⁶-benzo[1,2,4]thiadiazin-3-yl]-1-(4-fluoro-benzyl)-4-hydroxy-pyrrolo[1,2-b]pyridazin-2-one

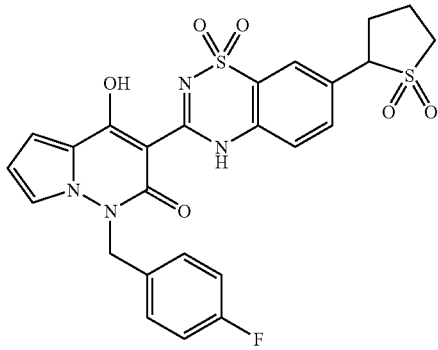

3-[7-(1,1-Dioxo-4,5-dihydro-1H-1λ⁶-thiophen-2-yl)-1,1-dioxo-1,4-dihydro-1λ⁶-benzo[1,2,4]thiadiazin-3-yl]-1-(4-fluoro-benzyl)-4-hydroxy-pyrrolo[1,2-b]pyridazin-2-one (Example 11b, 0.100 g, 0.180 mmol) was dissolved in N,N-dimethylformamide (15 mL) at 25° C. Palladium on carbon (5%, 0.250 g) was added and the atmosphere in the reaction flask replaced with hydrogen from a balloon. After stirring for 1 h under a hydrogen balloon, the mixture was filtered through Celite. The filtrate was concentrated in vacuo and the residue was purified by flash column chromatography (Merck silica gel 60, 40-63 μm, 0→3% methanol in dichloromethane) to afford a yellow solid. Trituration of this material with diethyl ether afforded the desired product, 3-[7-(1,1-dioxo-tetrahydro-1λ⁶-thiophen-2-yl)-1,1-dioxo-1,4-dihydro-1λ⁶-benzo[1,2,4]thiadiazin-3-yl]-1-(4-fluoro-benzyl)-4-hydroxy-pyrrolo[1,2-b]pyridazin-2-one (0.028 g, 0.050 mmol, 28% yield). $^1$H NMR (400 MHz, DMSO-$d_6$) δ: 2.08-2.18 (1H, m), 2.23-2.29 (1H, m), 2.32-2.43 (1H, m), 3.20-3.28 (1H, m), 3.31-3.37 (1H, m), 4.56-4.61 (1H, m), 5.65 (2H, s), 6.60 (2H, d, J=7.0 Hz), 6.59-6.61 (1H, m), 7.02-7.03 (1H, m), 7.14-7.18 (2H, m), 7.42-7.46 (1H, m), 7.67-7.75 (2H, m), 7.87 (1H, bs), 13.73 (1H, s). LC-MS (ESI) calcd for $C_{25}H_{21}FN_4O_6S_2$ 556.09. found 557.15 [M+H⁺].

EXAMPLE 12

3-(1,1-Dioxo-1,4-dihydro-1λ⁶-benzo[1,2,4]thiadiazin-3-yl)-1-(4-fluoro-benzyl)-4-hydroxy-pyrrolo[1,2-b]pyridazin-2-one

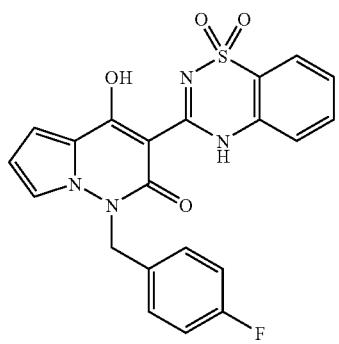

3-(1,1-Dioxo-1,4-dihydro-1λ⁶-benzo[1,2,4]thiadiazin-3-yl)-1-(4-fluoro-benzyl)-4-hydroxy-pyrrolo[1,2-b]pyridazin-2-one was obtained as a by-product from the reaction described in Example 11b. Column chromatography as described above afforded the desired product, 3-(1,1-dioxo-1,4-dihydro-1λ⁶-benzo[1,2,4]thiadiazin-3-yl)-1-(4-fluoro-benzyl)-4-hydroxy-pyrrolo[1,2-b]pyridazin-2-one (0.020 g, 0.046 mmol, 8.1% yield) as a yellow solid. $^1$H NMR (400 MHz, DMSO-$d_6$) δ: 5.65 (2H, s), 6.59 (1H, bs), 7.00-7.01 (1H, m), 7.14-7.18 (2H, m), 7.42-7.46 (2H, m), 7.48-7.52 (1H, m), 7.60-7.62 (1H, m), 7.69-7.75 (2H, m), 7.87-7.89 (1H, m), 13.69 (1H, s). LC-MS (ESI) calcd for $C_{21}H_{15}FN_4O_4S_2$ 438.08. found 439.20 [M+H⁺].

EXAMPLE 13

Cyclopropanesulfonic acid {3-[4-hydroxy-1-(3-methyl-butyl)-2-oxo-1,2-dihydro-pyrrolo[1,2-b]pyridazin-3-yl]-1,1-dioxo-1,4-dihydro-1λ⁶-benzo[1,2,4]thiadiazin-7-yl}-amide

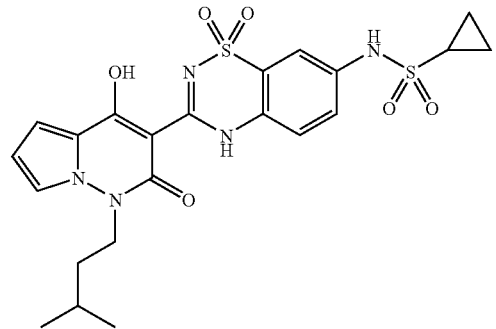

a) 4-Hydroxy-3-(7-iodo-1,1-dioxo-1,4-dihydro-1λ⁶-benzo[1,2,4]thiadiazin-3-yl)-1-(3-methyl-butyl)-pyrrolo[1,2-b]pyridazin-2-one

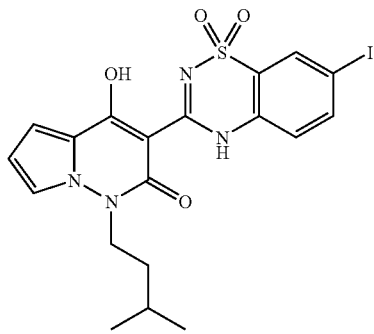

4-Hydroxy-1-(3-methyl-butyl)-2-oxo-1,2-dihydro-pyrrolo[1,2-b]pyridazine-3-carboxylic acid ethyl ester (Example 1f, 0.218 g, 0.75 mmol) was dissolved in pyridine (1.5 mL) and 2-amino-5-iodo-benzenesulfonamide (Example 4a, 0.222 g, 0.75 mmol) was added. The reaction mixture was heated at 120° C. for 16 h, and then 1,8-diazabicyclo[5.4.0]undec-7-ene (0.12 mL, 0.78 mmol) was added an heated for another 4 h. The pyridine was removed in vacuo to afford the crude desired product. Purification by flash column chromatography (Merck silica gel 60, 40-63 μm, 5%-10% methanol in dichloromethane) afforded the desired product, 4-hydroxy-3-(7-iodo-1,1-dioxo-1,4-dihydro-1λ⁶-benzo[1,2,4]thiadiazin-3-yl)-1-(3-methyl-butyl)-pyrrolo[1,2-b]pyridazin-2-one (0.110 g, 0.209 mmol, 28% yield) as a white solid. LC-MS (ESI) calcd for $C_{19}H_{19}IN_4O_4S$. found 526.02. found 527.20 [M+H⁺].

b) Cyclopropanesulfonic acid {3-[4-hydroxy-1-(3-methyl-butyl)-2-oxo-1,2-dihydro-pyrrolo[1,2-b]pyridazin-3-yl]-1,1-dioxo-1,4-dihydro-1λ⁶-benzo[1,2,4]thiadiazin-7-yl}-amide

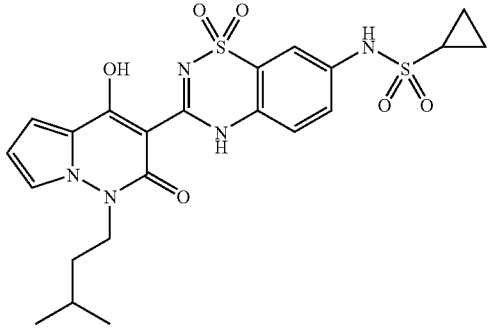

4-Hydroxy-3-(7-iodo-1,1-dioxo-1,4-dihydro-1λ⁶-benzo[1,2,4]thiadiazin-3-yl)-1-(3-methyl-butyl)-pyrrolo[1,2-b]pyridazin-2-one (Example 13a, 0.105 g, 0.199 mmol), potassium triphosphate (0.127 g, 0.598 mmol), sarcosine (0.011 g, 0.119 mmol), and copper (I) iodide (0.015 g, 0.080 mmol) were combined. Anhydrous N,N-dimethylformamide (7 mL) was added followed by cyclopropanesulfonic acid amide (0.12 g, 1 mmol). The solution was degassed while stirring under vacuum and the flask purged with nitrogen. The mixture was stirred at 100° C. for 16 h. Upon cooling, the mixture was diluted with ethyl acetate (200 mL), washed with 1.0 M aqueous hydrochloric acid solution (2×100 mL), dried over magnesium sulfate, filtered and concentrated in vacuo to a solid. Purification by HPLC (Column Luna 5u C18 (2) 100 Å size 50×21.2 mm, 5 micron, 40%-95% 0.05% trifluoroacetic acid in acetonitrile/0.05% trifluoroacetic acid in water) afforded the desired product, cyclopropanesulfonic acid {3-[4-hydroxy-1-(3-methyl-butyl)-2-oxo-1,2-dihydro-pyrrolo[1,2-b]pyridazin-3-yl]-1,1-dioxo-1,4-dihydro-1λ⁶-benzo[1,2,4]thiadiazin-7-yl}-amide (0.052 g, 0.10 mmol, 50% yield) as a pale yellow powder. $^1$H NMR (400 MHz, DMSO-$d_6$) δ: 0.97 (10H, m), 1.51 (2H, q, J=7.2 Hz), 1.73 (1H, m), 2.71 (1H, m), 4.41 (2H, t, J=7.6 Hz), 6.72 (1H, m), 7.02 (1H, d, J=3.6 Hz), 7.58 (1H, m), 7.63 (2H, m), 7.88 (1H, s), 10.12 (1H, bs). LC-MS (ESI) calcd for $C_{22}H_{25}N_5O_6S_2$. found 519.12. found 520.3 [M+H⁺].

EXAMPLE 14

N-{3-[6-Fluoro-4-hydroxy-1-(3-methyl-butyl)-2-oxo-1,2-dihydro-pyrrolo[1,2-b]pyridazin-3-yl]-1,1-dioxo-1,4-dihydro-1λ⁶-benzo[1,2,4]thiadiazin-7-yl}-methanesulfonamide

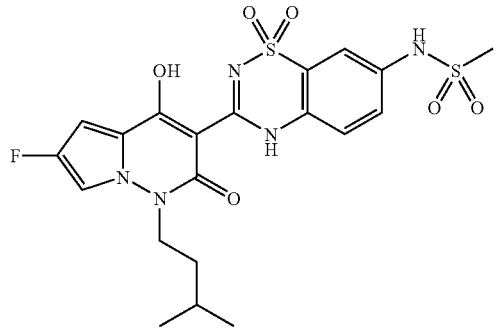

a) 4,4-Difluoro-pyrrolidine-1,2-dicarboxylic acid 1-tert-butyl ester 2-methyl ester

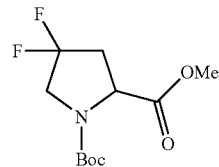

4,4-Difluoro-pyrrolidine-1,2-dicarboxylic acid 1-tert-butyl ester 2-methyl ester was prepared as described in *Tetrahedron Lett.*, 44, 7809-12 (2003). 4-Oxo-pyrrolidine-1,2-dicarboxylic acid 1-tert-butyl ester 2-methyl ester (7.12 g, 29.287 mmol) was dissolved in dichloromethane (150 mL) and cooled to −78° C. N,N-Diethylaminosulfur trifluoride (23.58 g, 146.436 mmol) was slowly added to the stirred solution over a period of 5 min. The reaction was allowed to warm to 25° C. over 16 h. The reaction mixture was poured into ice (200 mL) and the layers were separated. The organic layer was washed with water and saturated aqueous sodium bicarbonate solution, dried over sodium sulfate and filtered. The solvent was removed in vacuo to afford the crude desired product, 4,4-difluoro-pyrrolidine-1,2-dicarboxylic acid 1-tert-butyl ester 2-methyl ester (1.90 g, 7.167 mmol, 58.1% yield), as a yellow oil, which was in the next step without further purification. $^1$H NMR (400 MHz, CDCl$_3$) δ: 1.44 (9H, s), 2.47 (1H, qd, $J_1$=13.3 Hz, $J_2$=4.9 Hz), 2.63-2.78 (1H, m), 3.75-3.96 (5H, m), 4.50 (5H, dm, $J_1$=40.4 Hz, $J_2$=0.0 Hz), 4.43-4.57 (1H, m).

b) 4,4-Difluoro-pyrrolidine-1,2-dicarboxylic acid 1-tert-butyl ester

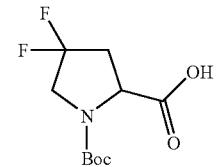

4,4-Difluoro-pyrrolidine-1,2-dicarboxylic acid 1-tert-butyl ester 2-methyl ester (Example 14a, 7.53 g, 28.403 mmol) was dissolved in acetonitrile (330 mL) and a solution of lithium hydroxide (1.36 g, 56.807 mmol) in water (110 mL) was added. After stirring for 16 h at 25° C., the acetonitrile was removed in vacuo and the aqueous phase was slowly acidified with 1.0 M aqueous hydrochloric acid solution until a precipitate formed. The product was extracted into ethyl acetate (3×50 mL) and the combined organic layers were dried over sodium sulfate and filtered. The solvent was removed in vacuo to afford the desired product, 4,4-difluoro-pyrrolidine-1,2-dicarboxylic acid 1-tert-butyl ester (1.54 g, 6.13 mmol, 95.6% yield) as a brittle, tan solid, which was used in the next step without further purification. $^1$H NMR (400 MHz, CDCl$_3$) δ: 1.51 (9H, s), 2.50-2.84 (2H, m), 3.71-3.90 (2H, m), 6.73 (1H, bs).

c) 4,4-Difluoro-pyrrolidine-1,2-dicarboxylic acid 2-allyl ester 1-tert-butyl ester

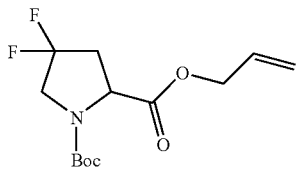

4,4-Difluoro-pyrrolidine-1,2-dicarboxylic acid 1-tert-butyl ester (Example 14b, 6.77 g, 26.96 mmol) was dissolved in a 5% aqueous sodium bicarbonate solution (50 mL). Allyl bromide (3.26 g, 26.96 mmol) and trioctylmethylammonium chloride ("Aliquat 336", 10.90 g, 26.97 mmol) were dissolved in dichloromethane (50 mL) and were added to the aqueous solution. The biphasic reaction mixture was stirred vigorously for 48 h at 25° C. The layers were separated and the aqueous layer was extracted with dichloromethane (3×70 mL). The combined organic layers were dried over sodium sulfate and filtered. The solvent was removed in vacuo to afford the crude desired product, which was purified by flash column chromatography (Merck silica gel 60, 40-63 μm, 20% ethyl acetate in hexanes) to afford the desired product, 4,4-difluoro-pyrrolidine-1,2-dicarboxylic acid 2-allyl ester 1-tert-butyl ester (5.85 g, 20.09 mmol, 74.5% yield) as a clear, slightly yellowish oil. $^1$H NMR (400 MHz, CDCl$_3$) δ: 1.44 (9H, s), 2.43-2.54 (1H, m), 2.64-2.80 (1H, m), 3.78-3.94 (2H, m), 4.46-4.73 (3H, m), 5.24-5.37 (2H, m), 5.87-5.96 (1H, m).

d) 4,4-Difluoro-pyrrolidine-2-carboxylic acid allyl ester trifluoroacetic acid salt

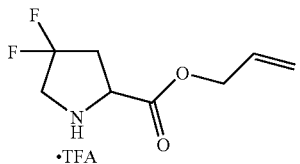

4,4-Difluoro-pyrrolidine-1,2-dicarboxylic acid 2-allyl ester 1-tert-butyl ester (Example 14c, 5.85 g, 20.09 mmol) was dissolved in a 5% solution of trifluoroacetic acid in dichloromethane and stirred at 25° C. for 16 h. The solvent was removed in vacuo and the crude 4,4-difluoro-pyrrolidine-2-carboxylic acid allyl ester (6.14 g, 20.09 mmol, 100% yield) was obtained as the trifluoroacetic acid salt, which was used in the next step without further purification. $^1$H NMR (400 MHz, CDCl$_3$) δ: 2.75-2.86 (1H, m), 2.90-3.02 (1H, m), 3.76-3.93 (2H, m), 4.68-4.78 (3H, m), 5.33-5.39 (2H, m), 5.84-5.94 (1H, m).

e) 4-Fluoro-1H-pyrrole-2-carboxylic acid allyl ester

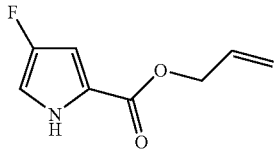

To a solution of 4,4-Difluoro-pyrrolidine-2-carboxylic acid allyl ester trifluoroacetic acid salt (Example 14d, 6.13 g, 20.08 mmol) in anhydrous tetrahydrofuran (300 mL) was added manganese(IV) dioxide and the reaction mixture was heated at 80° C. for 4 h. The mixture was filtered over Celite, and was washed with hot and then cold tetrahydrofuran. The filtrate was concentrated in vacuo to give a dark orange oil. The oil was dissolved in ethyl acetate and the organic layer was washed with saturated aqueous sodium bicarbonate solution. The solvent was removed in vacuo to give an orange oil, which was purified by flash column chromatography (Merck silica gel 60, 40-63 μm, 30% ethyl acetate in hexanes) to afford the desired product, 4-fluoro-1H-pyrrole-2-carboxylic acid allyl ester (3.01 g, 17.80 mmol, 88.7% yield) as a yellow oil. $^1$H NMR (400 MHz, CDCl$_3$) δ: 4.77 (2H, d, J=5.7 Hz), 5.29 (1H, d, J=10.2 Hz), 5.38 (1H, d, J=15.9 Hz), 5.94-6.04 (1H, m), 6.64-6.65 (1H, m), 6.72-6.74 (1H, m), 8.91 (1H, bs).

f) 1-Amino-4-fluoro-1H-pyrrole-2-carboxylic acid allyl ester

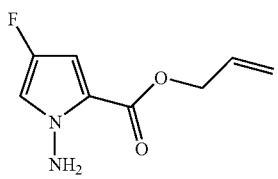

1-Amino-4-fluoro-1H-pyrrole-2-carboxylic acid allyl ester was prepared following the N-amination procedure described in *Tetrahedron Lett.*, 47, 5341-43 (2006). 4-Fluoro-1H-pyrrole-2-carboxylic acid allyl ester (Example 14e, 2.49 g, 14.74 mmol) was mixed together with solid ammonium chloride (4.81 g, 90.75 mmol), 30% aqueous sodium hydroxide solution (42.4 mL), 29.56% aqueous ammonium hydroxide solution (13.71 mL) and trioctylmethylammonium chloride ("Aliquat® 336", 0.166 g, 0.411 mmol) in methyl tert-butyl ether (50 mL). Under vigorous stirring, a 6.15% aqueous bleach solution ("Chlorox", 146 mL) was slowly added via addition funnel upon which the color of the solution turned orange. After stirring for 2 h at 25° C., the layers were separated and the aqueous layer was extracted with methyl tert-butyl ether (2×10 mL). The combined organic layers were washed with a saturated sodium thiosulfate solution (50 mL) and the organic layer was dried over sodium sulfate and filtered. The solvent was removed in vacuo and the crude product was purified by flash column chromatography (Merck silica gel 60, 40-63 μm, 20% ethyl acetate in hexanes) to afford the desired product, 1-amino-4-fluoro-1H-pyrrole-2-carboxylic acid allyl ester (2.02 g, 10.99 mmol, 62.1% yield). $^1$H NMR (400 MHz, CDCl$_3$) δ: 4.73 (2H, d, J=5.5 Hz), 5.26-5.29 (1H, m), 5.34-5.40 (1H, m), 5.52 (2H, bs), 5.93-6.02 (1H, m), 6.49-6.53 (1H, m), 6.78-6.80 (1H, m).

g) 4-Fluoro-1-(3-methyl-butylamino)-1H-pyrrole-2-carboxylic acid allyl ester

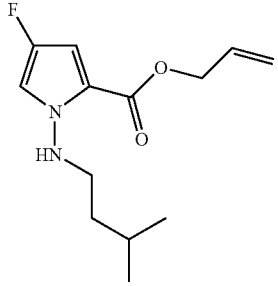

To a solution of 1-amino-4-fluoro-1H-pyrrole-2-carboxylic acid allyl ester (Example 14f, 0.5 g, 2.717 mmol) in metha nol (20 mL) were added isovaleraldehyde (0.257 g, 2.988 mmol) and sodium cyanoborohydride (0.256 g, 4.075 mmol). The mixture was stirred for 20 h at 25° C. The solvent was removed in vacuo and the crude product was purified by flash column chromatography (Merck silica gel 60, 40-63 μm, 20% ethyl acetate in hexanes) to afford the desired product, 4-fluoro-1-(3-methyl-butylamino)-1H-pyrrole-2-carboxylic acid allyl ester (0.264 g, 1.039 mmol, 38.2% yield) as a yellow oil. $^1$H NMR (400 MHz, CDCl$_3$) δ: 0.91 (3H, s), 0.93 (3H, s), 1.38-1.45 (2H, m), 1.63-1.80 (1H, m), 3.00-3.05 (2H, m), 4.74-4.76 (1H, m), 5.29 (1H, d, J=10.4 Hz), 5.38 (1H, d, J=18.8 Hz), 5.94-6.03 (1H, m), 6.52-6.56 (1H, m), 6.79-6.81 (1H, m).

h) 1-[(2-Methoxycarbonyl-acetyl)-(3-methyl-butyl)-amino]-4-fluoro-1H-pyrrole-2-carboxylic acid allyl ester

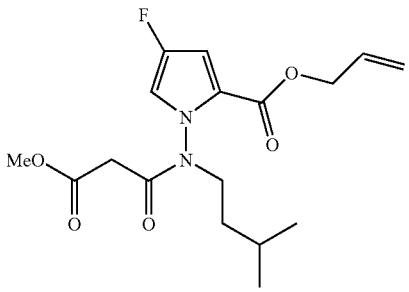

4-Fluoro-1-(3-methyl-butylamino)-1H-pyrrole-2-carboxylic acid allyl ester (Example 14g, 0.24 g, 0.944 mmol) was dissolved in anhydrous 1,4-dioxane (10 mL) and methyl malonyl chloride was added under a nitrogen atmosphere. The reaction mixture was heated to 100° C. for 1 h. Upon cooling to 25° C., saturated aqueous sodium bicarbonate solution was added and the product was extracted with 50% ethyl acetate/hexanes. The combined organic layers were dried over sodium sulfate, filtered and concentrated in vacuo to afford the crude desired product, 1-[(2-ethoxycarbonyl-acetyl)-(3-methyl-butyl)-amino]-4-fluoro-1H-pyrrole-2-carboxylic acid allyl ester (0.335 g, 0.944 mmol, 100% yield) as a pale yellow oil, which was used in the next step without further purification. $^1$H NMR (400 MHz, CDCl$_3$) δ: 0.90 (3H, d, J=4.6 Hz), 0.92 (3H, d, J=5.2 Hz), 1.37-1.46 (1H, m), 1.54-1.64 (1H, m), 1.69-1.78 (1H, m), 3.13 (2H, d, J=3.1 Hz), 3.70 (3H, s), 4.16-4.26 (2H, m), 4.73 (2H, d, J=5.5 Hz), 5.28-5.31 (1H, m), 5.37 (1H, dd, J$_1$=17.2 Hz, J$_2$=1.6 Hz), 5.91-6.01 (1H, m), 6.69-6.76 (2H, m).

i) 6-Fluoro-4-hydroxy-1-(3-methyl-butyl)-2-oxo-1,2-dihydro-pyrrolo[1,2-b]pyridazine-3-carboxylic acid ethyl ester

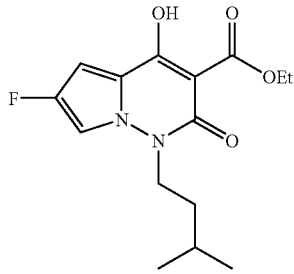

To a solution of 1-[(2-ethoxycarbonyl-acetyl)-(3-methyl-butyl)-amino]-4-fluoro-1H-pyrrole-2-carboxylic acid allyl ester (Example 14h, 0.318 g, 0.898 mmol) in ethanol (10 mL) was added a 21% solution of sodium ethoxide in ethanol (0.728 g, 2.245 mmol) and the mixture was heated at 40° C. for 16 h. The solvent was removed in vacuo and the residue was purified by flash column chromatography (Merck silica gel 60, 40-63 μm, 20% ethyl acetate in hexanes, then 10% methanol in dichloromethane) to afford the desired product, 6-fluoro-4-hydroxy-1-(3-methyl-butyl)-2-oxo-1,2-dihydro-pyrrolo[1,2-b]pyridazine-3-carboxylic acid ethyl ester (0.137 g, 0.441 mmol, 49.1% yield) as a yellow oil. $^1$H NMR (400 MHz, CDCl$_3$) δ: 0.99 (3H, s), 1.00 (3H, s), 1.44 (3H, t, J=7.0 Hz), 1.58-1.63 (2H, m), 1.67-1.75 (1H, m), 4.18-4.22 (2H, m), 4.44 (2H, quartet, J=7.1 Hz), 6.55 (1H, m), 7.04 (1H, m).

j) 6-Fluoro-4-hydroxy-3-(7-iodo-1,1-dioxo-1,4-dihydro-1λ$^6$-benzo[1,2,4]thiadiazin-3-yl)-1-(3-methyl-butyl)-pyrrolo[1,2-b]pyridazin-2-one

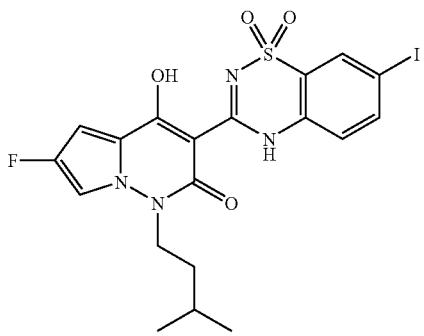

6-Fluoro-4-hydroxy-1-(3-methyl-butyl)-2-oxo-1,2-dihydro-pyrrolo[1,2-b]pyridazine-3-carboxylic acid ethyl ester (Example 14i, 136.7 mg, 0.441 mmol) and 2-amino-5-iodo-benzenesulfonamide (Example 4a, 131.3 mg, 0.441 mmol) were mixed in anhydrous pyridine (2 mL) and heated at 120° C. for 3 h. 1,8-Diazabicyclo[5.4.0]undec-7-ene (200 μL) was added and the mixture was heated at 120° C. for 16 h. Purification by flash column chromatography (Merck silica gel 60, 40-63 μm, 20% ethyl acetate in hexanes) afforded the desired product, 6-fluoro-4-hydroxy-3-(7-iodo-1,1-dioxo-1,4-dihydro-1λ$^6$-benzo[1,2,4]thiadiazin-3-yl)-1-(3-methyl-butyl)-pyrrolo[1,2-b]pyridazin-2-one (0.047 g, 0.086 mmol, 19.5% yield) as a dark purple solid. LC-MS (ESI) calcd for C$_{19}$H$_{18}$FIN$_4$O$_4$S 544.01. found 544.97 [M+H$^+$].

k) N-{3-[6-Fluoro-4-hydroxy-1-(3-methyl-butyl)-2-oxo-1,2-dihydro-pyrrolo[1,2-b]pyridazin-3-yl]-1,1-dioxo-1,4-dihydro-1λ$^6$-benzo[1,2,4]thiadiazin-7-yl}-methanesulfonamide

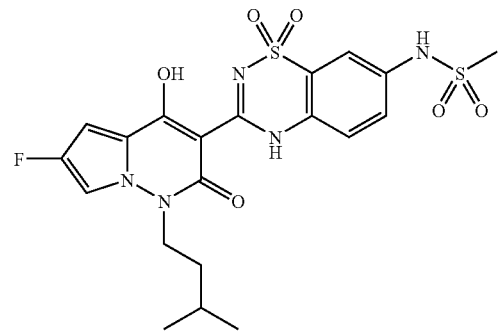

6-Fluoro-4-hydroxy-3-(7-iodo-1,1-dioxo-1,4-dihydro-1λ$^6$-benzo[1,2,4]thiadiazin-3-yl)-1-(3-methyl-butyl)-pyrrolo[1,2-b]pyridazin-2-one (Example 14j, 0.047 g, 0.086 mmol), potassium triphosphate (0.055 g, 0.258 mmol), sarcosine (0.0046 g, 0.0516 mmol), and copper (I) iodide (0.0066 g, 0.0344 mmol) were combined. Anhydrous N,N-dimethylformamide (3 mL) was added followed by methanesulfonamide (0.0245 g, 0.258 mmol). The flask was purged with nitrogen and the mixture was stirred at 100° C. for 16 h. Upon cooling, the mixture was filtered over Celite, washed with ethyl acetate and the solvent was removed in vacuo. Purification by preparative HPLC (Column Luna 5μ C18 (2) 100 Å size 150×21.2 mm, 5 micron, 40%-95% in 11 min 25 mL/min flow rate, 0.05% trifluoroacetic acid in acetonitrile/ 0.05% trifluoroacetic acid in water) afforded the desired product, N-{3-[6-fluoro-4-hydroxy-1-(3-methyl-butyl)-2-oxo-1,2-dihydro-pyrrolo[1,2-b]pyridazin-3-yl]-1,1-dioxo-1,4-dihydro-1$\lambda^6$-benzo[1,2,4]thiadiazin-7-yl}-methanesulfonamide (0.0068 g, 0.0133 mmol, 15.4% yield) as a solid. $^1$H NMR (400 MHz, DMSO-$d_6$) δ: 0.96 (3H, s), 0.97 (3H, s), 1.53-1.59 (2H, m), 1.66-1.76 (1H, m), 3.07 (3H, s), 4.32 (2H, t, J=7.5 Hz), 6.83 (1H, bs), 7.51-7.63 (3H, m), 8.06 (1H, bs), 10.17 (1H, bs). LC-MS (ESI) calcd for $C_{20}H_{22}FN_5O_6S_2$ 511.10. found 512.3 [M+H$^+$].

EXAMPLE 15

N-{3-[6-Cyano-4-hydroxy-1-(3-methyl-butyl)-2-oxo-1,2-dihydro-pyrrolo[1,2-b]pyridazin-3-yl]-1,1-dioxo-1,4-dihydro-1$\lambda^6$-benzo[1,2,4]thiadiazin-7-yl}-methanesulfonamide

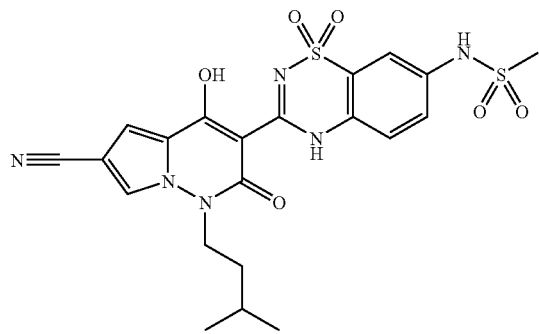

a) 4-Cyano-1H-pyrrole-2-carboxylic acid methyl ester

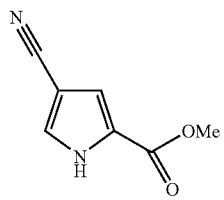

4-Cyano-1H-pyrrole-2-carboxylic acid methyl ester was prepared as described in *Can. J. Chem.*, 59, 2673-76 (1981). 1H-Pyrrole-2-carboxylic acid methyl ester (2.00 g, 16.00 mmol) was dissolved in acetonitrile (5 mL) and the solution was cooled to −20° C. Chlorosulfonylisocyanate (3.40 g, 24.00 mmol) was dissolved in acetonitrile (5 mL) and added dropwise via syringe over a period of 5 min to the above solution. The solution was allowed to warm to 25° C. and was stirred for 20 h. The solution was cooled back to 0° C., N,N-dimethylformamide (2 mL) was added and the solution was heated to 50° C. for 15 min. The reaction mixture was poured into ice and was extracted with chloroform, washed with saturated aqueous sodium bicarbonate solution, dried over sodium sulfate, filtered and concentrated in vacuo. Purification by flash column chromatography (Merck silica gel 60, 40-63 μm, 40% ethyl acetate in hexanes) afforded the desired product, 4-cyano-1H-pyrrole-2-carboxylic acid methyl ester (1.09 g, 7.265 mmol, 45.4% yield) as an off-white solid. $^1$H NMR (400 MHz, CDCl$_3$) δ: 3.91 (3H, s), 7.12 (1H, t, J=2.0 Hz), 7.40-7.41 (1H, m), 9.60 (1H, bs). FT-IR (ATR) $v_{max}$ (neat): 2228, 1691 cm$^{-1}$.

b) 1-Amino-4-cyano-1H-pyrrole-2-carboxylic acid methyl ester

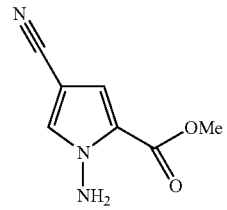

Solid ammonium chloride (5.8 g, 109.4 mmol) was suspended in diethyl ether (300 mL) and the suspension was cooled to −5° C. To this were added 29.56% aqueous ammonium hydroxide solution (16 mL) and 6.15% aqueous bleach solution ("Chlorox", 240 mL) over a period of 15 min. The mixture was stirred for 30 min at −5° C. and then the layers were separated. The organic layer was washed with brine, filtered over sodium sulfate and stored over solid calcium chloride at −5° C. 4-Cyano-1H-pyrrole-2-carboxylic acid methyl ester (Example 15a, 1.09 g, 7.265 mmol) was dissolved in N,N-dimethylformamide (30 mL) and a 60% dispersion of sodium hydride in mineral oil (0.378 g, 9.445 mmol) was added. After stirring for 1 h at 25° C., the above ~0.36 M solution of monochloramine in ether (26 mL, 9.445 mmol) was added and stirred for 2 h at 25° C. The reaction was quenched with saturated aqueous sodium thiosulfate solution followed by water. The layers were separated and the aqueous layer was extracted with diethyl ether. The combined organic layers were dried over sodium sulfate, filtered and concentrated in vacuo to afford the crude desired product, 1-amino-4-cyano-1H-pyrrole-2-carboxylic acid methyl ester, which was used in the next step without further purification. $^1$H NMR (400 MHz, CDCl$_3$) δ: 3.88 (3H, s), 5.67 (2H, bs), 7.07 (1H, d, J=1.7 Hz), 7.37 (1H, d, J=1.7 Hz).

c) 4-Cyano-1-(3-methyl-butylamino)-1H-pyrrole-2-carboxylic acid methyl ester

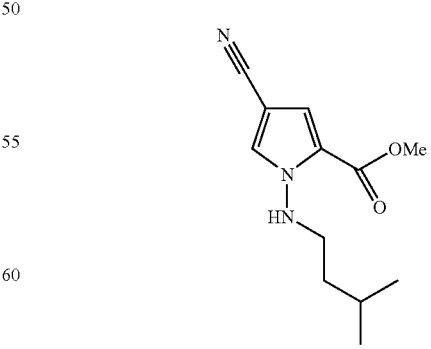

The crude 1-amino-4-cyano-1H-pyrrole-2-carboxylic acid methyl ester (Example 15b, 0.60 g, 3.635 mmol) and isovaleraldehyde (0.313 g, 3.635 mmol) were dissolved in isopropanol (15 mL) and heated at 50° C. for 72 h. The solvent was removed in vacuo to afford the imine as a yellowish oil. The intermediate was dissolved in methanol (20 mL) and sodium borohydride (0.206 g, 5.453 mmol) was added. After stirring at 25° C. for 30 min, the reaction was quenched with 1.0 M sodium hydroxide solution. The aqueous layer was extracted with ethyl acetate and the combined organic layers were dried over sodium sulfate, filtered and concentrated in vacuo. Purification by flash column chromatography (Merck silica gel 60, 40-63 μm, 40% ethyl acetate in hexanes) afforded the desired product, 4-cyano-1-(3-methyl-butylamino)-1H-pyrrole-2-carboxylic acid methyl ester (0.604 g, 2.591 mmol, 71.3% yield) as a yellowish oil. $^1$H NMR (400 MHz, CDCl$_3$) δ: 0.92 (3H, s), 0.94 (3H, s), 1.37-1.43 (2H, m), 1.64-1.74 (1H, m), 2.99-3.04 (2H, m), 3.88 (3H, s), 6.40 (1H, t, J=6.3 Hz), 7.09 (1H, d, J=1.5 Hz), 7.36 (1H, d, J=2.2 Hz). LC-MS (ESI) calcd for $C_{12}H_{17}N_3O_2$ 235.13. found 236.3 [M+H$^+$].

d) 4-Cyano-1-[(2-ethoxycarbonyl-acetyl)-(3-methyl-butyl)-amino]-1H-pyrrole-2-carboxylic acid methyl ester

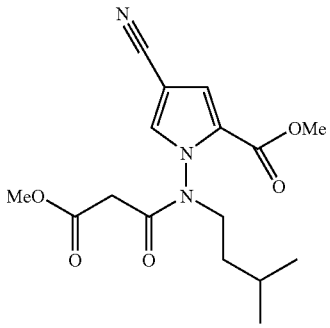

To a solution of 4-cyano-1-(3-methyl-butylamino)-1H-pyrrole-2-carboxylic acid methyl ester (Example 15c, 0.600 g, 2.552 mmol) in anhydrous 1,4-dioxane (25 mL) was added methyl malonyl chloride (0.383 g, 2.807 mmol) and the reaction mixture was heated at 100° C. for 3 h. Upon cooling, the reaction was quenched with saturated aqueous sodium bicarbonate solution and was extracted with 50% ethyl acetate/hexanes (3×30 mL). The combined organic layers were dried over sodium sulfate, filtered and concentrated in vacuo to afford the crude desired product, 4-cyano-1-[(2-ethoxycarbonyl-acetyl)-(3-methyl-butyl)-amino]-1H-pyrrole-2-carboxylic acid methyl ester as a yellowish oil, which was used in the next step without further purification. LC-MS (ESI) calcd for $C_{16}H_{21}N_3O_5$ 335.15. found 336.4 [M+H$^+$].

e) 6-Cyano-4-hydroxy-1-(3-methyl-butyl)-2-oxo-1,2-dihydro-pyrrolo[1,2-b]pyridazine-3-carboxylic acid ethyl ester

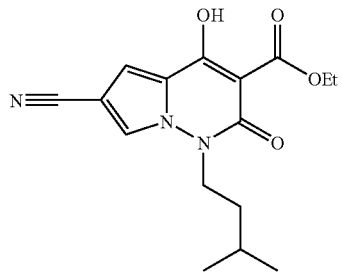

To a solution of crude 4-cyano-1-[(2-ethoxycarbonyl-acetyl)-(3-methyl-butyl)-amino]-1H-pyrrole-2-carboxylic acid methyl ester (Example 15d, 2.552 mmol) in ethanol (30 mL) was added a 21% solution of sodium ethoxide in ethanol (2.07 g, 6.380 mmol) and the mixture was heated at 40° C. for 16 h. Upon cooling, the mixture was quenched with 1.0 M aqueous hydrochloric acid solution and brine. The aqueous mixture was extracted with ethyl acetate and the combined organic layers were dried over sodium sulfate, filtered and concentrated in vacuo to afford the crude desired product, 6-cyano-4-hydroxy-1-(3-methyl-butyl)-2-oxo-1,2-dihydro-pyrrolo[1,2-b]pyridazine-3-carboxylic acid ethyl ester as a yellow solid, which was used in the next step without further purification. LC-MS (ESI) calcd for $C_{16}H_{19}N_3O_4$ 317.14. found 318.3 [M+H$^+$]. FT-IR (ATR) $v_{max}$ (neat): 2231, 1642, 1610 cm$^{-1}$.

f) N-{3-[6-Cyano-4-hydroxy-1-(3-methyl-butyl)-2-oxo-1,2-dihydro-pyrrolo[1,2-b]pyridazin-3-yl]-1,1-dioxo-1,4-dihydro-1λ$^6$-benzo[1,2,4]thiadiazin-7-yl}-methanesulfonamide

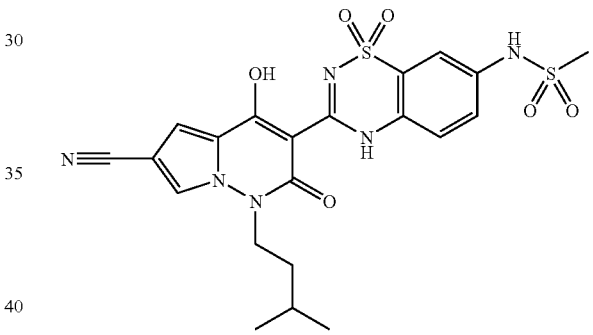

A solution of 6-cyano-4-hydroxy-1-(3-methyl-butyl)-2-oxo-1,2-dihydro-pyrrolo[1,2-b]pyridazine-3-carboxylic acid ethyl ester (Example 15e, 0.25 g, 0.788 mmol) and 2-amino-5-methanesulfonylamino-benzenesulfonamide (Example 3d, 0.209 g, 0.788 mmol) in pyridine (4 mL) was heated to 120° C. for 3 h. 1,8-Diazabicyclo[5.4.0]undec-7-ene (200 μL) was added and the mixture was heated at 120° C. for 16 h. The reaction mixture was passed through a plug of silica gel and eluted with 50%→100% ethyl acetate in hexanes. The solvents were removed in vacuo and purification by preparative HPLC (Column Luna 5μ C18 (2) 100 Å size 150×21.2 mm, 5 micron, 40%-95% in 11 min 25 mL/min flow rate, 0.05% trifluoroacetic acid in acetonitrile/0.05% trifluoroacetic acid in water) afforded the desired product, N-{3-[6-cyano-4-hydroxy-1-(3-methyl-butyl)-2-oxo-1,2-dihydro-pyrrolo[1,2-b]pyridazin-3-yl]-1,1-dioxo-1,4-dihydro-1λ$^6$-benzo[1,2,4]thiadiazin-7-yl}-methanesulfonamide (0.0275 g, 0.0531 mmol, 6.7% yield). $^1$H NMR (400 MHz, DMSO-d$_6$) δ: 0.94 (3H, s), 0.96 (3H, s), 1.17-1.23 (2H, m), 1.51-1.57 (2H, m), 1.65-1.75 (1H, m), 5.74 (1H, s), 3.05 (3H, s), 7.40 (1H, s), 7.49-7.57 (3H, m), 8.51 (1H, s), 10.12 (1H, s), 13.75 (1H, s). LC-MS (ESI) calcd for $C_{21}H_{22}N_6O_6S_2$ 518.10. found 519.4 [M+H$^+$].

EXAMPLE 16

N-{3-[4-Hydroxy-1-(3-methyl-butyl)-2-oxo-1,2-dihydro-pyrrolo[1,2-b]pyridazin-3-yl]-1,1-dioxo-1,4-dihydro-1λ⁶-benzo[1,4]thiazin-7-yl}-methanesulfonamide

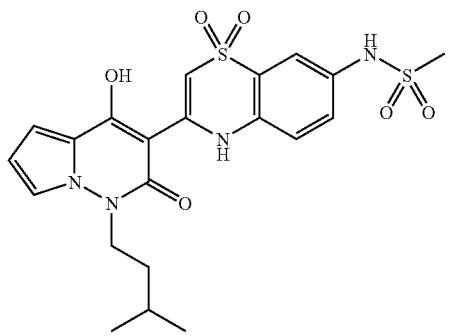

a) 1-[[2-(7-Methanesulfonylamino-1,1-dioxo-1,4-dihydro-1λ⁶-benzo[1,4] thiazin-3-yl)-acetyl]-(3-methyl-butyl)-amino]-1H-pyrrole-2-carboxylic acid allyl ester

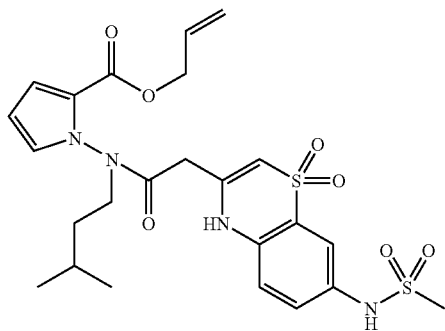

(7-Methanesulfonylamino-1,1-dioxo-1,4-dihydro-1λ⁶-benzo[1,4]thiazin-3-yl)-acetic acid (Example 8i, 0.1 g, 0.3 mmol) was dissolved in anhydrous N,N-dimethylformamide (3 mL). 1-(3-Methyl-butylamino)-1H-pyrrole-2-carboxylic acid allyl ester (Example 1c, 0.07 g, 0.3 mmol) was added followed by 1-(3-dimethylaminopropyl)-3-ethylcarbodiimide hydrochloride (0.06 g, 0.315 mmol). Then N-methylmorpholine (0.07 mL, 0.63 mmol) was added into the above reaction mixture. The mixture was stirred at 25° C. for 4 h. The solution was poured into 1.0 M aqueous hydrochloric acid solution (50 mL). The aqueous layer was extracted with ethyl acetate (2×50 mL). The organic phase was dried over sodium sulfate, filtered and concentrated in vacuo to afford the crude desired product, 1-[[2-(7-methanesulfonylamino-1,1-dioxo-1,4-dihydro-1λ⁶-benzo[1,4]thiazin-3-yl)-acetyl]-(3-methyl-butyl)-amino]-1H-pyrrole-2-carboxylic acid allyl ester (0.3 mmol) as a yellow oil, which was used in the next step without further purification. LC-MS (ESI) calcd for $C_{24}H_{30}N_4O_7S_2$ 550.16. found 551.6 [M+H⁺].

b) N-{3-[4-Hydroxy-1-(3-methyl-butyl)-2-oxo-1,2-dihydro-pyrrolo[1,2-b]pyridazin-3-yl]-1,1-dioxo-1,4-dihydro-1λ⁶-benzo[1,4]thiazin-7-yl}-methanesulfonamide

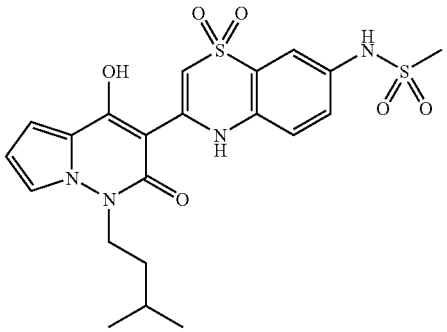

Crude 1-[[2-(7-methanesulfonylamino-1,1-dioxo-1,4-dihydro-1λ⁶-benzo[1,4]thiazin-3-yl)-acetyl]-(3-methyl-butyl)-amino]-1H-pyrrole-2-carboxylic acid allyl ester (Example 16a, 0.3 mmol) was dissolved in ethanol (3 mL). A 21% solution of sodium ethoxide in ethanol (0.448 mL, 1.2 mmol) was added into the above solution. The mixture was stirred at 60° C. for 4 h. Upon cooling to 25° C., the mixture was poured into 1.0 M aqueous hydrochloric acid solution (50 mL). The aqueous layer was extracted with ethyl acetate (2×50 mL). The organic phase was dried over sodium sulfate, filtered and concentrated in vacuo to afford a yellow solid. Purification by flash column chromatography (Teledyne Isco RediSep; 20% ethyl acetate in hexanes to 100% ethyl acetate in hexanes) afforded the desired product, N-{3-[4-hydroxy-1-(3-methyl-butyl)-2-oxo-1,2-dihydro-pyrrolo[1,2-b]pyridazin-3-yl]-1,1-dioxo-1,4-dihydro-1λ⁶-benzo[1,4]thiazin-7-yl}-methanesulfonamide (20 mg, 0.04 mmol, 13% yield over two steps) as a yellow solid. ¹H NMR (400 MHz, CDCl₃) δ: 1.05 (6H, d, J=6.6 Hz), 1.64-1.81 (3H, m), 3.11 (3H, s), 4.24-4.31 (2H, m), 5.53 (1H, s), 6.41-6.46 (1H, m), 6.97-7.10 (3H, m), 7.30-7.33 (1H, m), 7.60-7.64 (1H, m), 7.70-7.72 (1H, m). LC-MS (ESI) calcd for $C_{21}H_{24}N_4O_6S_2$ 492.11. found 493.3 [M+H⁺].

EXAMPLE 17

N-{3-[1-(3-Chloro-4-fluoro-benzyl)-4-hydroxy-2-oxo-1,2-dihydro-pyrrolo[1,2-b]pyridazin-3-yl]-1,1-dioxo-1,4-dihydro-1λ⁶-benzo[1,2,4]thiadiazin-7-yl}-methanesulfonamide

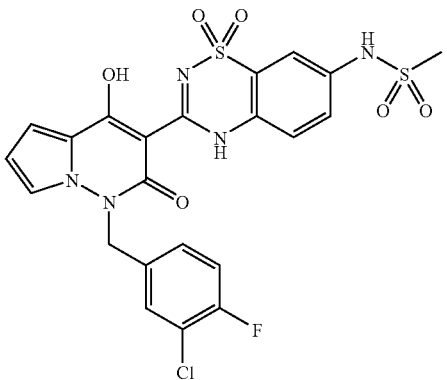

a) 2-Chloro-5-nitrobenzenesulfonamide

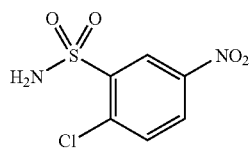

To a solution of thionyl chloride (11 mL) and 2-chloro-5-nitro-benzenesulfonic acid (4.78 g, 20.1 mmol) was added N,N-dimethylformamide (0.92 µL) and the reaction mixture was heated to reflux for 4 h. Upon cooling, the reaction mixture was azeotroped with toluene (2-3×). The sulfonyl chloride was dissolved in a minimal amount of toluene and then added to a mixture of concentrated aqueous ammonium hydroxide solution (25 mL) and tetrahydrofuran (25 mL) at −10° C. After stirring for 2 h the reaction was quenched by adding a 6.0 M aqueous hydrochloric acid solution until pH 4 was reached. The layers were separated and the organic layer was concentrated in vacuo to a slurry. Pentane was added and the product was isolated by vacuum filtration to afford the desired product, 2-chloro-5-nitrobenzenesulfonamide (2.0 g, 8.48 mmol, 42.4% yield) as a solid.

Alternatively, 2-chloro-5-nitrobenzenesulfonamide can be prepared as follows:

4-Chloronitrobenzene (10 g, 63.5 mmol) was charged into a flask, followed by addition of chlorosulfonic acid (21.1 mL, 317 mmol), and heated at 120° C. for 100 h. The reaction mixture was quenched by pouring it into ice (300 mL) containing 8.0 N aqueous ammonium hydroxide solution (200 mL), and the mixture was allowed to stir at 25° C. for 18 h. The desired product was extracted with ethyl acetate (400 mL) and filtered through Merck silica gel 60, 40-63 µm and concentrated in vacuo. The crude product was slurried in toluene (70 mL) at 70° C. for 2 h before filtering to afford the desired product, 2-chloro-5-nitro-benzenesulfonamide (4.75 g, 20.1 mmol, 29% yield) as a dark, brown solid. $^1$H NMR (400 MHz, DMSO-$d_6$) δ: 7.94 (d, 1H, J=8.8 Hz), 7.97 (bs, 2H), 8.40 (dd, 1H, $J_1$=8.6 Hz, $J_2$=3.1 Hz), 8.64 (d, 1H, J=3.1 Hz).

b) 2-Amino-5-nitrobenzenesulfonamide

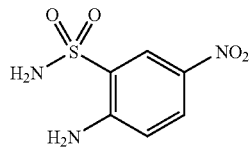

A mixture of 2-chloro-5-nitrobenzenesulfonamide (Example 17a, 0.88 g, 3.72 mmol), ammonium carbonate (0.88 g, 9.16 mmol), and copper(II)sulfate (0.175 g, 1.10 mmol) in concentrated aqueous ammonium hydroxide solution (4.4 mL) was heated for 4 h at 120° C. in a pressure reaction vessel. The mixture was allowed to cool to 25° C. and the resulting solid was collected by vacuum filtration, washed with water and dried to afford the desired product, 2-amino-5-nitrobenzenesulfonamide (0.295 g, 1.36 mmol, 36.5% yield) as a tan solid.

Alternatively, 2-amino-5-nitrobenzenesulfonamide can be prepared as follows:

To a suspension of 4-nitroanline-2-sulfonic acid sodium salt (20.00 g, 83.27 mmol) in sulfolane (83 mL) was slowly added phosphorous oxychloride (23 mL, 249.82 mmol) at 25° C. The mixture was heated at 120° C. for 3.5 h, allowed to cool to 25° C. and diluted with dichloromethane (300 mL). The mixture was filtered and the precipitate was washed with dichloromethane (200 mL). The filtrate was treated with ammonia gas for 10 minutes while cooling in an ice bath and then stirred at 25° C. for 5 minutes. The yellow solid was collected by vacuum filtration and the precipitate was further washed with dichloromethane (300 mL, then 200 mL), cold water (2×150 mL) and dried in vacuo for 16 h at 60° C. to afford the desired product, 2-amino-5-nitrobenzenesulfonamide (8.06 g, 37.14 mmol, 44% yield) as a yellow solid. $^1$H NMR (400 MHz, DMSO-$d_6$) δ: 6.89 (d, J=9.3 Hz, 1H), 7.12 (bs, 2H), 7.57 (bs, 2H), 8.07 (dd, $J_1$=9.0 Hz, $J_2$=2.6 Hz, 1H), 8.43 (d, J=3.0 Hz, 1H).

Alternatively, 2-amino-5-nitrobenzenesulfonamide can be prepared as follows:

To a suspension of 4-nitroanline-2-sulfonic acid sodium salt (20.00 g, 83.27 mmol) in sulfolane (83 mL) was slowly added phosphorous oxychloride (23 mL, 249.82 mmol) at 25° C. The mixture was heated at 120° C. for 3.5 h, allowed to cool to 25° C. and diluted with toluene (300 mL). The mixture was filtered and the precipitate was washed with toluene (200 mL). The filtrate was treated with ammonia gas for 10 minutes while cooling in an ice bath and then stirred at 25° C. for 5 minutes. The yellow solid was collected by vacuum filtration and the precipitate was further washed with toluene (300 mL, then 200 mL), cold water (2×150 mL) and dried in vacuo for 16 h at 60° C. to afford the desired product, 2-amino-5-nitrobenzenesulfonamide (7.39 g, 34.05 mmol, 41% yield) as a yellow solid. $^1$H NMR (400 MHz, DMSO-$d_6$) δ: 6.89 (d, J=9.3 Hz, 1H), 7.12 (bs, 2H), 7.57 (bs, 2H), 8.07 (dd, $J_1$=9.0 Hz, $J_2$=2.6 Hz, 1H), 8.43 (d, J=3.0 Hz, 1H).

Alternatively, 2-amino-5-nitrobenzenesulfonamide can be prepared as follows:

To a suspension of 2-amino-5-nitro-benzenesulfonic acid (3.00 g, 13.75 mmol) in sulfolane (10 mL) was slowly added phosphorous oxychloride (3.43 mL, 37.47 mmol) at 25° C. The mixture was heated at 120° C. for 3.5 h, allowed to cool to 25° C. and diluted with dichloromethane (50 mL). The mixture was filtered and the precipitate was washed with dichloromethane (50 mL). The filtrate was treated with ammonia gas for 10 minutes while cooling in an ice bath and then stirred at 25° C. for 5 minutes. The yellow solid was collected by vacuum filtration and the precipitate was further washed with dichloromethane (2×50 mL), cold water (2×50 mL) and dried in vacuo for 16 h at 60° C. to afford the desired product, 2-amino-5-nitrobenzenesulfonamide (1.46 g, 6.73 mmol, 49% yield) as a brown solid. $^1$H NMR (400 MHz, DMSO-$d_6$) δ: 6.89 (d, J=9.1 Hz, 1H), 7.19 (bs, 2H), 7.37 (bs, 2H), 8.07 (dd, $J_1$=8.9 Hz, $J_2$=2.3 Hz, 1H), 8.43 (d, J=3.0 Hz, 1H).

Alternatively, 2-amino-5-nitrobenzenesulfonamide can be prepared as follows:

To a suspension of 2-amino-5-nitro-benzenesulfonic acid (3.00 g, 13.75 mmol) in sulfolane (10 mL) was slowly added phosphorous oxychloride (3.43 mL, 37.47 mmol) at 25° C. The mixture was heated at 120° C. for 3.5 h, allowed to cool to 25° C. and slowly poured into aqueous ammonium hydroxide solution (30 mL) at 25° C. The pH of the solution was adjusted to ca. 6-7 upon which a solid precipitated. The solid was collected by vacuum filtration and the precipitate was washed water (100 mL) and dried in vacuo for 16 h at 60° C. to afford the desired product, 2-amino-5-nitrobenzenesulfonamide (1.87 g, 8.62 mmol, 63% yield) as a yellow-brown solid.

$^1$H NMR (400 MHz, DMSO-d$_6$) δ: 6.89 (d, J=9.1 Hz, 1H), 7.19 (bs, 2H), 7.37 (bs, 2H), 8.07 (dd, J$_1$=8.9 Hz, J$_2$=2.3 Hz, 1H), 8.43 (d, J=3.0 Hz, 1H).

c) 2,5-Diaminobenzenesulfonamide

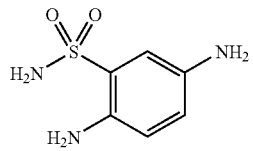

A mixture of 2-amino-5-nitrobenzenesulfonamide (Example 17b, 10 g, 46.08 mmol), 10% palladium on charcoal (~1 g) in tetrahydrofuran (250 mL) was hydrogenated for 26 h at 25° C. under 1 atmosphere of hydrogen gas via balloon. The mixture was then filtered through Celite, washed with tetrahydrofuran, and the solvent removed in vacuo to afford the desired product. The catalyst/Celite mixture was slurried in methanol (400 mL) for 16 h, filtered and the solvent was removed in vacuo to afford a second batch of the desired product, 2,5-diaminobenzenesulfonamide (combined: 7.79 g, 41.65 mmol, 90.4% yield) as a light-brown solid. $^1$H NMR (400 MHz, DMSO-d$_6$) δ: 4.54 (2H, bs), 4.98 (2H, bs), 6.55-6.60 (2H, m), 6.87 (1H, d, J=2.2 Hz), 6.99 (2H, bs). LC-MS (ESI) calcd for C$_6$H$_9$N$_3$O$_2$S 187.04. found 188.3 [M+H$^+$].

Alternatively, 2,5-diaminobenzenesulfonamide can be prepared as follows:

i) 2-Benzylamino-5-nitro-benzenesulfonamide

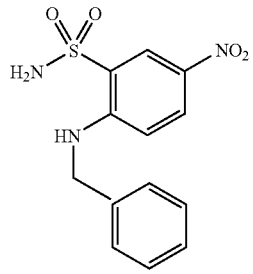

A solution of 2-chloro-5-nitro-benzenesulfonamide (20 g, 84.52 mmol) in acetonitrile (169 mL) was treated with benzylamine (13.85 mL, 126.78 mmol), diisopropyl ethylamine (29.44 mL, 169.04 mmol) and stirred for 16 h at 55° C. The reaction was cooled to 25° C., poured into water (1.0 L) then placed in an ice bath while stirring. After 4 h a precipitate was filtered off and washed with the mother liquor to afford the desired product, 2-benzylamino-5-nitro-benzenesulfonamide (21.65 g, 70.45 mmol, 83.3% yield) as a yellow solid. $^1$H NMR (400 MHz, DMSO-d$_6$) δ: 4.64 (2H, d, J=4.6 Hz), 6.81 (1H, d, J=9.4 Hz), 7.23-7.44 (6H, m), 7.77 (2H, bs), 8.11 (1H, dd, J$_1$=9.4 Hz, J$_2$=2.3 Hz), 8.49 (1H, d, J=3.1 Hz). LC-MS (ESI) calcd for C$_{13}$H$_{13}$N$_3$O$_4$S 307.06. found 308.2 [M+H$^+$] (100%), 615.2 [2M+H$^+$] (81%).

ii) 2,5-Diamino-benzenesulfonamide

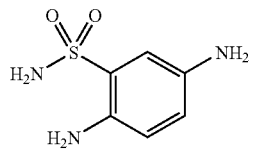

A mixture of 2-benzylamino-5-nitro-benzenesulfonamide (Example 17ci, 15 g, 48.81 mmol) and 5% palladium on activated carbon powder (wet, nominally 50% water, 6 g) in methanol (500 mL) was heated to 55° C. The mixture was degassed while stirring and the flask was charged with hydrogen gas via balloon. After stirring for 16 h under 1 atmosphere of hydrogen gas, the reaction was filtered through Celite and concentrated in vacuo to afford the desired product, 2,5-diamino-benzenesulfonamide (8.55 g, 45.67 mmol, 93.6% yield) as a tan solid. $^1$H NMR (400 MHz, DMSO-d$_6$) δ: 4.56 (2H, bs), 4.98 (2H, bs), 6.58-6.59 (2H, m), 6.87 (1H, d, J=1.6 Hz), 7.00 (2H, s). LC-MS (ESI) calcd for C$_6$H$_9$N$_3$O$_2$S 187.04. found 188.2 [M+H$^+$] (100%).

d) 2-Amino-5-methanesulfonylamino-benzenesulfonamide

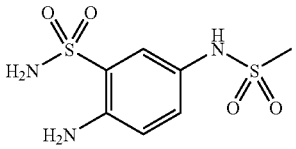

2,5-Diaminobenzenesulfonamide (Example 17c, 11.16 g, 59.61 mmol) was dissolved in acetonitrile (300 mL) and pyridine (7.07 g, 89.41 mmol) was added. Methanesulfonyl chloride (7.17 g, 62.59 mmol) was added dropwise over a period of 10 min and the reaction mixture was stirred for 16 h at 25° C. after which time a precipitate had formed. Most of the acetonitrile was removed in vacuo and water (200 mL) was added to afford a clear solution. The product slowly started to precipitate and the mixture was placed in an ice bath for 3 h. The precipitate was collected by vacuum filtration and dried under high vacuum to afford the desired product, 2-amino-5-methanesulfonylamino-benzenesulfonamide (also made in Examples 3d and 3d') (11.1 g, 41.84 mmol, 70.2% yield) as a brown solid. $^1$H NMR (400 MHz, CD$_3$OD) δ: 2.89 (3H, s), 6.82 (1H, d, J=8.5 Hz), 7.20 (1H, dd, J$_1$=8.5 Hz, J$_2$=2.5 Hz), 7.58 (1H, d, J=2.5 Hz). LC-MS (ESI) calcd for C$_7$H$_{11}$N$_3$O$_4$S$_2$ 265.02. found 266.0 [M+H$^+$].

e) N-(4-Methanesulfonylamino-2-sulfamoyl-phenyl)-malonamic acid ethyl ester

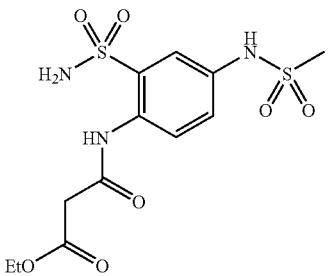

2-Amino-5-methanesulfonylamino-benzenesulfonamide (Example 17d, 23.27 g, 87.81 mmol) was dissolved in N,N-dimethylacetamide (100 mL) and diethyl ether (100 mL). Ethyl 3-chloro-3-oxo-propionate (13.88 g, 92.20 mmol) was added and the reaction mixture was stirred at 25° C. for 1 h. The reaction mixture was diluted with ethyl acetate (400 mL) and was extracted with water (400 mL). The aqueous layer was back-extracted with ethyl acetate (2×200 mL). The combined organic layers were dried over sodium sulfate, filtered and most of the solvent was removed in vacuo to a volume of ~100 mL. To the stirred solution was added hexanes (100 mL) upon which a precipitate formed. The precipitate was collected by vacuum filtration, washed with hexanes and dried under high vacuum to afford the analytically pure product, N-(4-methanesulfonylamino-2-sulfamoyl-phenyl)-malonamic acid ethyl ester (31.22 g, 85.53 mmol, 97.4% yield) as a light-brown solid. $^1$H NMR (400 MHz, CD$_3$OD) δ: 1.31 (3H, t, J=7.0 Hz), 3.00 (3H, s), 3.59 (2H, s), 4.25 (2H, quartet, J=6.9 Hz), 7.42-7.45 (1H, m), 7.86 (1H, m), 7.92 (1H, d, J=8.8 Hz).

Alternatively, N-(4-methanesulfonylamino-2-sulfamoyl-phenyl)-malonamic acid ethyl ester can be prepared as follows:

To 2-amino-5-methanesulfonylamino-benzenesulfonamide (Example 17d, 175 mg, 0.66 mmol) was added diethyl malonate (297 mg, 1.66 mmol) and heated at 160° C. for 60 min. After cooling down to 25° C., a 1:1 mixture of ethyl acetate/hexanes (5 mL) was added, upon which as a white solid precipitated out. The solid was collected by vacuum filtration, washed twice with a 1:1 mixture of ethyl acetate/hexanes, and dried under high vacuum to afford the desired product, N-(4-methanesulfonylamino-2-sulfamoyl-phenyl)-malonamic acid ethyl ester (179 mg, 0.47 mmol, 72% yield) as an off-white solid. $^1$H NMR (400 MHz, CD$_3$OD) δ: 1.32 (t, 3H, J=7.0 Hz), 3.00 (s, 3H), 3.60 (s, 2H), 4.25 (quartet, 2H, J=6.8 Hz), 7.44 (dd, 1H, J$_1$=3.2 Hz, J$_2$=8.4 Hz), 7.87 (d, 1H, J=5.6 Hz), 7.92 (d, 1H, J=8.4 Hz). LC-MS (ESI$^+$) calcd for C$_{12}$H$_{17}$N$_3$O$_7$S$_2$ 379.05. found 380.1 [M+H$^+$].

f) N-(4-Methanesulfonylamino-2-sulfamoylphenyl) malonamic acid methyl ester

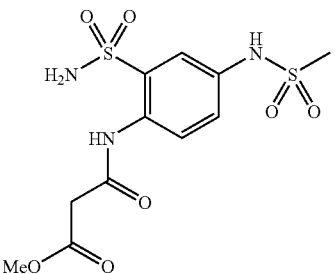

Methyl malonyl chloride (9.05 mL, 84.4 mmol) was added dropwise over 10 min to a solution of 2-amino-5-methanesulfonylaminobenzenesulfonamide (Example 17d, 20.35 g, 76.7 mmol) in N,N-dimethylacetamide (90 mL) at 0° C. The mixture was allowed to warm to 25° C. and stirred at that temperature for 1 h. A solution of sodium bicarbonate (7.09 g, 84.4 mmol) in water (200 mL) was then added via addition funnel over 15 min (gas evolution and a mild exotherm were noted) followed by the rapid addition of an additional volume of water (200 mL). The resulting solution was then seeded with a small amount of N-(4-methanesulfonylamino-2-sulfamoylphenyl)malonamic acid methyl ester (ca. 15 mg). The mixture was stirred for 21 h at 25° C. during which time a tan precipitate formed. This material was collected by filtration, washed with water (150 mL), and was dried in a vacuum oven at 50° C. to afford the desired product, N-(4-methanesulfonylamino-2-sulfamoylphenyl)-malonamic acid methyl ester (24.33 g, 66.6 mmol, 87% yield) as a tan solid. $^1$H NMR (400 MHz, DMSO-d$_6$) δ: 3.02 (3H, s), 3.60 (2H, s), 3.66 (3H, s), 7.38 (1H, dd, J$_1$=2.3 Hz, J$_2$=8.6 Hz), 7.53 (2H, bs), 7.73 (1H, d, J=2.4 Hz), 7.83 (1H, d, J=8.7 Hz), 9.43 (1H, s), 9.99 (1H, s).

g) (7-Methanesulfonylamino-1,1-dioxo-1,4-dihydro-1λ$^6$-benzo[1,2,4]thiadiazin-3-yl)-acetic acid

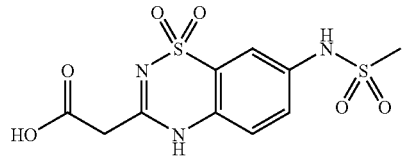

N-(4-Methanesulfonylamino-2-sulfamoyl-phenyl)-malonamic acid ethyl ester (Example 17e, 9.55 g, 26.16 mmol) was dissolved in 8% aqueous sodium hydroxide solution (262 mL) and heated at 100° C. for 1.5 h. The reaction mixture was cooled to 0° C. and the solution was acidified by slowly adding 12.0 M aqueous hydrochloric acid solution until pH 1-2 was reached. A precipitate started to form and the suspension was allowed to stir for 30 min at 0° C. The precipitate was collected by vacuum filtration, washed with cold water, and dried under high vacuum to afford (7-methanesulfonylamino-1,1-dioxo-1,4-dihydro-1λ$^6$-benzo[1,2,4]thiadiazin-3-yl)-acetic acid (7.20 g, 21.621 mmol, 82.6% yield) as a pinkish solid. $^1$H NMR (400 MHz, DMSO-d$_6$) δ: 3.03 (3H, s), 3.56 (2H, s), 7.33 (1H, d, J=9.1 Hz), 7.52-7.54 (2H, m), 10.09 (1H, s), 12.24 (1H, s), 13.02 (1H, bs). LC-MS (ESI) calcd for C$_{10}$H$_{11}$N$_3$O$_6$S$_2$ 333.01. found 334.1 [M+H$^+$].

Alternatively, (7-methanesulfonylamino-1,1-dioxo-1,4-dihydro-1λ$^6$-benzo[1,2,4]thiadiazin-3-yl)-acetic acid can be prepared from 17f as follows:

N-(4-Methanesulfonylamino-2-sulfamoylphenyl)-malonamic acid methyl ester (Example 17f, 21.75 g, 59.53 mmol) was dissolved in an aqueous solution of sodium hydroxide (7.14 g, 178.5 mmol; dissolved in 180 mL water) at 25° C. The reaction mixture was heated to 100° C. for 1 h, then was gradually cooled over 30 min to 0° C. 12.0 M Aqueous hydrochloric acid solution (20 mL, 240 mmol) was added dropwise over 10 min via addition funnel resulting in the formation of a tan precipitate. The mixture was allowed to warm to 25° C. and was stirred at that temperature for 21 h. The precipitate was collected by filtration, washed with water (150 mL), and was dried in a vacuum oven at 45° C. for 22 h to afford (7-methanesulfonylamino-1,1-dioxo-1,4-dihydro-1λ$^6$-benzo[1,2,4]thiadiazin-3-yl)-acetic acid (18.36 g, 55.1 mmol, 93% yield) as a tan solid. $^1$H NMR (400 MHz, DMSO-d$_6$) δ: 3.03 (3H, s), 3.56 (2H, s), 7.32-7.34 (1H, m), 7.51-7.54 (2H, m), 10.09 (1H, s), 12.26 (1H, s), 13.01 (1H, bs). LC-MS (ESI) calcd for C$_{10}$H$_{11}$N$_3$O$_6$S$_2$ 333.01. found 334.1 [M+H$^+$].

h) 1-(3-Chloro-4-fluoro-benzylamino)-1H-pyrrole-2-carboxylic acid allyl ester

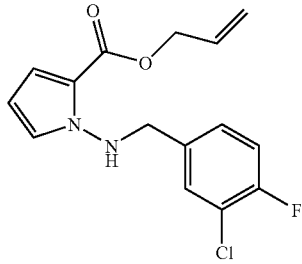

Sodium cyanoborohydride (1.11 g, 16.8 mmol) was added to a solution of 1-amino-1H-pyrrole-2-carboxylic acid allyl ester (Example 1b, 1.12 g, 6.74 mmol), 3-chloro-4-fluorobenzaldehyde (1.32 g, 8.08 mmol) and acetic acid (1.2 mL), in methanol (50 mL) at 25° C. The reaction mixture was stirred at 25° C. for 18 h, quenched with saturated aqueous sodium bicarbonate solution and was extracted with ethyl acetate (2×50 mL). The organic layers were dried over magnesium sulfate, filtered and concentrated in vacuo. Purification of the residue by flash column chromatography (Teledyne Isco RediSep 40 g, 0→40% ethyl acetate in hexanes) afforded the desired product, 1-(3-chloro-4-fluoro-benzylamino)-1H-pyrrole-2-carboxylic acid allyl ester (1.36 g, 4.41 mmol, 65% yield) as an off-white oil. $^1$H NMR (400 MHz, CDCl$_3$) δ 4.06 (2H, d, J=5.5 Hz), 4.76 (2H, d, J=5.3 Hz), 5.29 (1H, d, J=11.0 Hz), 5.40 (1H, d, J=16.4 Hz), 5.96-6.05 (2H, m), 6.58 (1H, t, J=5.5 Hz), 6.76 1H, (t, J=1.9 Hz), 6.91 (1H, dd, J$_1$=4.3 Hz, J$_2$=1.8 Hz), 7.06 (1H, t, J=8.6 Hz), 7.10-7.14 (1H, m), 7.33 (1H, dd, J$_1$=7.1 Hz, J$_2$=1.4 Hz).

i) 1-{(3-Chloro-4-fluoro-benzyl)-[2-(7-methanesulfonylmethyl-1,1-dioxo-1,4-dihydro-1λ$^6$-benzo[1,2,4]thiadiazin-3-yl)-acetyl]-amino}-1H-pyrrole-2-carboxylic acid allyl ester

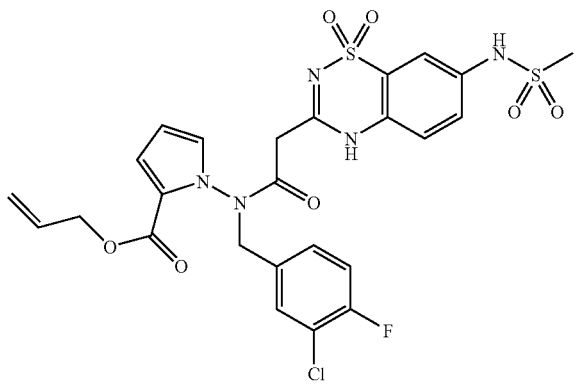

To a solution of 1-(3-chloro-4-fluoro-benzylamino)-1H-pyrrole-2-carboxylic acid allyl ester (Example 17h, 150.7 mg, 0.488 mmol) in N,N-dimethylformamide (3.0 mL) was added (7-methanesulfonylamino-1,1-dioxo-1,4-dihydro-1λ$^6$-benzo[1,2,4]thiadiazin-3-yl)-acetic acid (Example 17f, 195.2 mg, 0.586 mmol), 4-dimethylaminopyridine (18.1 mg, 0.147 mmol), and 1-[3-(dimethylamino)propyl]-3-ethylcarbodiimide hydrochloride (114.5 mg, 0.586 mmol). After stirring at 25° C. for 12 h, the mixture was diluted with ethyl acetate and acidified with 1.0 M aqueous hydrochloric acid solution to pH 1. The organic layer was separated and the aqueous layer was extracted with ethyl acetate (2×20 mL). The combined organic layers were dried over anhydrous magnesium sulfate, filtered, concentrated and dried in vacuo to afford the crude desired product, 1-{(3-chloro-4-fluoro-benzyl)-[2-(7-methanesulfonylmethyl-1,1-dioxo-1,4-dihydro-1λ$^6$-benzo[1,2,4]thiadiazin-3-yl)-acetyl]-amino}-1H-pyrrole-2-carboxylic acid allyl ester as a faintly yellow oil. The crude desired product was used in the next step without further purification. LC-MS (ESI) calcd for C$_{25}$H$_{23}$ClFN$_5$O$_7$S$_2$ 623.07. found 624.2 [M+H$^+$].

j) N-{3-[1-(3-Chloro-4-fluoro-benzyl)-4-hydroxy-2-oxo-1,2-dihydro-pyrrolo[1,2-b]pyridazin-3-yl]-1,1-dioxo-1,4-dihydro-1λ$^6$-benzo[1,2,4]thiadiazin-7-yl}-methanesulfonamide

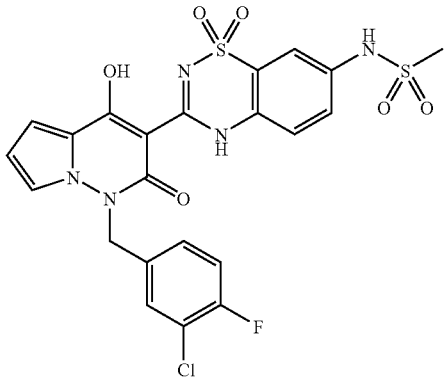

To a solution of 1-{(3-chloro-4-fluoro-benzyl)-[2-(7-methanesulfonylmethyl-1,1-dioxo-1,4-dihydro-1λ$^6$-benzo[1,2,4]thiadiazin-3-yl)-acetyl]-amino}-1H-pyrrole-2-carboxylic acid allyl ester (Example 17i, 304.5 mg, 0.488 mmol) in absolute ethanol (5 mL) was added a 21% solution of sodium ethoxide in ethanol (1.1 mL, 2.95 mmol). After stirring at 60° C. for 12 h, the mixture was diluted with ethyl acetate and acidified with 1.0 M aqueous hydrochloric acid solution upon which a precipitate formed. The solid was collected by vacuum filtration to afford the desired product, N-{3-[1-(3-chloro-4-fluoro-benzyl)-4-hydroxy-2-oxo-1,2-dihydro-pyrrolo[1,2-b]pyridazin-3-yl]-1,1-dioxo-1,4-dihydro-1λ$^6$-benzo[1,2,4]thiadiazin-7-yl}-methanesulfonamide (88.5 mg, 0.156 mmol, 32% yield) as an off-white solid. The filtrate was extracted with ethyl acetate (2×20 mL). The combined organic layers were dried over anhydrous magnesium sulfate, filtered and concentrated in vacuo. The crude mixture was purified by HPLC purification (Column Luna 5μ C18 (2) 100 Å AXIA 150×21.2 mm, 5 micron, 25%-100% in 12 min 30 mL/min flow rate, 0.05% trifluoroacetic acid in acetonitrile/0.05% trifluoroacetic acid in water) to afford more of the desired product, N-{3-[1-(3-chloro-4-fluoro-benzyl)-4-hydroxy-2-oxo-1,2-dihydro-pyrrolo[1,2-b]pyridazin-3-yl]-1,1-dioxo-1,4-dihydro-1λ$^6$-benzo[1,2,4]thiadiazin-7-yl}-methanesulfonamide (18.4 mg, 0.033 mmol, 7% yield; total 39% yield) as an off-white solid. $^1$H NMR (400 MHz, DMSO-d$_6$) δ 3.06 (3H, s), 5.61 (2H, s), 6.57 (1H, s), 6.98 (1H, s), 7.37 (2H, d, J=7.6 Hz), 7.52 (1H, dd, J$_1$=8.5 Hz, J$_2$=2.4 Hz), 7.59-7.68 (4H, m), 10.17 (1H, s). LC-MS (ESI) calcd for C$_{22}$H$_{17}$ClFN$_5$O$_6$S$_2$ 565.03. found 566.2 [M+H$^+$].

Biological Testing

The ability of compounds of Formula I to inhibit HCV replication can be demonstrated in the following in vitro assays.

Compounds were tested for HCV polymerase inhibition. Assays were performed in a 96-well streptavidin-coated FlashPlate using 20 nM enzyme, 0.5 μCi of [α-$^{33}$P]GTP, 0.6 μM GTP, and 250 nM 5'biotinylated oligo (rG$_{13}$)/poly rC in 20 mM Tris-HCl, pH 7.5, 5 mM MgCl$_2$, 5 mM dithiothreitol, 0.1 μL bovine serum albumin, and 100 U/mL RNAse inhibitor. The reaction was stopped by aspiration after 75 min at 28° C. and the plate was washed several times. After washing and drying the plate, incorporated radioactivity was counted using a Microbeta scintillation counter. IC$_{50}$ values were calculated relative to the uninhibited control and inhibition data were fitted to a 4-parameter $IC_{50}$ equation. For very potent inhibitors, the data were fitted to a tight binding quadratic equation to obtain $IC_{50}$ values.

Test results ($IC_{50}$ values) for compounds of Formula I are summarized in Table 1, wherein ++ means NS5B polymerase inhibition with $IC_{50}$ values less than 0.10 μM, and + means $IC_{50}$ values between 0.10 μM and 3 μM.

TABLE 1

| Example # | NS5B Polymerase IC50 |
|---|---|
| 1 | + |
| 2 | + |
| 3 | ++ |
| 4 | ++ |
| 5 | ++ |
| 6 | + |
| 7 | + |
| 8 | ++ |
| 9 | ++ |
| 10 | + |
| 11 | + |
| 12 | + |
| 13 | + |
| 14 | ++ |
| 15 | + |
| 16 | ++ |
| 17 | ++ |

HCV Replicon Assay (Replicon $EC_{50}$ (μM))

The cell culture component of the assay is performed essentially as described by Bartenschlager et al., *Hepatology*, 35, 694-703 (2002), wherein exponentially growing HCV Huh-7/C24 replicon cells are seeded at $4.5 \times 10^3$ cells/well in 96 well plates and 24 hours later are treated with six point half-log concentration of compound. After 72 hours exposure the media is discarded from the compound assay plate and the cell monolayers are lysed by addition of 150 μl lysis mixture (Genospectra) with incubation at 53° C. for 45 minutes. Following incubation, each lysate is thoroughly mixed and 5 μl (NS3 probe) or 10 μl (GAPDH probe) of each lysate is then transferred to the capture plate and analyzed by bDNA assay.

Branched DNA (bDNA) Assay

Based on provided sequences for NS3 [AJ242652], Genospectra (Fremont, Calif., USA) designed and synthesized probes to these analytes (together with GAPDH). Cellular bDNA analysis is carried out essentially as described in the Genospectra protocol (details in Shyamala, V. et al., *Anal Biochem*, 266, 140-7 (1999)), wherein target specific capture extenders, label extenders and blocking probes are added to the capture plate after the addition of 5 or 10 μl cell lysate. After annealing overnight, during which the target RNA is captured to the plate via interaction with the capture extenders, the plate is washed, and then amplifier (which binds via the label extenders) and label probe are sequentially added.

After subsequent addition of the chemilumigenic substrate (dioxetan), each plate is read by luminometer (Wallac 1420 Multilabel HTS Counter Victor 2). The luminescence signal is proportional to the amount of mRNA present in each lysate. In addition to the samples, cell lysate only (no probe) background controls are also included on each bDNA assay plate and the average signal from these control wells is subtracted from the sample reading prior to analysis. Percent of no drug control is determined for both the NS3 and GAPDH signals for each compound also. Percent inhibition is determined for each compound concentration in relation to the no drug control to calculate the $EC_{50}$.

It is to be understood that the foregoing description is exemplary and explanatory in nature, and is intended to illustrate the invention and its preferred embodiments. Through routine experimentation, the artisan will recognize apparent modifications and variations that may be made without departing from the spirit of the invention.

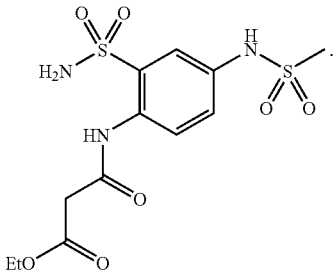

4. The compound of claim 1 having the following formula:
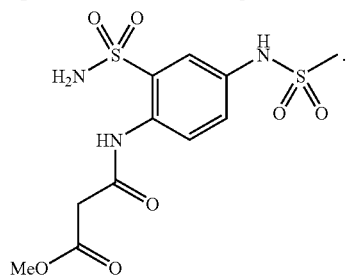

What is claimed is:

1. A compound selected from:

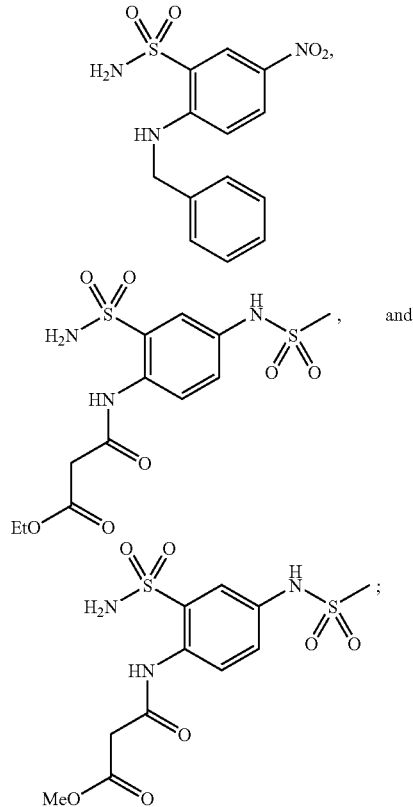

and tautomers thereof.

2. The compound of claim 1 having the following formula:

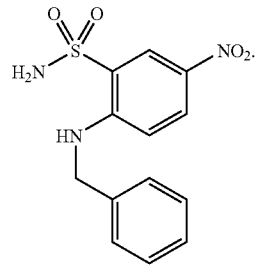

3. The compound of claim 1 having the following formula: